US008883171B2

(12) United States Patent
Ross et al.

(10) Patent No.: US 8,883,171 B2
(45) Date of Patent: Nov. 11, 2014

(54) COMPUTATIONALLY OPTIMIZED BROADLY REACTIVE ANTIGENS FOR INFLUENZA

(75) Inventors: Ted M. Ross, Pittsburgh, PA (US); Brendan M. Giles, Centennial, CO (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 13/822,844

(22) PCT Filed: Sep. 9, 2011

(86) PCT No.: PCT/US2011/051072
§ 371 (c)(1),
(2), (4) Date: Mar. 13, 2013

(87) PCT Pub. No.: WO2012/036993
PCT Pub. Date: Mar. 22, 2012

(65) Prior Publication Data
US 2013/0183342 A1 Jul. 18, 2013

Related U.S. Application Data

(60) Provisional application No. 61/403,407, filed on Sep. 14, 2010.

(51) Int. Cl.
| | | |
|---|---|---|
| *C07K 14/11* | (2006.01) | |
| *A61K 39/145* | (2006.01) | |
| *C07K 14/005* | (2006.01) | |
| *C07K 14/08* | (2006.01) | |
| *C07K 14/00* | (2006.01) | |
| *A61K 39/00* | (2006.01) | |

(52) U.S. Cl.
CPC ............. *C07K 14/11* (2013.01); *C07K 2319/00* (2013.01); *C12N 2760/16323* (2013.01); *C12N 2760/16234* (2013.01); *A61K 39/145* (2013.01); *C12N 2760/16123* (2013.01); *C12N 2760/16223* (2013.01); *C12N 2760/16134* (2013.01); *C12N 2760/16334* (2013.01); *C12N 2760/16122* (2013.01); *A61K 39/00* (2013.01); *C07K 14/005* (2013.01); *A61K 2039/5258* (2013.01)
USPC .................. 424/209.1; 424/210.1; 424/184.1; 424/94.1; 424/206.1; 536/23.72; 530/350; 435/5; 435/320.1; 435/369; 435/188

(58) Field of Classification Search
CPC ............. C07K 14/005; C07K 2319/00; C07K 2317/34; C07K 16/1018; C07K 2316/96; C07K 2317/76; A61K 39/145; A61K 2039/5258; A61K 39/12; C12N 2760/16134; C12N 2760/16122; C12N 2760/16151; C12N 2760/1602
See application file for complete search history.

(56) References Cited

U.S. PATENT DOCUMENTS

| | | | | |
|---|---|---|---|---|
| 7,566,454 | B2 * | 7/2009 | Lu et al. ....................... | 424/184.1 |
| 2005/0181459 | A1 * | 8/2005 | Baker et al. .................... | 435/7.2 |
| 2008/0045472 | A1 * | 2/2008 | Brahmachari et al. .......... | 514/44 |
| 2009/0074803 | A1 * | 3/2009 | Sallberg et al. ............. | 424/186.1 |
| 2009/0291472 | A1 * | 11/2009 | Lu et al. ........................ | 435/69.1 |
| 2009/0327170 | A1 * | 12/2009 | Donati et al. ................... | 706/12 |
| 2010/0041740 | A1 | 2/2010 | Wong et al. | |

FOREIGN PATENT DOCUMENTS

| | | |
|---|---|---|
| WO | WO 2008/028946 | 3/2008 |
| WO | WO 2009/073330 | 6/2009 |
| WO | WO 2010/36970 A2 * | 4/2012 |

OTHER PUBLICATIONS

Darminto,D., Dharmayanti,N.L.P.I., Indriani,R., Komadina,N. and Selleck,P. NCBI GenBank Acc. No. ABU99095.1. Direct Submission Aug. 27, 2007.*
Wang S, Taaffe J, Parker C, Solórzano A, Cao H, Garcia-Sastre A, Lu S. Hemagglutinin (HA) proteins from H1 and H3 serotypes of influenza A viruses require different antigen designs for the induction of optimal protective antibody responses as studied by codon-optimized HA DNA vaccines. J Virol. Dec. 2006;80(23):11628-37. Epub Sep. 20, 2006.*
Giles BM, Ross TM. Computationally optimized antigens to overcome influenza viral diversity. Expert Rev Vaccines. Mar. 2012;11(3):267-9.*
Butt AM, Siddique S, Idrees M, Tong Y. Avian influenza A (H9N2): computational molecular analysis and phylogenetic characterization of viral surface proteins isolated between 1997 and 2009 from the human population. Virol J. Nov. 15, 2010;7:319.*
Cai Z, Zhang T, Wan XF. A computational framework for influenza antigenic cartography. PLoS Comput Biol. Oct. 7, 2010;6(10):e1000949.*
Parida R, Shaila MS, Mukherjee S, Chandra NR, Nayak R. Computational analysis of proteome of H5N1 avian influenza virus to define T cell epitopes with vaccine potential. Vaccine. Oct. 23, 2007;25(43):7530-9. Epub Sep. 12, 2007.*
Somvanshi P, Singh V, Seth PK. Prediction of epitopes in hemagglutinin and neuraminidase proteins of influenza A virus H5N1 strain: a clue for diagnostic and vaccine development. OMICS. Mar. 2008;12(1):61-9.*
Tang XC, Lu HR, Ross TM. Hemagglutinin displayed baculovirus protects against highly pathogenic influenza. Vaccine. Oct. 4, 2010;28(44):6821-31. doi:10.1016/j.vaccine.2010.08.040. Epub Aug. 18, 2010.*
Beckman Coulter. "Codon optimization to PCR." Nature. Oct. 2, 2003;425(6957):540.*

(Continued)

*Primary Examiner* — Benjamin P Blumel
*Assistant Examiner* — Rachel Gill
(74) *Attorney, Agent, or Firm* — Klarquist Sparkman, LLP

(57) ABSTRACT

Described herein is the development of a computationally optimized influenza HA protein that elicits broadly reactive immune response to all H5N1 influenza virus isolates. The optimized HA protein was developed through a series of HA protein alignments, and subsequent generation of consensus sequences, for clade 2 H5N1 influenza virus isolates. The final consensus HA amino acid sequence was reverse translated and optimized for expression in mammalian cells. Influenza virus-like particles containing the optimized HA protein are an effective vaccine against H5N1 influenza virus infection in animals.

13 Claims, 23 Drawing Sheets

(56) References Cited

OTHER PUBLICATIONS

Tang Y, Wu P, Peng D, Wang X, Wan H, Zhang P, Long J, Zhang W, Li Y, Wang W, Zhang X, Liu X. Characterization of duck H5N1 influenza viruses with differing pathogenicity in mallard (*Anas platyrhynchos*) ducks. Avian Pathol. Dec. 2009;38(6):457-67. Epub Nov. 24, 2009.*

Tang et. al. NCBI GenBank Direct Submission: ABW21677, Oct. 7, 2007.*

Tang et. al. NCBI GenBank Direct Submission: EU195416, Oct. 7, 2007.*

Jiang Y, Yu K, Zhang H, Zhang P, Li C, Tian G, Li Y, Wang X, Ge J, Bu Z, Chen H. Enhanced protective efficacy of H5 subtype avian influenza DNA vaccine with codon optimized HA gene in a pCAGGS plasmid vector. Antiviral Res. Sep. 2007;75(3):234-41. Epub Apr. 9, 2007.*

Darminto D et. al. NCBI GenBank Direct Submission: ABU99095, Pub. May 1, 2008.*

Tao et al., "Virus-Like Particle Vaccine Comprised of the HA, NA, and M1 Proteins of an Avian Isolated H5N1 Influenza Virus Induces Protective Immunity Against Homologous and Heterologous Strains in Mice," *Viral Immunol.*, vol. 22(4):273-281, 2009.

* cited by examiner

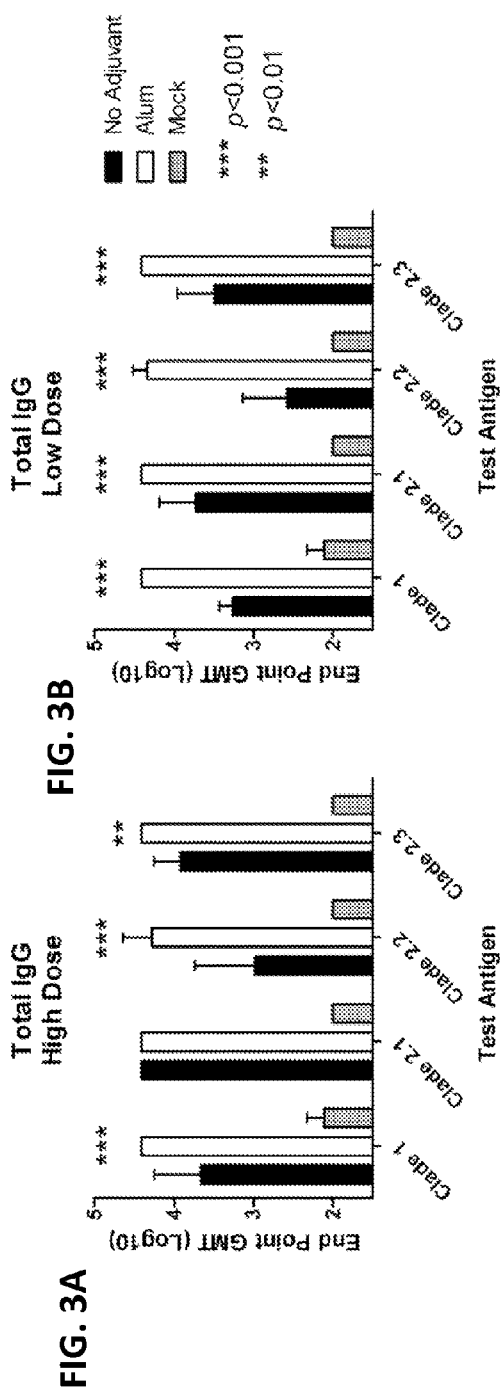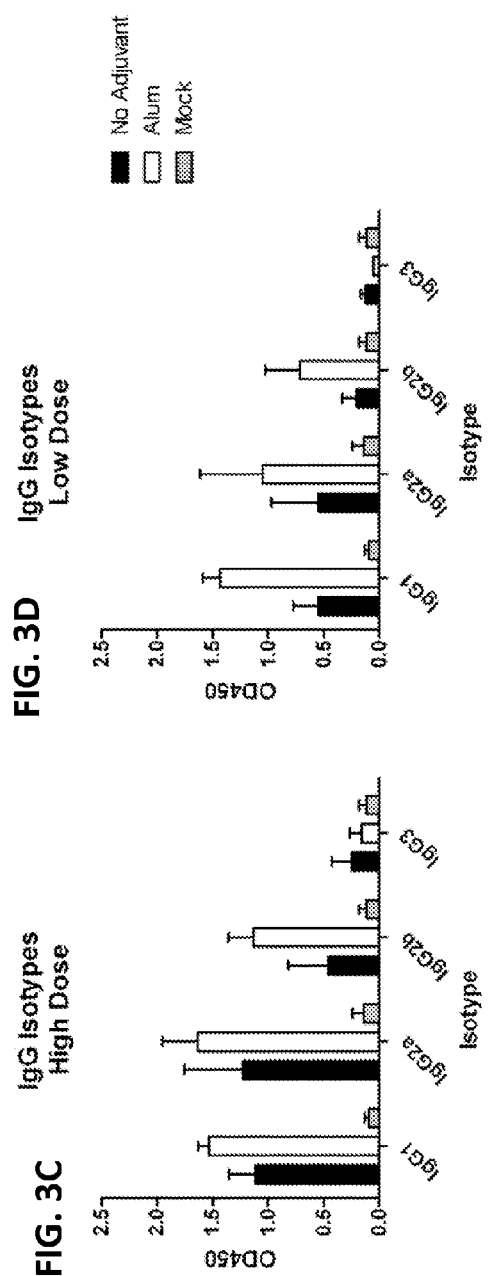

HAI Titer
High Dose

HAI Titer
Low Dose

FIG. 6A Weight Loss

FIG. 6B Relative Sickness

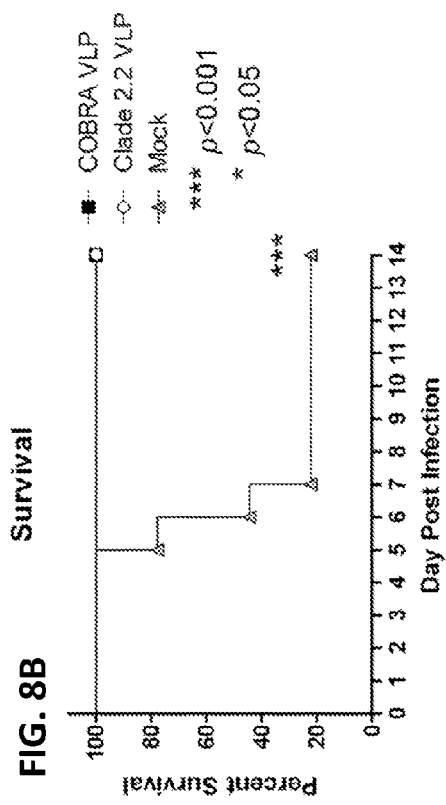
FIG. 8A Weight Loss
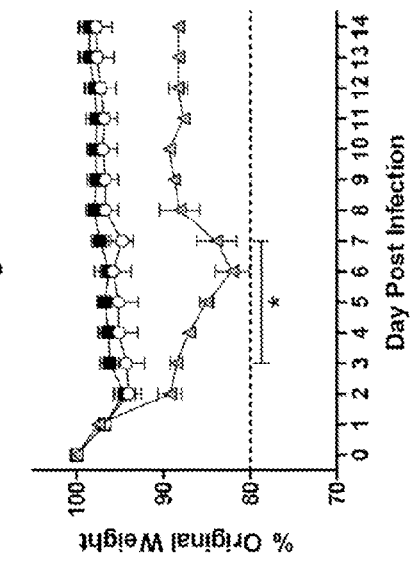
FIG. 8B Survival
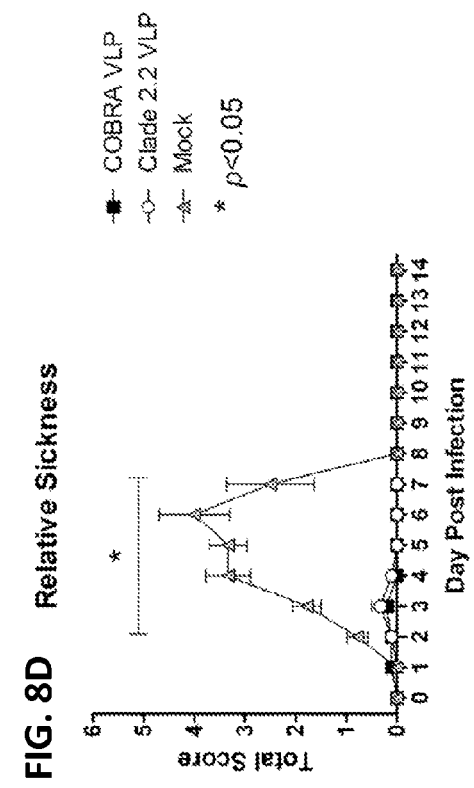
FIG. 8C Temperature
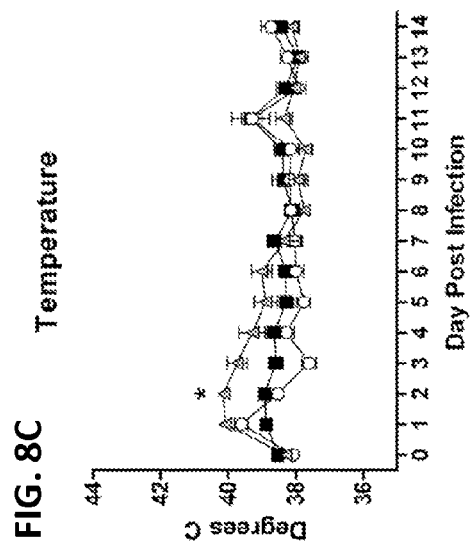
FIG. 8D Relative Sickness

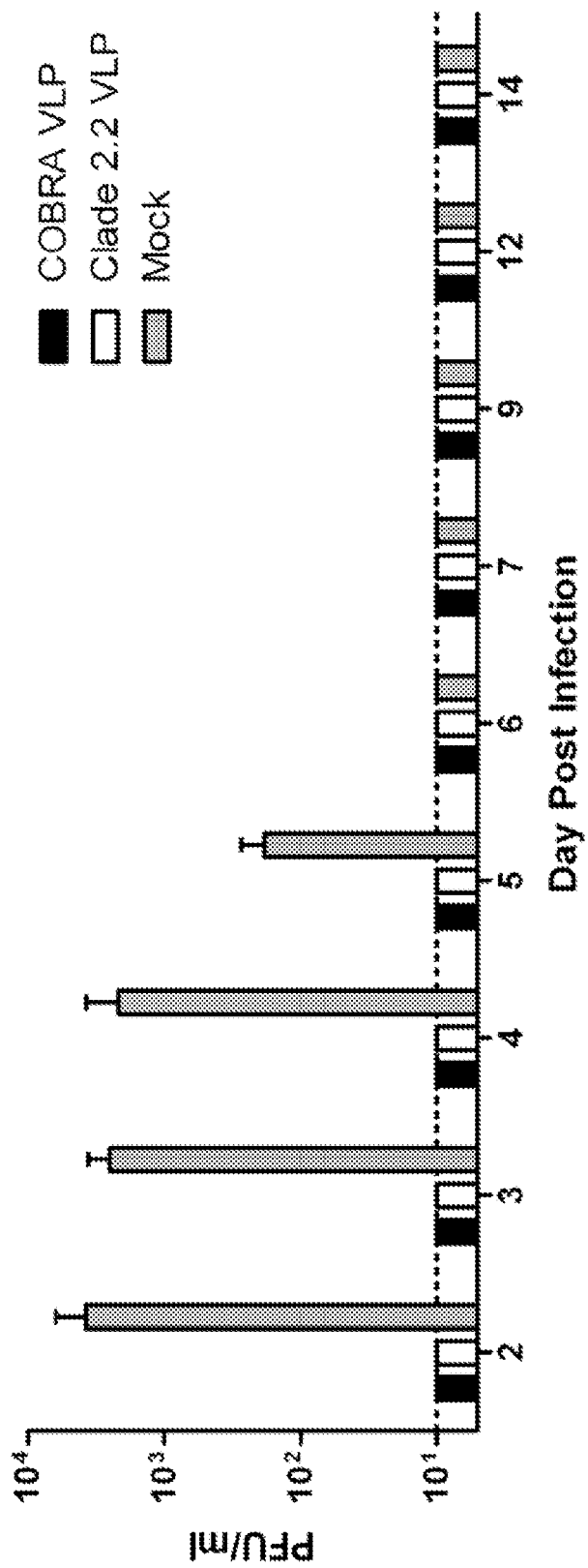

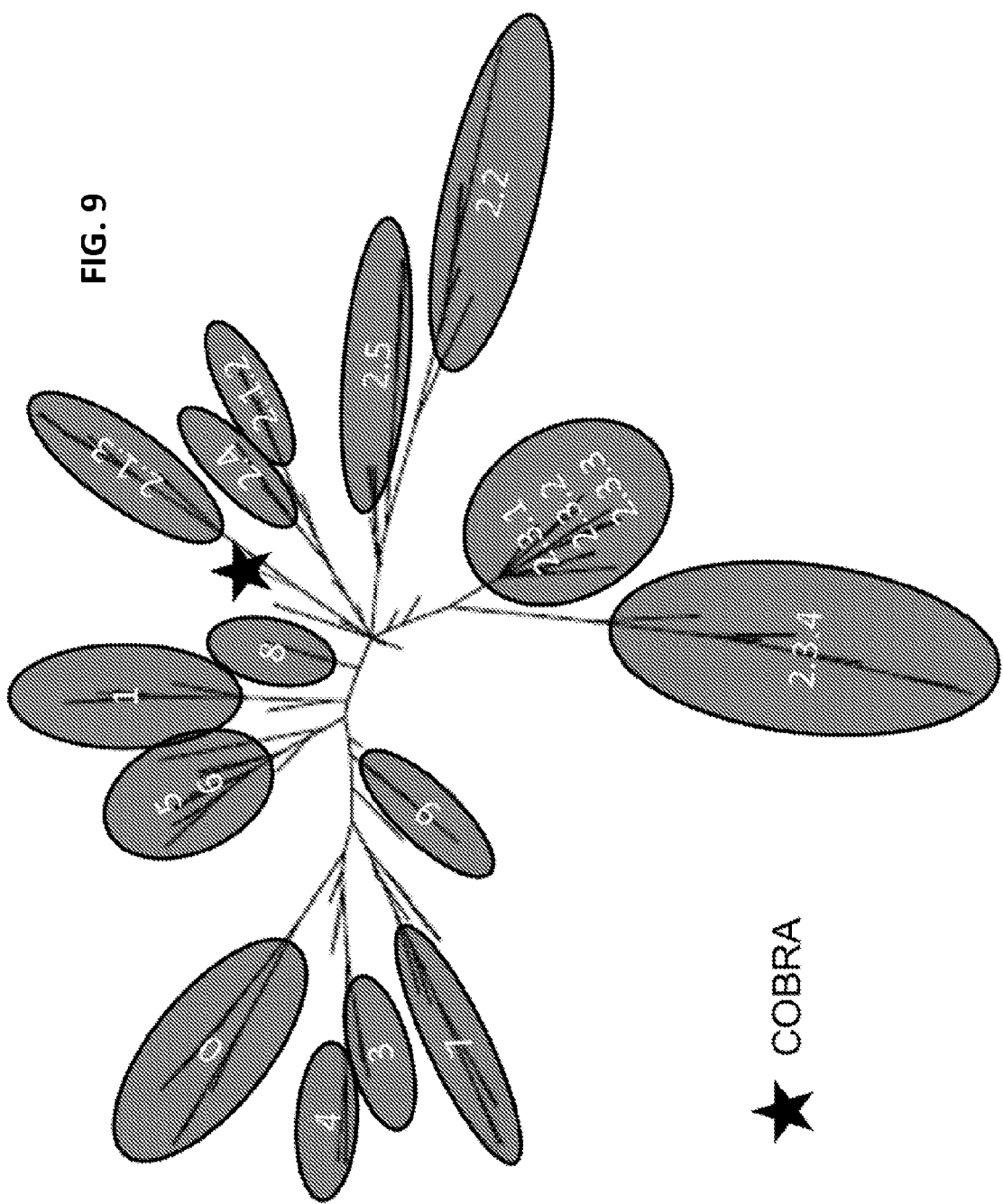

FIG. 10A

Week 3

[Bar chart: End Point Dilution (y-axis, log scale 100-100000) vs HA Coating Antigen (Clade 2.1, Clade 2.2, Clade 2.3). Legend: Whooper Swan VLP (black), COBRA VLP (white), Mock (gray). *p<0.05]

FIG. 10B

Week 6

[Bar chart: End Point Dilution (y-axis, log scale 100-100000) vs HA Coating Antigen (Clade 2.1, Clade 2.2, Clade 2.3). * indicates p<0.05, with asterisk above Clade 2.1 COBRA VLP bar.]

FIG. 11

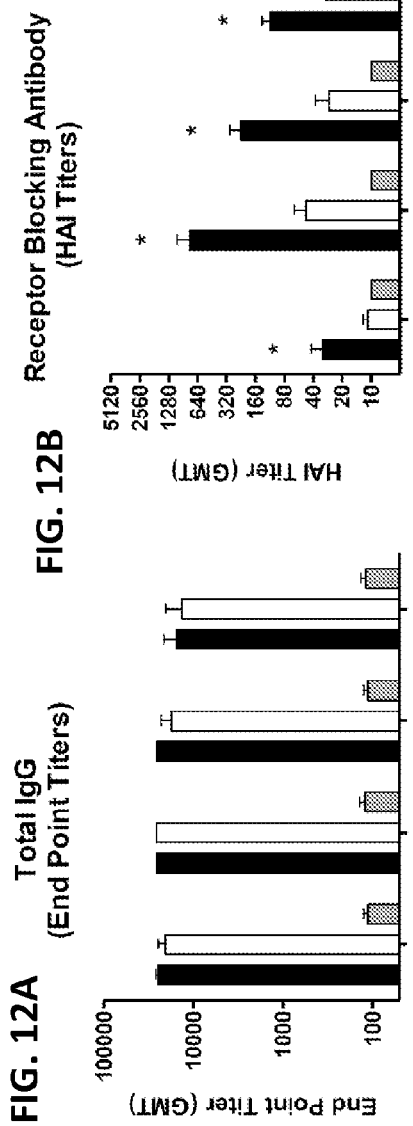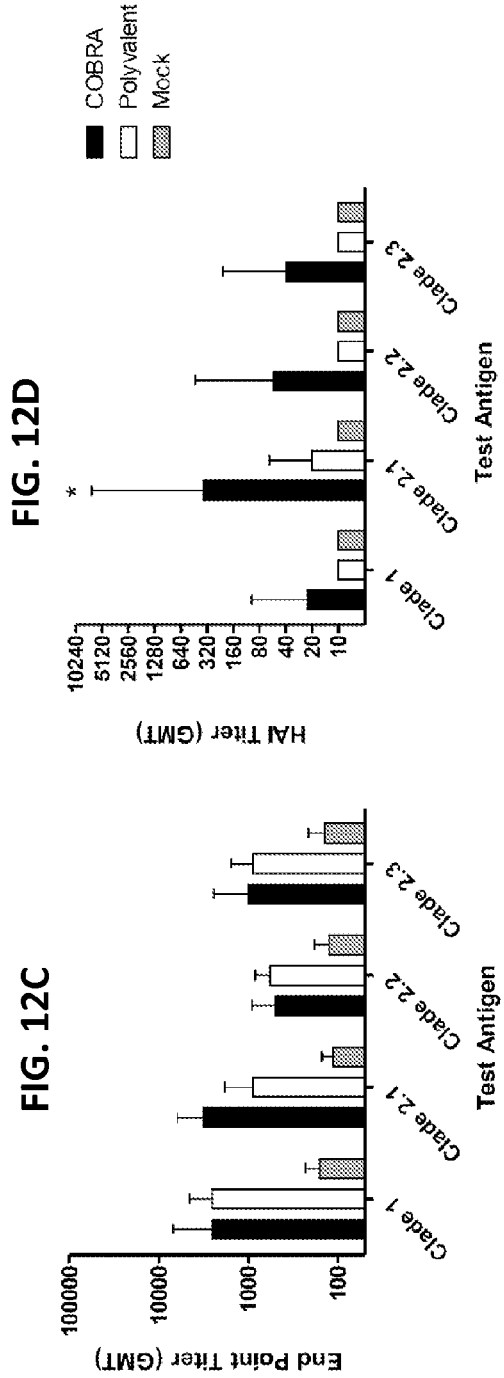

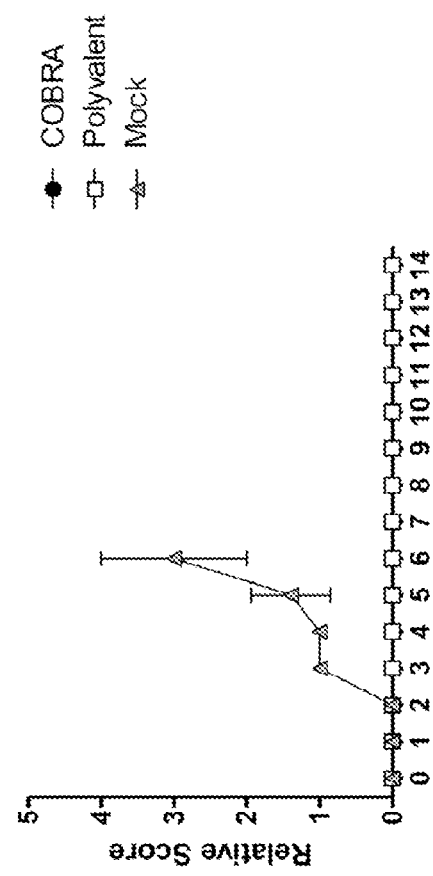
FIG. 13A Weight Loss
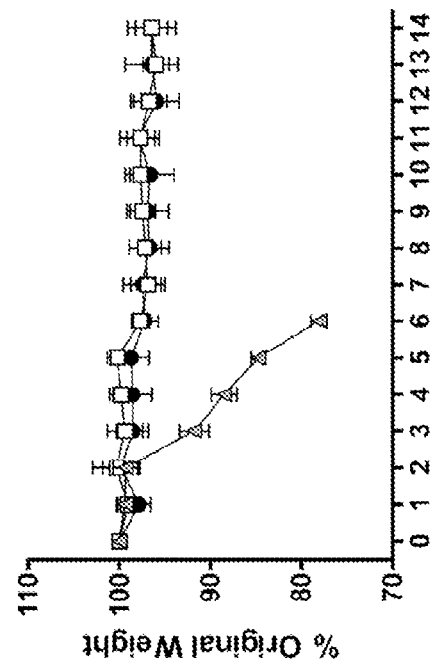
FIG. 13B Sickness
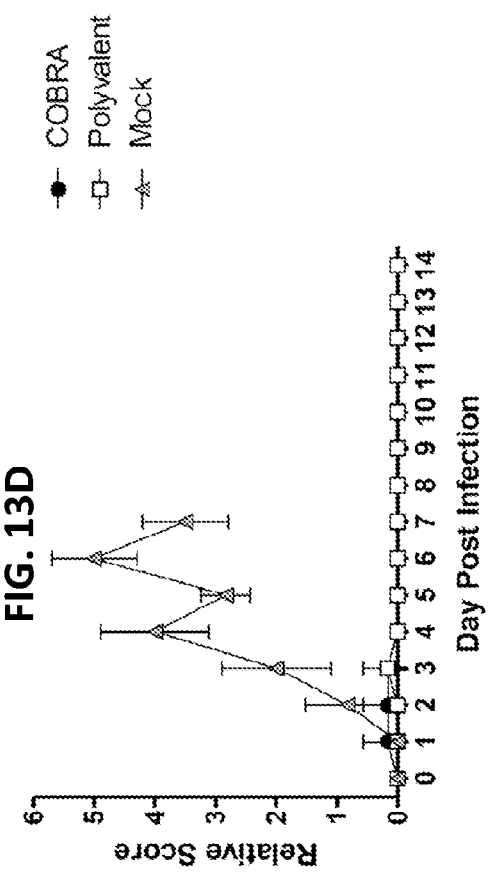
FIG. 13C
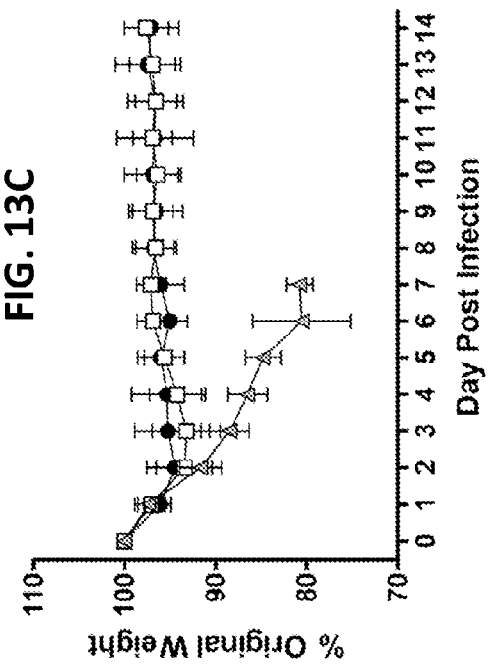
FIG. 13D

FIG. 15A

FIG. 15B
Bronchi

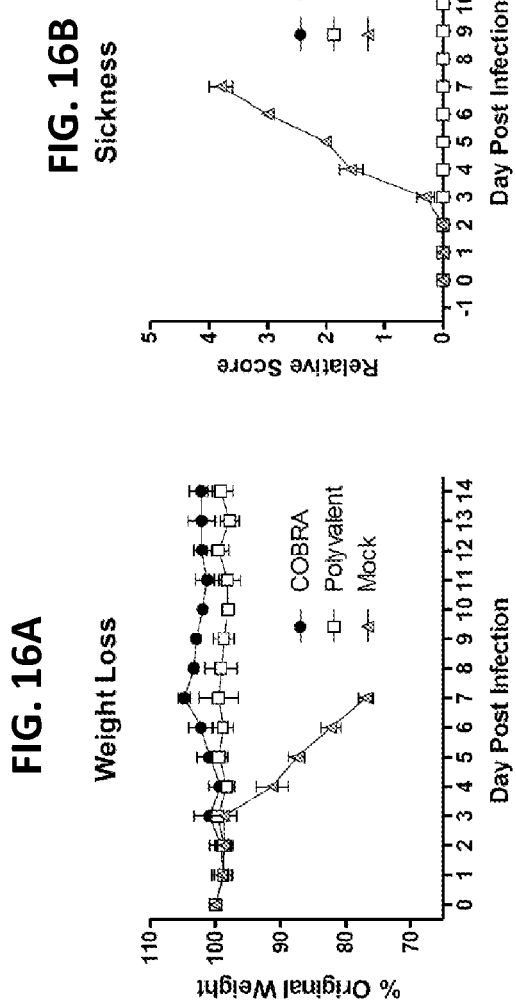
FIG. 16A Weight Loss
FIG. 16B Sickness
FIG. 16C Lung Viral Titers

SEQUENCE LISTING

```
<160> NUMBER OF SEQ ID NOS: 11

<210> SEQ ID NO 1
<211> LENGTH: 1707
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(1707)

<400> SEQUENCE: 1 atg gaa aag atc gtg ctg ctg ctg gct atc gtg agc ctg gtg aag agc        48
Met Glu Lys Ile Val Leu Leu Leu Ala Ile Val Ser Leu Val Lys Ser
1               5                   10                  15 gac cag att tgc atc ggc tac cac gcc aac aac agc acc gag cag gtg        96
Asp Gln Ile Cys Ile Gly Tyr His Ala Asn Asn Ser Thr Glu Gln Val
            20                  25                  30 gac acc atc atg gaa aag aac gtc acc gtg acc cac gcc cag gac atc       144
Asp Thr Ile Met Glu Lys Asn Val Thr Val Thr His Ala Gln Asp Ile
        35                  40                  45 ctg gaa aag acc cac aac ggc aag ctg tgc gac ctg gac ggc gtg aag       192
Leu Glu Lys Thr His Asn Gly Lys Leu Cys Asp Leu Asp Gly Val Lys
    50                  55                  60 ccc ctg atc ctg agg gac tgc agc gtg gcc ggc tgg ctg ctg ggc aac       240
Pro Leu Ile Leu Arg Asp Cys Ser Val Ala Gly Trp Leu Leu Gly Asn
65                  70                  75                  80 ccc atg tgc gac gag ttc atc aac gtg ccc gag tgg agc tac atc gtg       288
Pro Met Cys Asp Glu Phe Ile Asn Val Pro Glu Trp Ser Tyr Ile Val
                85                  90                  95 gag aag gcc aac ccc gcc aac gac ctg tgc tac ccc ggc aac ttc aac       336
Glu Lys Ala Asn Pro Ala Asn Asp Leu Cys Tyr Pro Gly Asn Phe Asn
            100                 105                 110 gac tac gag gaa ctg aag cac ctg ctg tcc agg atc aac cac ttc gag       384
Asp Tyr Glu Glu Leu Lys His Leu Leu Ser Arg Ile Asn His Phe Glu
        115                 120                 125 aag atc cag atc atc ccc aag agc agc tgg tcc gac cac gag gcc agc       432
Lys Ile Gln Ile Ile Pro Lys Ser Ser Trp Ser Asp His Glu Ala Ser
    130                 135                 140 agc ggc gtg agc agc gcc tgc cca tac cag ggc agc ccc agc ttc ttc       480
Ser Gly Val Ser Ser Ala Cys Pro Tyr Gln Gly Ser Pro Ser Phe Phe
145                 150                 155                 160 aga aac gtg gtg tgg ctg atc aag aag aac aac acc tac ccc acc atc       528
Arg Asn Val Val Trp Leu Ile Lys Lys Asn Asn Thr Tyr Pro Thr Ile
                165                 170                 175 aag agg tcc tac aac aac acc aac cag gaa gat ctg ctg gtc ctg tgg       576
Lys Arg Ser Tyr Asn Asn Thr Asn Gln Glu Asp Leu Leu Val Leu Trp
            180                 185                 190 ggc atc cac cac cct aat gac gcc gcc gaa cag acc agg ctg tac cag       624
Gly Ile His His Pro Asn Asp Ala Ala Glu Gln Thr Arg Leu Tyr Gln
        195                 200                 205 aac ccc acc acc tac atc agc gtg ggc aca agc acc ctg aac cag agg       672
Asn Pro Thr Thr Tyr Ile Ser Val Gly Thr Ser Thr Leu Asn Gln Arg
    210                 215                 220 ctg gtg ccc aag atc gcc acc agg tcc aag gtg aac gga cag tcc ggc       720
Leu Val Pro Lys Ile Ala Thr Arg Ser Lys Val Asn Gly Gln Ser Gly
```

|     |     |     |     |     |     |     |     |     |     |     |     |     |     |     |     |      |
| --- | --- | --- | --- | --- | --- | --- | --- | --- | --- | --- | --- | --- | --- | --- | --- | --- |
| 225 |     |     |     |     | 230 |     |     |     |     | 235 |     |     |     |     | 240 |      |
| agg | atg | gaa | ttc | ttc | tgg | acc | atc | ctg | aag | cct | aac | gac | gcc | atc | aac |  768 |
| Arg | Met | Glu | Phe | Phe | Trp | Thr | Ile | Leu | Lys | Pro | Asn | Asp | Ala | Ile | Asn |      |
|     |     |     |     | 245 |     |     |     |     | 250 |     |     |     |     | 255 |     |      |
| ttc | gag | agc | aac | ggc | aac | ttt | atc | gcc | ccc | gag | tac | gcc | tac | aag | atc |  816 |
| Phe | Glu | Ser | Asn | Gly | Asn | Phe | Ile | Ala | Pro | Glu | Tyr | Ala | Tyr | Lys | Ile |      |
|     |     |     |     | 260 |     |     |     |     | 265 |     |     |     |     | 270 |     |      |
| gtg | aag | aag | ggc | gac | agc | gcc | atc | atg | aag | agc | gag | ctg | gaa | tac | ggc |  864 |
| Val | Lys | Lys | Gly | Asp | Ser | Ala | Ile | Met | Lys | Ser | Glu | Leu | Glu | Tyr | Gly |      |
|     |     |     |     | 275 |     |     |     |     | 280 |     |     |     |     | 285 |     |      |
| aac | tgc | aac | acc | aag | tgc | cag | acc | ccc | atc | ggc | gcc | atc | aac | agc | agc |  912 |
| Asn | Cys | Asn | Thr | Lys | Cys | Gln | Thr | Pro | Ile | Gly | Ala | Ile | Asn | Ser | Ser |      |
|     |     |     |     | 290 |     |     |     |     | 295 |     |     |     |     | 300 |     |      |
| atg | ccc | ttc | cac | aac | atc | cac | ccc | ctg | acc | atc | ggc | gag | tgc | ccc | aag |  960 |
| Met | Pro | Phe | His | Asn | Ile | His | Pro | Leu | Thr | Ile | Gly | Glu | Cys | Pro | Lys |      |
| 305 |     |     |     |     | 310 |     |     |     |     | 315 |     |     |     |     | 320 |      |
| tac | gtg | aag | agc | aac | agg | ctg | gtg | ctg | gcc | acc | ggc | ctg | agg | aac | agc | 1008 |
| Tyr | Val | Lys | Ser | Asn | Arg | Leu | Val | Leu | Ala | Thr | Gly | Leu | Arg | Asn | Ser |      |
|     |     |     |     | 325 |     |     |     |     | 330 |     |     |     |     | 335 |     |      |
| ccc | cag | aga | gag | agc | aga | aga | aag | aag | agg | ggc | ctg | ttc | ggc | gct | atc | 1056 |
| Pro | Gln | Arg | Glu | Ser | Arg | Arg | Lys | Lys | Arg | Gly | Leu | Phe | Gly | Ala | Ile |      |
|     |     |     |     | 340 |     |     |     |     | 345 |     |     |     |     | 350 |     |      |
| gcc | ggc | ttc | atc | gag | ggc | ggc | tgg | cag | ggc | atg | gtg | gac | ggg | tgg | tac | 1104 |
| Ala | Gly | Phe | Ile | Glu | Gly | Gly | Trp | Gln | Gly | Met | Val | Asp | Gly | Trp | Tyr |      |
|     |     |     |     | 355 |     |     |     |     | 360 |     |     |     |     | 365 |     |      |
| ggc | tac | cac | cac | tct | aac | gag | cag | ggc | agc | ggc | tac | gcc | gcc | gac | aaa | 1152 |
| Gly | Tyr | His | His | Ser | Asn | Glu | Gln | Gly | Ser | Gly | Tyr | Ala | Ala | Asp | Lys |      |
|     |     |     |     | 370 |     |     |     |     | 375 |     |     |     |     | 380 |     |      |
| gag | agc | acc | cag | aag | gcc | atc | gac | ggc | gtc | acc | aac | aag | gtg | aac | agc | 1200 |
| Glu | Ser | Thr | Gln | Lys | Ala | Ile | Asp | Gly | Val | Thr | Asn | Lys | Val | Asn | Ser |      |
| 385 |     |     |     |     | 390 |     |     |     |     | 395 |     |     |     |     | 400 |      |
| atc | atc | gac | aag | atg | aac | acc | cag | ttc | gag | gcc | gtg | ggc | aga | gag | ttc | 1248 |
| Ile | Ile | Asp | Lys | Met | Asn | Thr | Gln | Phe | Glu | Ala | Val | Gly | Arg | Glu | Phe |      |
|     |     |     |     | 405 |     |     |     |     | 410 |     |     |     |     | 415 |     |      |
| aac | aac | ctg | gaa | agg | cgg | atc | gag | aac | ctg | aac | aag | aaa | atg | gaa | gat | 1296 |
| Asn | Asn | Leu | Glu | Arg | Arg | Ile | Glu | Asn | Leu | Asn | Lys | Lys | Met | Glu | Asp |      |
|     |     |     |     | 420 |     |     |     |     | 425 |     |     |     |     | 430 |     |      |
| ggc | ttc | ctg | gac | gtg | tgg | acc | tac | aac | gcc | gag | ctg | ctg | gtg | ctg | atg | 1344 |
| Gly | Phe | Leu | Asp | Val | Trp | Thr | Tyr | Asn | Ala | Glu | Leu | Leu | Val | Leu | Met |      |
|     |     |     |     | 435 |     |     |     |     | 440 |     |     |     |     | 445 |     |      |
| gaa | aac | gag | agg | acc | ctg | gac | ttc | cac | gac | agc | aac | gtg | aag | aac | ctg | 1392 |
| Glu | Asn | Glu | Arg | Thr | Leu | Asp | Phe | His | Asp | Ser | Asn | Val | Lys | Asn | Leu |      |
|     |     |     |     | 450 |     |     |     |     | 455 |     |     |     |     | 460 |     |      |
| tac | gac | aaa | gtg | cgg | ctg | cag | ctg | agg | gac | aac | gcc | aaa | gag | ctg | ggc | 1440 |
| Tyr | Asp | Lys | Val | Arg | Leu | Gln | Leu | Arg | Asp | Asn | Ala | Lys | Glu | Leu | Gly |      |
| 465 |     |     |     |     | 470 |     |     |     |     | 475 |     |     |     |     | 480 |      |
| aac | ggc | tgc | ttc | gag | ttc | tac | cac | aag | tgc | gac | aac | gag | tgc | atg | gaa | 1488 |
| Asn | Gly | Cys | Phe | Glu | Phe | Tyr | His | Lys | Cys | Asp | Asn | Glu | Cys | Met | Glu |      |
|     |     |     |     | 485 |     |     |     |     | 490 |     |     |     |     | 495 |     |      |
| agc | gtg | agg | aac | ggc | acc | tac | gac | tac | ccc | cag | tac | agc | gag | gaa | gcc | 1536 |
| Ser | Val | Arg | Asn | Gly | Thr | Tyr | Asp | Tyr | Pro | Gln | Tyr | Ser | Glu | Glu | Ala |      |
|     |     |     |     | 500 |     |     |     |     | 505 |     |     |     |     | 510 |     |      |
| agg | ctg | aag | agg | gaa | gag | atc | agc | gga | gtg | aag | ctg | gaa | agc | atc | ggc | 1584 |
| Arg | Leu | Lys | Arg | Glu | Glu | Ile | Ser | Gly | Val | Lys | Leu | Glu | Ser | Ile | Gly |      |
|     |     |     |     | 515 |     |     |     |     | 520 |     |     |     |     | 525 |     |      |
| acc | tac | cag | atc | ctg | agc | atc | tac | agc | acc | gtc | gcc | agc | agc | ctg | gcc | 1632 |
| Thr | Tyr | Gln | Ile | Leu | Ser | Ile | Tyr | Ser | Thr | Val | Ala | Ser | Ser | Leu | Ala |      |
|     |     |     |     | 530 |     |     |     |     | 535 |     |     |     |     | 540 |     |      |
| ctg | gct | atc | atg | gtg | gcc | gga | ctg | agc | ctg | tgg | atg | tgc | agc | aac | ggc | 1680 |

```
Leu Ala Ile Met Val Ala Gly Leu Ser Leu Trp Met Cys Ser Asn Gly
545                 550                 555                 560 agc ctg cag tgc agg atc tgc atc tga                                1707
Ser Leu Gln Cys Arg Ile Cys Ile
                565
```

<210> SEQ ID NO 2
<211> LENGTH: 568
<212> TYPE: PRT
<213> ORGANISM: Artificial Sequence
<220> FEATURE:
<223> OTHER INFORMATION: Synthetic Construct

<400> SEQUENCE: 2

```
Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
                20                  25                  30

Asp Thr Ile Met Glu Lys Asn Val Thr Val Thr His Ala Gln Asp Ile
            35                  40                  45

Leu Glu Lys Thr His Asn Gly Lys Leu Cys Asp Leu Asp Gly Val Lys
50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
130                 135                 140

Ser Gly Val Ser Ser Ala Cys Pro Tyr Gln Gly Ser Pro Ser Phe Phe
145                 150                 155                 160

Arg Asn Val Val Trp Leu Ile Lys Lys Asn Asn Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Ile Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335
```

```
Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 3
<211> LENGTH: 1350
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(1350)

<400> SEQUENCE: 3 atg aat cct aat aag aag atc atc aca atc gga agc atc tgc atg gtg     48
Met Asn Pro Asn Lys Lys Ile Ile Thr Ile Gly Ser Ile Cys Met Val
1               5                   10                  15 aca gga atg gtg agc ctg atg ctg cag atc gga aat ctg atc agc atc     96
Thr Gly Met Val Ser Leu Met Leu Gln Ile Gly Asn Leu Ile Ser Ile
            20                  25                  30 tgg gtg agc cac agc atc cac aca gga aat cag cac aag gcc gag cct    144
Trp Val Ser His Ser Ile His Thr Gly Asn Gln His Lys Ala Glu Pro
        35                  40                  45 atc agc aat aca aat ttt ctg aca gag aag gcc gtg gcc agc gtg aag    192
Ile Ser Asn Thr Asn Phe Leu Thr Glu Lys Ala Val Ala Ser Val Lys
    50                  55                  60 ctg gcc gga aat agc agc ctg tgc cct atc aat gga tgg gcc gtg tac    240
Leu Ala Gly Asn Ser Ser Leu Cys Pro Ile Asn Gly Trp Ala Val Tyr
65                  70                  75                  80
```

```
                                                                -continued agc aag gat aat agc atc aga atc gga agc aag gga gat gtg ttt gtg    288
Ser Lys Asp Asn Ser Ile Arg Ile Gly Ser Lys Gly Asp Val Phe Val
             85                  90                  95 atc aga gag cct ttt atc agc tgc agc cac ctg gag tgc aga aca ttt    336
Ile Arg Glu Pro Phe Ile Ser Cys Ser His Leu Glu Cys Arg Thr Phe
        100                 105                 110 ttt ctg aca cag gga gcc ctg ctg aat gat aag cac agc aat gga aca    384
Phe Leu Thr Gln Gly Ala Leu Leu Asn Asp Lys His Ser Asn Gly Thr
        115                 120                 125 gtg aag gat aga agc cct cac aga aca ctg atg agc tgc cct gtg gga    432
Val Lys Asp Arg Ser Pro His Arg Thr Leu Met Ser Cys Pro Val Gly
    130                 135                 140 gag gcc cct agc cct tac aat agc aga ttt gag agc gtg gcc tgg agc    480
Glu Ala Pro Ser Pro Tyr Asn Ser Arg Phe Glu Ser Val Ala Trp Ser
145                 150                 155                 160 gcc agc gcc tgc cac gat gga aca agc tgg ctg aca atc gga atc agc    528
Ala Ser Ala Cys His Asp Gly Thr Ser Trp Leu Thr Ile Gly Ile Ser
                165                 170                 175 gga cct gat aat gga gcc gtg gcc gtg ctg aag tac aat gga atc atc    576
Gly Pro Asp Asn Gly Ala Val Ala Val Leu Lys Tyr Asn Gly Ile Ile
            180                 185                 190 aca gat aca atc aag agc tgg aga aat aat atc ctg aga aca cag gag    624
Thr Asp Thr Ile Lys Ser Trp Arg Asn Asn Ile Leu Arg Thr Gln Glu
        195                 200                 205 agc gag tgc gcc tgc gtg aat gga agc tgc ttt aca gtg atg aca gat    672
Ser Glu Cys Ala Cys Val Asn Gly Ser Cys Phe Thr Val Met Thr Asp
        210                 215                 220 gga cct agc aat gga cag gcc agc cac aag atc ttt aag atg gag aag    720
Gly Pro Ser Asn Gly Gln Ala Ser His Lys Ile Phe Lys Met Glu Lys
225                 230                 235                 240 gga aag gtg gtg aag agc gtg gag ctg gat gcc cct aat tac cac tac    768
Gly Lys Val Val Lys Ser Val Glu Leu Asp Ala Pro Asn Tyr His Tyr
                245                 250                 255 gag gag tgc agc tgc tac cct gat gcc gga gag atc aca tgc gtg tgc    816
Glu Glu Cys Ser Cys Tyr Pro Asp Ala Gly Glu Ile Thr Cys Val Cys
            260                 265                 270 aga gat aat tgg cac gga agc aat aga cct tgg gtg agc ttt aat cag    864
Arg Asp Asn Trp His Gly Ser Asn Arg Pro Trp Val Ser Phe Asn Gln
        275                 280                 285 aat ctg gag tac cag atc gga tac atc tgc agc gga gtg ttt gga gat    912
Asn Leu Glu Tyr Gln Ile Gly Tyr Ile Cys Ser Gly Val Phe Gly Asp
        290                 295                 300 aat cct aga cct aat gat gga aca gga agc tgc gga cct gtg agc agc    960
Asn Pro Arg Pro Asn Asp Gly Thr Gly Ser Cys Gly Pro Val Ser Ser
305                 310                 315                 320 aat gga gcc tac gga gtg aag gga ttt agc ttt aag tac gga aat gga   1008
Asn Gly Ala Tyr Gly Val Lys Gly Phe Ser Phe Lys Tyr Gly Asn Gly
                325                 330                 335 gtg tgg atc gga aga aca aag agc aca aat agc aga agc gga ttt gag   1056
Val Trp Ile Gly Arg Thr Lys Ser Thr Asn Ser Arg Ser Gly Phe Glu
            340                 345                 350 atg atc tgg gac cct aat gga tgg aca gag aca gat agc agc ttt agc   1104
Met Ile Trp Asp Pro Asn Gly Trp Thr Glu Thr Asp Ser Ser Phe Ser
        355                 360                 365 gtg aag cag gat atc gtg gcc atc aca gat tgg agc gga tac agc gga   1152
Val Lys Gln Asp Ile Val Ala Ile Thr Asp Trp Ser Gly Tyr Ser Gly
        370                 375                 380 agc ttt gtg cag cac cct gag ctg aca gga ctg gat tgc atc aga cct   1200
Ser Phe Val Gln His Pro Glu Leu Thr Gly Leu Asp Cys Ile Arg Pro
385                 390                 395                 400
```

```
tgc ttt tgg gtg gag ctg atc aga gga aga cct aag gag agc aca atc      1248
Cys Phe Trp Val Glu Leu Ile Arg Gly Arg Pro Lys Glu Ser Thr Ile
            405                 410                 415 tgg aca agc gga agc agc atc agc ttt tgc gga gtg aat agc gat aca      1296
Trp Thr Ser Gly Ser Ser Ile Ser Phe Cys Gly Val Asn Ser Asp Thr
        420                 425                 430 gtg gga tgg agc tgg cct gat gga gcc gag ctg cct ttt aca atc gat      1344
Val Gly Trp Ser Trp Pro Asp Gly Ala Glu Leu Pro Phe Thr Ile Asp
        435                 440                 445 aag tga                                                              1350
Lys

<210> SEQ ID NO 4
<211> LENGTH: 449
<212> TYPE: PRT
<213> ORGANISM: Artificial Sequence
<220> FEATURE:
<223> OTHER INFORMATION: Synthetic Construct

<400> SEQUENCE: 4

Met Asn Pro Asn Lys Lys Ile Ile Thr Ile Gly Ser Ile Cys Met Val
1               5                   10                  15

Thr Gly Met Val Ser Leu Met Leu Gln Ile Gly Asn Leu Ile Ser Ile
            20                  25                  30

Trp Val Ser His Ser Ile His Thr Gly Asn Gln His Lys Ala Glu Pro
        35                  40                  45

Ile Ser Asn Thr Asn Phe Leu Thr Glu Lys Ala Val Ala Ser Val Lys
    50                  55                  60

Leu Ala Gly Asn Ser Ser Leu Cys Pro Ile Asn Gly Trp Ala Val Tyr
65                  70                  75                  80

Ser Lys Asp Asn Ser Ile Arg Ile Gly Ser Lys Gly Asp Val Phe Val
                85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
    130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Asn Gly Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
    210                 215                 220

Gly Pro Ser Asn Gly Gln Ala Ser His Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asp Ala Gly Glu Ile Thr Cys Val Cys
            260                 265                 270

Arg Asp Asn Trp His Gly Ser Asn Arg Pro Trp Val Ser Phe Asn Gln
        275                 280                 285
```

-continued

```
Asn Leu Glu Tyr Gln Ile Gly Tyr Ile Cys Ser Gly Val Phe Gly Asp
    290                 295                 300

Asn Pro Arg Pro Asn Asp Gly Thr Gly Ser Cys Gly Pro Val Ser Ser
305                 310                 315                 320

Asn Gly Ala Tyr Gly Val Lys Gly Phe Ser Phe Lys Tyr Gly Asn Gly
                325                 330                 335

Val Trp Ile Gly Arg Thr Lys Ser Thr Asn Ser Arg Ser Gly Phe Glu
            340                 345                 350

Met Ile Trp Asp Pro Asn Gly Trp Thr Glu Thr Asp Ser Ser Phe Ser
        355                 360                 365

Val Lys Gln Asp Ile Val Ala Ile Thr Asp Trp Ser Gly Tyr Ser Gly
    370                 375                 380

Ser Phe Val Gln His Pro Glu Leu Thr Gly Leu Asp Cys Ile Arg Pro
385                 390                 395                 400

Cys Phe Trp Val Glu Leu Ile Arg Gly Arg Pro Lys Glu Ser Thr Ile
                405                 410                 415

Trp Thr Ser Gly Ser Ser Ile Ser Phe Cys Gly Val Asn Ser Asp Thr
            420                 425                 430

Val Gly Trp Ser Trp Pro Asp Gly Ala Glu Leu Pro Phe Thr Ile Asp
        435                 440                 445

Lys
```

<210> SEQ ID NO 5
<211> LENGTH: 759
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(759)

<400> SEQUENCE: 5

```
atg agc ctg ctg acc gag gtg gag aca tac gtg ctg tcc atc atc ccc      48
Met Ser Leu Leu Thr Glu Val Glu Thr Tyr Val Leu Ser Ile Ile Pro
1               5                   10                  15 agc ggc cct ctg aag gcc gag atc gcc cag aga ctg gaa gat gtg ttc      96
Ser Gly Pro Leu Lys Ala Glu Ile Ala Gln Arg Leu Glu Asp Val Phe
            20                  25                  30 gcc ggc aag aac acc gac ctg gaa gtg ctg atg gaa tgg ctg aaa acc     144
Ala Gly Lys Asn Thr Asp Leu Glu Val Leu Met Glu Trp Leu Lys Thr
        35                  40                  45 aga ccc atc ctg agc cct ctg acc aag ggc atc ctg ggc ttc gtg ttc     192
Arg Pro Ile Leu Ser Pro Leu Thr Lys Gly Ile Leu Gly Phe Val Phe
    50                  55                  60 acc ctg acc gtg ccc agc gag aga ggc ctg cag agg cgg aga ttc gtg     240
Thr Leu Thr Val Pro Ser Glu Arg Gly Leu Gln Arg Arg Arg Phe Val
65                  70                  75                  80 cag aac gcc ctg aac ggc aac ggc gac ccc aac aac atg gac aag gcc     288
Gln Asn Ala Leu Asn Gly Asn Gly Asp Pro Asn Asn Met Asp Lys Ala
                85                  90                  95 gtg aag ctg tac aga aag ctg aag cgg gag atc acc ttc cac ggc gcc     336
Val Lys Leu Tyr Arg Lys Leu Lys Arg Glu Ile Thr Phe His Gly Ala
            100                 105                 110 aaa gag atc agc ctg agc tac agc gct ggc gcc ctg gcc agc tgc atg     384
Lys Glu Ile Ser Leu Ser Tyr Ser Ala Gly Ala Leu Ala Ser Cys Met
        115                 120                 125 ggc ctg atc tac aac aga atg ggc gcc gtg acc acc gag gtg gcc ttc     432
```

```
Gly Leu Ile Tyr Asn Arg Met Gly Ala Val Thr Thr Glu Val Ala Phe
        130                 135                 140 ggc ctg gtc tgc gcc acc tgc gag cag atc gcc gac agc cag cac aga     480
Gly Leu Val Cys Ala Thr Cys Glu Gln Ile Ala Asp Ser Gln His Arg
145                 150                 155                 160 tcc cac aga cag atg gtc acc acc aac ccc ctg atc aga cac gag         528
Ser His Arg Gln Met Val Thr Thr Asn Pro Leu Ile Arg His Glu
                165                 170                 175 aac aga atg gtg ctg gcc tct acc acc gcc aag gcc atg gaa cag atg     576
Asn Arg Met Val Leu Ala Ser Thr Thr Ala Lys Ala Met Glu Gln Met
            180                 185                 190 gcc ggc agc agc gag cag gcc gcc gag gct atg gaa gtc gcc tct cag     624
Ala Gly Ser Ser Glu Gln Ala Ala Glu Ala Met Glu Val Ala Ser Gln
        195                 200                 205 gct agg cag atg gtc cag gcc atg aga acc atc ggc acc cac ccc agc     672
Ala Arg Gln Met Val Gln Ala Met Arg Thr Ile Gly Thr His Pro Ser
    210                 215                 220 agc tct gct ggc ctg aag aac gac ctg ctg gaa aac ctg cag gcc tac     720
Ser Ser Ala Gly Leu Lys Asn Asp Leu Leu Glu Asn Leu Gln Ala Tyr
225                 230                 235                 240 cag aaa aga atg ggc gtc cag atg cag aga ttc aag tga                 759
Gln Lys Arg Met Gly Val Gln Met Gln Arg Phe Lys
                245                 250

<210> SEQ ID NO 6
<211> LENGTH: 252
<212> TYPE: PRT
<213> ORGANISM: Artificial Sequence
<220> FEATURE:
<223> OTHER INFORMATION: Synthetic Construct

<400> SEQUENCE: 6

Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Val Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ser Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205
```

```
Ala Arg Gln Met Val Gln Ala Met Arg Thr Ile Gly Thr His Pro Ser
    210                 215                 220

Ser Ser Ala Gly Leu Lys Asn Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 7
<211> LENGTH: 5511
<212> TYPE: DNA
<213> ORGANISM: Artificial Sequence
<220> FEATURE:
<223> OTHER INFORMATION: Synthetic construct

<400> SEQUENCE: 7
```

| | | | | | |
|---|---|---|---|---|---|
| cgacaatatt | ggctattggc | cattgcatac | gttgtatcta | tcataata | tgtacattta | 60 |
| tattggctca | tgtccaatat | gaccgccatg | ttgacattga | ttattgacta | gttattaata | 120 |
| gtaatcaatt | acggggtcat | tagttcatag | cccatatatg | gagttccgcg | ttacataact | 180 |
| tacggtaaat | ggcccgcctc | gtgaccgccc | aacgacccc | gcccattgac | gtcaataatg | 240 |
| acgtatgttc | ccatagtaac | gccaataggg | actttccatt | gacgtcaatg | ggtggagtat | 300 |
| ttacggtaaa | ctgcccactt | ggcagtacat | caagtgtatc | atatgccaag | tccgccccta | 360 |
| tgacgtcaa | tgacggtaaa | tggcccgcct | ggcattatgc | ccagtacatg | accttacggg | 420 |
| actttcctac | ttggcagtac | atctacgtat | tagtcatcgc | tattaccatg | gtgatgcggt | 480 |
| tttggcagta | caccaatggg | cgtggatagc | ggtttgactc | acggggattt | ccaagtctcc | 540 |
| accccattga | cgtcaatggg | agtttgtttt | ggcaccaaaa | tcaacgggac | tttccaaaat | 600 |
| gtcgtaataa | ccccgccccg | ttgacgcaaa | tgggcggtag | gcgtgtacgg | tgggaggtct | 660 |
| atataagcag | agctcgttta | gtgaaccgtc | agatcgcctg | gagacgccat | ccacgctgtt | 720 |
| ttgacctcca | tagaagacac | cgggaccgat | ccagcctccg | cggccgggaa | cggtgcattg | 780 |
| gaacgcggat | tccccgtgcc | aagagtgacg | taagtaccgc | ctatagactc | tataggcaca | 840 |
| cccctttggc | tcttatgcat | gctatactgt | ttttggcttg | gggcctatac | accccccgctc | 900 |
| cttatgctat | aggtgatggt | atagcttagc | ctataggtgt | gggttattga | ccattattga | 960 |
| ccactcccct | attggtgacg | atactttcca | ttactaatcc | ataacatggc | tctttgccac | 1020 |
| aactatctct | attggctata | tgccaatact | ctgtccttca | gagactgaca | cggactctgt | 1080 |
| attttacag | gatggggtcc | catttattat | ttacaaattc | acatatacaa | caacgccgtc | 1140 |
| ccccgtgccc | gcagttttta | ttaaacatag | cgtgggatct | ccacgcgaat | ctcgggtacg | 1200 |
| tgttccggac | atgggctctt | ctccggtagc | ggcggagctt | ccacatccga | gccctggtcc | 1260 |
| catgcctcca | gcggctcatg | gtcgctcggc | agctccttgc | tcctaacagt | ggaggccaga | 1320 |
| cttaggcaca | gcacaatgcc | caccaccacc | agtgtgccgc | acaaggccgt | ggcggtaggg | 1380 |
| tatgtgtctg | aaaatgagct | cggagattgg | gctcgcaccg | tgacgcagat | ggaagactta | 1440 |
| aggcagcggc | agaagaagat | gcaggcagct | gagttgttgt | attctgataa | gagtcagagg | 1500 |
| taactcccgt | tgcggtgctg | ttaacggtgg | agggcagtgt | agtctgagca | gtactcgttg | 1560 |
| ctgccgcgcg | cgccaccaga | cataatagct | gacagactaa | cagactgttc | ctttccatgg | 1620 |
| gtcttttctg | cagtcaccgt | ccaagcttat | ggaaaagatc | gtgctgctgc | tggctatcgt | 1680 |
| gagcctggta | aagagcgacc | agatttgcat | cggctaccac | gccaacaaca | gcaccgagca | 1740 |
| ggtggacacc | atcatggaaa | agaacgtcac | cgtgacccac | gcccaggaca | tcctggaaaa | 1800 |

```
gacccacaac ggcaagctgt gcgacctgga cggcgtgaag ccctgatcc tgagggactg    1860 cagcgtggcc ggctggctgc tgggcaaccc catgtgcgac gagttcatca acgtgcccga    1920
gtggagctac atcgtggaga aggccaaccc cgccaacgac ctgtgctacc ccggcaactt    1980
caacgactac gaggaactga agcacctgct gtccaggatc aaccacttcg agaagatcca    2040
gatcatcccc aagagcagct ggtccgacca cgaggccagc agcggcgtga gcagcgcctg    2100
cccataccag ggcagcccca gcttcttcag aaacgtggtg tggctgatca agaagaacaa    2160
cacctacccc accatcaaga ggtcctacaa caacaccaac caggaagatc tgctggtcct    2220
gtggggcatc caccccccta tgacgccgc cgaacagacc aggctgtacc agaaccccac    2280
cacctacatc agcgtgggca caagcaccct gaaccagagg ctggtgccca agatcgccac    2340
caggtccaag gtgaacggac agtccggcag gatggaattc ttctggacca tcctgaagcc    2400
taacgacgcc atcaacttcg agagcaacgg caactttatc gcccccgagt acgcctacaa    2460
gatcgtgaag aagggcgaca cgccatcat gaagagcgag ctggaatacg caactgcaa    2520 caccaagtgc cagaccccca tcggcgccat caacagcagc atgcccttcc acaacatcca    2580 cccctgacc atcggcgagt gccccaagta cgtgaagagc aacaggctgg tgctggccac    2640
cggcctgagg aacagccccc agagagagag cagaagaaag aagaggggcc tgttcggcgc    2700
tatcgccggc ttcatcgagg gcggctggca gggcatggtg gacgggtggt acggctacca    2760
ccactctaac gagcagggca gcggctacgc cgccgacaaa gagagcaccc agaaggccat    2820
cgacggcgtc accaacaagg tgaacagcat catcgacaag atgaacaccc agttcgaggc    2880
cgtgggcaga gagttcaaca acctggaaag gcggatcgag aacctgaaca gaaaatgga    2940 agatggcttc ctggacgtgt ggacctacaa cgccgagctg ctggtgctga tggaaaacga    3000
gaggaccctg gacttccacg acagcaacgt gaagaacctg tacgacaaag tgcggctgca    3060
gctgagggac aacgccaaag agctgggcaa cggctgcttc gagttctacc acaagtgcga    3120
caacgagtgc atggaaagcg tgaggaacgg cacctacgac taccccagt acagcgagga    3180 agccaggctg aagagggaag agatcagcgg agtgaagctg gaaagcatcg gcacctacca    3240
gatcctgagc atctacagca ccgtcgccag cagcctggcc ctggctatca tggtggccgg    3300
actgagcctg tggatgtgca gcaacggcag cctgcagtgc aggatctgca tcggatcctc    3360
gcaatcccta gggctgtgcc ttctagttgc agccaaact gttgtttgcc ctcccccgt    3420 gccttccttg accctggaag gtgccactcc cactgtcctt tcctaataaa atgaggaaat    3480
tgcatcgcat tgtctgagta ggtgtcattc tattctgggg gtgggtgg ggcaggacag    3540 caagggggag gattgggaag acaatagcag gcatgctggg gatgcggtgg gctctatgtt    3600
cagaacgctc ggttgccgcc gggcgttttt tatctagagt cgacaaattc agaagaactc    3660
gtcaagaagg cgatagaagg cgatgcgctg cgaatcggga gcggcgatac cgtaaagcac    3720
gaggaagcgg tcagcccatt cgccgccaag ctcttcagca atatcacggg tagccaacgc    3780
tatgtcctga tagcggtccg ccacacccag ccggccacag tcgatgaatc cagaaaagcg    3840
gccattttcc accatgatat cggcaagca ggcatcgcca tgggtcacga cgagatcctc    3900
gccgtcgggc atgctcgcct tgagcctggc gaacagttcg gctggcgcga gcccctgatg    3960
ctcttcgtcc agatcatcct gatcgacaag accggcttcc atccgagtac gtgctcgctc    4020
gatgcgatgt ttcgcttggt ggtcgaatgg gcaggtagcc ggatcaagcg tatgcagccg    4080
ccgcattgca tcagccatga tggatacttt ctcggcagga gcaaggtgag atgacaggag    4140
```

-continued

| | |
|---|---|
| atcctgcccc ggcacttcgc ccaatagcag ccagtcccett cccgcttcag tgacaacgtc | 4200 |
| gagcacagct gcgcaaggaa cgcccgtcgt ggccagccac gatagccgcg ctgcctcgtc | 4260 |
| ttgcagttca ttcagggcac cggacaggtc ggtcttgaca aaaagaaccg ggcgcccctg | 4320 |
| cgctgacagc cggaacacgg cggcatcaga gcagccgatt gtctgttgtg cccagtcata | 4380 |
| gccgaatagc ctctccaccc aagcggccgg agaacctgcg tgcaatccat cttgttcaat | 4440 |
| catgcgaaac gatcctcatc ctgtctcttg atcagatctt gatccctgc gccatcagat | 4500 |
| ccttggcggc gagaaagcca tccagtttac tttgcagggc ttcccaacct taccagaggg | 4560 |
| cgccccagct ggcaattccg gttcgcttgc tgtccataaa accgcccagt ctagctatcg | 4620 |
| ccatgtaagc ccactgcaag ctacctgctt tctctttgcg cttgcgtttt cccttgtcca | 4680 |
| gatagcccag tagctgacat tcatccgggg tcagcaccgt ttctgcggac tggctttcta | 4740 |
| cgtgaaaagg atctaggtga agatcctttt tgataatctc atgaccaaaa tcccttaacg | 4800 |
| tgagttttcg ttccactgag cgtcagaccc cgtagaaaag atcaaggat cttcttgaga | 4860 |
| tcctttttt ctgcgcgtaa tctgctgctt gcaaacaaaa aaaccaccgc taccagcggt | 4920 |
| ggtttgtttg ccggatcaag agctaccaac tctttttccg aaggtaactg gcttcagcag | 4980 |
| agcgcagata ccaaatactg tccttctagt gtagccgtag ttaggccacc acttcaagaa | 5040 |
| ctctgtagca ccgcctacat acctcgctct gctaatcctg ttaccagtgg ctgctgccag | 5100 |
| tggcgataag tcgtgtctta ccgggttgga ctcaagacga tagttaccgg ataaggcgca | 5160 |
| gcggtcgggc tgaacggggg gttcgtgcac acagcccagc ttggagcgaa cgacctacac | 5220 |
| cgaactgaga tacctacagc gtgagctatg agaaagcgcc acgcttcccg aagggagaaa | 5280 |
| ggcggacagg tatccggtaa gcggcagggt cggaacagga gagcgcacga gggagcttcc | 5340 |
| agggggaaac gcctggtatc tttatagtcc tgtcgggttt cgccacctct gacttgagcg | 5400 |
| tcgatttttg tgatgctcgt caggggggcg gagcctatgg aaaaacgcca gcaacgcggc | 5460 |
| cttttacgg ttcctgggct tttgctggcc ttttgctcac atgttgtcga c | 5511 |

<210> SEQ ID NO 8
<211> LENGTH: 5769
<212> TYPE: DNA
<213> ORGANISM: Artificial Sequence
<220> FEATURE:
<223> OTHER INFORMATION: Synthetic construct

<400> SEQUENCE: 8

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgacccccg cccattgacg tcaataatga cgtatgttcc | 480 |
| catagtaacg ccaataggga cttteccattg acgtcaatgg gtggagtatt tacggtaaac | 540 |
| tgcccacttg gcagtacatc aagtgtatca tatgccaagt acgccccecta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |

```
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gatccgatat cgccgccacc atgaatccta   1380
ataagaagat catcacaatc ggaagcatct gcatggtgac aggaatggtg agcctgatgc   1440
tgcagatcgg aaatctgatc agcatctggg tgagccacag catccacaca ggaaatcagc   1500
acaaggccga gcctatcagc aatacaaatt ttctgacaga gaaggccgtg gccagcgtga   1560
agctggccgg aaatagcagc ctgtgcccta tcaatggatg ggccgtgtac agcaaggata   1620
atagcatcag aatcggaagc aagggagatg tgtttgtgat cagagagcct tttatcagct   1680
gcagccacct ggagtgcaga acatttttc tgacacaggg agccctgctg aatgataagc   1740
acagcaatgg aacagtgaag gatagaagcc ctcacagaac actgatgagc tgccctgtgg   1800
gagaggcccc tagcccttac aatagcagat tgagagcgt ggcctggagc ccagcgcct    1860 gccacgatgg aacaagctgg ctgacaatcg gaatcagcgg acctgataat ggagccgtgg   1920
ccgtgctgaa gtacaatgga atcatcacag atacaatcaa gagctggaga aataatatcc   1980
tgagaacaca ggagagcgag tgcgcctgcg tgaatggaag ctgctttaca gtgatgacag   2040
atggacctag caatggacag gccagccaca agatctttaa gatggagaag ggaaaggtgg   2100
tgaagagcgt ggagctggat gcccctaatt accactacga ggagtgcagc tgctaccctg   2160
atgccggaga gatcacatgc gtgtgcagag ataattggca cggaagcaat agaccttggg   2220
tgagctttaa tcagaatctg gagtaccaga tcggatacat ctgcagcgga gtgtttggag   2280
ataatcctag acctaatgat ggaacaggaa gctgcgacc tgtgagcagc aatggagcct   2340
acggagtgaa gggatttagc tttaagtacg gaaatggagt gtggatcgga agaacaaaga   2400
gcacaaatag cagaagcgga tttgagatga tctgggaccc taatgatgga acagagacag   2460
atagcagctt tagcgtgaag caggatatcg tggccatcac agattggagc ggatacagcg   2520
gaagctttgt gcagcaccct gagctgacag gactggattg catcagacct tgcttttggg   2580
tggagctgat cagaggaaga cctaaggaga gcacaatctg gacaagcgga agcagcatca   2640
gcttttgcgg agtgaatagc gatacagtgg atgagctg gcctgatgga gccgagctgc   2700
cttttacaat cgataagtga gcggccgctc tagaccaggc cctggatcca gatctgctgt   2760
gccttctagt tgccagccat ctgttgttg cccctccccc gtgccttcct tgaccctgga   2820
aggtgccact cccactgtcc tttcctaata aaatgaggaa attgcatcgc attgtctgag   2880
taggtgtcat tctattctgg ggggtgggt ggggcaggac agcaagggg aggattggga   2940 agacaatagc aggcatgctg gggatgcggt gggctctatg ggtacccagg tgctgaagaa   3000
ttgacccggt tcctcctggg ccagaaagaa gcaggcacat ccccttctct gtgacacacc   3060
```

```
ctgtccacgc ccctggttct tagttccagc cccactcata ggacactcat agctcaggag   3120
ggctccgcct tcaatcccac ccgctaaagt acttggagcg gtctctccct ccctcatcag   3180
cccaccaaac caaacctagc ctccaagagt gggaagaaat taaagcaaga taggctatta   3240
agtgcagagg gagagaaaat gcctccaaca tgtgaggaag taatgagaga aatcatagaa   3300
ttttaaggcc atgatttaag gccatcatgg ccttaatctt ccgcttcctc gctcactgac   3360
tcgctgcgct cggtcgttcg gctgcggcga gcggtatcag ctcactcaaa ggcggtaata   3420
cggttatcca cagaatcagg ggataacgca ggaaagaaca tgtgagcaaa aggccagcaa   3480
aaggccagga accgtaaaaa ggccgcgttg ctggcgtttt tccataggct ccgcccccct   3540
gacgagcatc acaaaaatcg acgctcaagt cagaggtggc gaaacccgac aggactataa   3600
agataccagg cgtttccccc tggaagctcc ctcgtgcgct ctcctgttcc gaccctgccg   3660
cttaccggat acctgtccgc ctttctccct tcgggaagcg tggcgctttc tcatagctca   3720
cgctgtaggt atctcagttc ggtgtaggtc gttcgctcca agctgggctg tgtgcacgaa   3780
ccccccgttc agcccgaccg ctgcgcctta tccggtaact atcgtcttga gtccaacccg   3840
gtaagacacg acttatcgcc actggcagca gccactggta acaggattag cagagcgagg   3900
tatgtaggcg gtgctacaga gttcttgaag tggtggccta actacggcta cactagaaga   3960
acagtatttg gtatctgcgc tctgctgaag ccagttacct tcggaaaaag agttggtagc   4020
tcttgatccg gcaaacaaac caccgctggt agcggtggtt tttttgtttg caagcagcag   4080
attacgcgca gaaaaaaagg atctcaagaa gatcctttga tcttttctac ggggtctgac   4140
gctcagtgga acgaaaactc acgttaaggg attttggtca tgagattatc aaaaaggatc   4200
ttcacctaga tccttttaaa ttaaaaatga agttttaaat caatctaaag tatatatgag   4260
taaacttggt ctgacagtta ccaatgctta atcagtgagg cacctatctc agcgatctgt   4320
ctatttcgtt catccatagt tgcctgactc ggggggggg ggcgctgagg tctgcctcgt   4380
gaagaaggtg ttgctgactc ataccaggcc tgaatcgccc catcatccag ccagaaagtg   4440
agggagccac ggttgatgag agctttgttg taggtggacc agttggtgat tttgaacttt   4500
tgctttgcca cggaacggtc tgcgttgtcg ggaagatgcg tgatctgatc cttcaactca   4560
gcaaaagttc gatttattca acaaagccgc cgtcccgtca agtcagcgta atgctctgcc   4620
agtgttacaa ccaattaacc aattctgatt agaaaaactc atcgagcatc aaatgaaact   4680
gcaatttatt catatcagga ttatcaatac catattttg aaaaagccgt ttctgtaatg   4740
aaggagaaaa ctcaccgagg cagttccata ggatggcaag atcctggtat cggtctgcga   4800
ttccgactcg tccaacatca atacaaccta ttaatttccc ctcgtcaaaa ataaggttat   4860
caagtgagaa atcaccatga gtgacgactg aatccggtga gaatggcaaa agcttatgca   4920
tttctttcca gacttgttca acaggccagc cattacgctc gtcatcaaaa tcactcgcat   4980
caaccaaacc gttattcatt cgtgattgcg cctgagcgag acgaaatacg cgatcgctgt   5040
taaaaggaca attacaaaca ggaatcgaat gcaaccggcg caggaacact gccagcgcat   5100
caacaatatt ttcacctgaa tcaggatatt cttctaatac ctggaatgct gttttcccgg   5160
ggatcgcagt ggtgagtaac catgcatcat caggagtacg gataaaatgc ttgatggtcg   5220
gaagaggcat aaattccgtc agccagttta gtctgaccat ctcatctgta acatcattgg   5280
caacgctacc tttgccatgt ttcagaaaca actctggcgc atcgggcttc ccatacaatc   5340
gatagattgt cgcacctgat tgcccgacat tatcgcgagc ccatttatac ccatataaat   5400
cagcatccat gttggaattt aatcgcggcc tcgagcaaga cgtttcccgt tgaatatggc   5460
```

-continued

```
tcataacacc ccttgtatta ctgtttatgt aagcagacag ttttattgtt catgatgata        5520
tatttttatc ttgtgcaatg taacatcaga gattttgaga cacaacgtgg ctttccccccc       5580 cccccatta ttgaagcatt tatcagggtt attgtctcat gagcggatac atatttgaat         5640
gtatttagaa aaataaacaa ataggggttc cgcgcacatt tccccgaaaa gtgccacctg        5700
acgtctaaga aaccattatt atcatgacat taacctataa aaataggcgt atcacgaggc        5760
cctttcgtc                                                                5769
```

<210> SEQ ID NO 9
<211> LENGTH: 4598
<212> TYPE: DNA
<213> ORGANISM: Artificial Sequence
<220> FEATURE:
<223> OTHER INFORMATION: Artificial construct

<400> SEQUENCE: 9

```
cgacaatatt ggctattggc cattgcatac gttgtatcta tatcataata tgtacattta          60
tattggctca tgtccaatat gaccgccatg ttgacattga ttattgacta gttattaata         120
gtaatcaatt acggggtcat tagttcatag cccatatatg gagttccgcg ttacataact         180
tacggtaaat ggcccgcctc gtgaccgccc aacgaccccc gcccattgac gtcaataatg         240
acgtatgttc ccatagtaac gccaataggg actttccatt gacgtcaatg ggtggagtat         300
ttacggtaaa ctgcccactt ggcagtacat caagtgtatc atatgccaag tccgccccta         360
ttgacgtcaa tgacggtaaa tggcccgcct ggcattatgc ccagtacatg accttacggg         420
actttcctac ttggcagtac atctacgtat tagtcatcgc tattaccatg gtgatgcggt         480
tttggcagta caccaatggg cgtggatagc ggtttgactc acggggattt ccaagtctcc         540
accccattga cgtcaatggg agtttgtttt ggcaccaaaa tcaacgggac tttccaaaat         600
gtcgtaataa ccccgccccg ttgacgcaaa tgggcggtag gcgtgtacgg tgggaggtct         660
atataagcag agctcgttta gtgaaccgtc agatcgcctg gagacgccat ccacgctgtt         720
ttgacctcca tagaagacac cgggaccgat ccagcctccg cggccgggaa cggtgcattg         780
gaacgcggat tccccgtgcc aagagtgacg taagtaccgc ctatagactc tataggcaca         840
cccctttggc tcttatgcat gctatactgt ttttggcttg gggcctatac accccgctc         900 cttatgctat aggtgatggt atagcttagc ctataggtgt gggttattga ccattattga         960
ccactcccct attggtgacg atactttcca ttactaatcc ataacatggc tctttgccac        1020
aactatctct attggctata tgccaatact ctgtccttca gagactgaca cggactctgt        1080
atttttacag gatggggtcc catttattat ttacaaattc acatatacaa caacgccgtc        1140 cccgtgccc gcagttttta ttaaacatag cgtgggatct ccacgcgaat ctcgggtacg        1200
tgttccggac atgggctctt ctccggtagc ggcggagctt ccacatccga gccctggtcc       1260
catgcctcca gcggctcatg gtcgctcggc agctccttgc tcctaacagt ggaggccaga       1320
cttaggcaca gcacaatgcc caccaccacc agtgtgccgc acaaggccgt ggcggtaggg        1380
tatgtgtctg aaaatgagct cggagattgg gctcgcaccg tgacgcagat ggaagactta       1440
aggcagcggc agaagaagat gcaggcagct gagttgttgt attctgataa gagtcagagg        1500
taactcccgt tgcggtgctg ttaacggtgg agggcagtgt agtctgagca gtactcgttg        1560
ctgccgcgcg cgccaccaga cataatagct gacagactaa cagactgttc ctttccatgg        1620
gtcttttctg cagtcaccgt ccaagcttag atctgccacc atgagcctgc tgaccgaggt        1680
```

```
ggagacatac gtgctgtcca tcatccccag cggccctctg aaggccgaga tcgcccagag    1740
actggaagat gtgttcgccg gcaagaacac cgacctggaa gtgctgatgg aatggctgaa    1800
aaccagaccc atcctgagcc ctctgaccaa gggcatcctg ggcttcgtgt tcaccctgac    1860
cgtgcccagc gagagaggcc tgcagaggcg gagattcgtg cagaacgccc tgaacggcaa    1920
cggcgacccc aacaacatgg acaaggccgt gaagctgtac agaaagctga agcgggagat    1980
caccttccac ggcgccaaag agatcagcct gagctacagc gctggcgccc tggccagctg    2040
catgggcctg atctacaaca gaatgggcgc cgtgaccacc gaggtggcct tcggcctggt    2100
ctgcgccacc tgcgagcaga tcgccgacag ccagcacaga tcccacagac agatggtcac    2160
caccaccaac cccctgatca gacacgagaa cagaatggtg ctggcctcta ccaccgccaa    2220
ggccatggaa cagatggccg gcagcagcga gcaggccgcc gaggctatgg aagtcgcctc    2280
tcaggctagg cagatggtcc aggccatgag aaccatcggc acccacccca gcagctctgc    2340
tggcctgaag aacgacctgc tggaaaacct gcaggcctac cagaaaagaa tgggcgtcca    2400
gatgcagaga ttcaagtgat gagatatccc tcagagaggg gatcctcgca atccctaggg    2460
ctgtgccttc tagttgccag ccaaactgtt gtttgcccct ccccgtgcc ttccttgacc     2520 ctggaaggtg ccactcccac tgtccttttcc taataaaatg aggaaattgc atcgcattgt    2580
ctgagtaggt gtcattctat tctgggggt ggggtgggc aggacagcaa ggggaggat       2640 tgggaagaca atagcaggca tgctggggat gcggtgggct ctatgttcag aacgctcggt    2700
tgccgccggg cgttttttat ctagagtcga caaattcaga agaactcgtc aagaaggcga    2760
tagaaggcga tgcgctgcga tcgggagcg gcgataccgt aaagcacgag gaagcggtca     2820
gcccattcgc cgccaagctc ttcagcaata tcacgggtag ccaacgctat gtcctgatag    2880
cggtccgcca cacccagccg gccacagtcg atgaatccag aaaagcggcc attttccacc    2940
atgatattcg gcaagcaggc atcgccatgg gtcacgacga gatcctcgcc gtcgggcatg    3000
ctcgccttga gcctggcgaa cagttcggct ggcgcgagcc cctgatgctc ttcgtccaga    3060
tcatcctgat cgacaagacc ggcttccatc cgagtacgtg ctcgctcgat gcgatgtttc    3120
gcttggtggt cgaatgggca ggtagccgga tcaagcgtat gcagccgccg cattgcatca    3180
gccatgatgg atactttctc ggcaggagca aggtgagatg acaggagatc ctgccccggc    3240
acttcgccca atagcagcca gtcccttccc gcttcagtga caacgtcgag cacagctgcg    3300
caaggaacgc ccgtcgtggc cagccacgat agccgcgctg cctcgtcttg cagttcattc    3360
agggcaccgg acaggtcggt cttgacaaaa agaaccgggc gcccctgcgc tgacagccgg    3420
aacacggcgg catcagagca gccgattgtc tgttgtgccc agtcatagcc gaatagcctc    3480
tccacccaag cggccggaga acctgcgtgc aatccatctt gttcaatcat gcgaaacgat    3540
cctcatcctg tctcttgatc agatcttgat cccctgcgcc atcagatcct ggcggcgag    3600 aaagccatcc agtttacttt gcagggcttc ccaaccttac cagagggcgc cccagctggc    3660
aattccggtt cgcttgctgt ccataaaacc gcccagtcta gctatcgcca tgtaagccca    3720
ctgcaagcta cctgctttct ctttgcgctt gcgttttccc ttgtccagat agcccagtag    3780
ctgacattca tccggggtca gcaccgtttc tgcggactgg cttctacgt gaaaaggatc     3840 taggtgaaga tcctttttga atctcatg accaaaatcc cttaacgtga gttttcgttc      3900
cactgagcgt cagaccccgt agaaaagatc aaaggatctt cttgagatcc ttttttttctg   3960 cgcgtaatct gctgcttgca aacaaaaaaa ccaccgctac cagcggtggt ttgtttgccg    4020
gatcaagagc taccaactct ttttccgaag gtaactggct tcagcagagc gcagatacca    4080
```

```
aatactgtcc ttctagtgta gccgtagtta ggccaccact tcaagaactc tgtagcaccg    4140
cctacatacc tcgctctgct aatcctgtta ccagtggctg ctgccagtgg cgataagtcg    4200
tgtcttaccg ggttggactc aagacgatag ttaccggata aggcgcagcg gtcgggctga    4260
acggggggtt cgtgcacaca gcccagcttg gagcgaacga cctacaccga actgagatac    4320
ctacagcgtg agctatgaga aagcgccacg cttcccgaag ggagaaaggc ggacaggtat    4380
ccggtaagcg gcagggtcgg aacaggagag cgcacgaggg agcttccagg gggaaacgcc    4440
tggtatcttt atagtcctgt cgggtttcgc cacctctgac ttgagcgtcg atttttgtga    4500
tgctcgtcag gggggcggag cctatggaaa aacgccagca acgcggcctt tttacggttc    4560
ctgggctttt gctggccttt tgctcacatg ttgtcgac                            4598

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide

<400> SEQUENCE: 10

Ile Tyr Ser Thr Val Ala Ser Ser Leu
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide

<400> SEQUENCE: 11

Ser Ile Ile Asn Phe Glu Lys Leu
1               5
```

COMPUTATIONALLY OPTIMIZED BROADLY REACTIVE ANTIGENS FOR INFLUENZA

CROSS REFERENCE TO RELATED APPLICATIONS

This is the U.S. National Stage of International Application No. PCT/US2011/051072, filed Sep. 9, 2011, published in English under PCT Article 21(2), which claims the benefit of U.S. Provisional Application No. 61/403,407, filed Sep. 14, 2010, which is herein incorporated by reference in its entirety.

FIELD

This disclosure concerns an optimized influenza hemagglutinin protein that elicits broadly reactive immune responses to H5N1 virus isolates and its use as a vaccine.

BACKGROUND

Influenza virus is a member of Orthomyxoviridae family. There are three subtypes of influenza viruses, designated influenza A, influenza B, and influenza C. The influenza virion contains a segmented negative-sense RNA genome, which encodes the following proteins: hemagglutinin (HA), neuraminidase (NA), matrix (M1), proton ion-channel protein (M2), nucleoprotein (NP), polymerase basic protein 1 (PB1), polymerase basic protein 2 (PB2), polymerase acidic protein (PA), and nonstructural protein 2 (NS2). The HA, NA, M1, and M2 are membrane associated, whereas NP, PB1, PB2, PA, and NS2 are nucleocapsid associated proteins. The M1 protein is the most abundant protein in influenza particles. The HA and NA proteins are envelope glycoproteins, responsible for virus attachment and penetration of the viral particles into the cell, and the sources of the major immunodominant epitopes for virus neutralization and protective immunity. Both HA and NA proteins are considered the most important components for prophylactic influenza vaccines.

Each year, seasonal influenza causes over 300,000 hospitalizations and 36,000 deaths in the U.S. alone (Simonsen et al., *Lancet Infect Dis* 7:658-66, 2007). The emergence of the novel H1N1 influenza virus in 2009 demonstrated how quickly a new influenza pandemic can sweep across the world. The spread of highly pathogenic H5N1 viruses in birds and coincident infections in humans have raised the concerns that H5N1 viruses may cause a new pandemic in humans. Vaccination is an effective method to prevent influenza infection. There are two influenza vaccine approaches licensed in the United States; the inactivated, split vaccine and the live-attenuated virus vaccine. Inactivated vaccines can efficiently induce humoral immune responses but generally only poor cellular immune responses. Thus, a need exists for a broadly protective influenza virus vaccine.

SUMMARY

Disclosed herein is the development of an optimized influenza HA protein that elicits broadly reactive immune response to H5N1 influenza virus isolates. The optimized HA protein was developed through a series of HA protein alignments, and subsequent generation of consensus sequences for clade 2 H5N1 influenza virus isolates (FIG. 1). The final consensus HA amino acid sequence was reverse translated and optimized for expression in mammalian cells. The optimized HA coding sequence is set forth herein as SEQ ID NO: 1, and the optimized HA protein sequence is set forth herein as SEQ ID NO: 2.

Provided herein is an isolated nucleic acid molecule comprising a nucleotide sequence encoding an optimized influenza HA polypeptide, wherein the nucleotide sequence encoding the HA polypeptide is at least 94%, at least 95%, at least 96%, at least 97%, at least 98% or at least 99% identical to SEQ ID NO: 1. Optimized influenza HA polypeptides encoded by the nucleic acid molecule, vectors comprising the nucleic acid molecule, and host cells containing the disclosed vectors are also provided herein.

Further provided is an optimized influenza HA polypeptide, wherein the amino acid sequence of the polypeptide is at least 99% identical to SEQ ID NO: 2. Also provided are fusion proteins comprising the optimized HA polypeptide, virus-like particles (VLPs) containing the optimized HA polypeptides, and compositions comprising the optimized HA polypeptide.

Collections of plasmids are also provided herein. In some embodiments, the collections of plasmids include a plasmid encoding an influenza NA, a plasmid encoding an influenza MA, and a plasmid encoding the optimized HA protein disclosed herein.

Further provided is a method of eliciting an immune response to influenza virus in a subject by administering the optimized influenza HA protein, fusion proteins containing the optimized influenza HA, or VLPs containing the optimized influenza HA, as disclosed herein. Also provided is a method of immunizing a subject against influenza virus by administering to the subject VLPs containing the optimized influenza HA protein disclosed herein.

The foregoing and other objects and features of the disclosure will become more apparent from the following detailed description, which proceeds with reference to the accompanying figures.

BRIEF DESCRIPTION OF THE FIGURES

FIGS. 3A-3F: COBRA HA Mouse Dosing Immunogenicity. BALB/c mice (n=5/group) were vaccinated at 0 and 3 weeks with blood collected at 14 to 21 days after each vaccination. Vaccines were formulated at high (1.5 μg HA), and low (0.03 μg HA) doses, with and without Imject® alum, and delivered intramuscularly. Total IgG at week 5 was determined via ELISA for each vaccine group (A and B). Values represent the geometric mean titer (±95% confidence interval) of $\log_{10}$ transformed endpoint titers. IgG isotypes were evaluated via ELISA for each vaccine group (C and D). Values represent the mean $OD_{450}$ of a 1:200 dilution of serum. Hemagglutination inhibition (HAI) serum antibody titer for each vaccine group was determined at week 5 using representative reassortant viruses (E and F). Values represent the geometric mean titer (±95% confidence interval) of $\log_2$ transformed titers. The dotted line represents the 1:40 titer. Significant differences were determined by two-way ANOVA with Bonferroni's post-test to evaluate differences between the vaccine formulations for each test antigen. A p value of less than 0.05 was considered significant.

FIGS. 6A-6B: Mouse Comparison Efficacy. BALB/c mice (n=20/group) were vaccinated with VLPs and adjuvant. Mice were infected with $5 \times 10^3$ PFU of the highly pathogenic clade 2.2 H5N1 virus A/Whooper Swan/Mongolia/244/2005. Mice were followed to monitor weight loss (A) and sickness (B). Sickness score was determined by evaluating activity (0=normal, 1=reduced, 2=severely reduced), hunched back (0=absent, 1=present) and ruffled fur (0=absent, 1=present). All mock (adjuvant-only) vaccinated mice reached the experimental endpoint and required euthanasia by 6 days post infection.

FIGS. 8A-8E: Ferret Efficacy. Ferrets (n=9/group) were vaccinated with VLPs formulated with adjuvant. Ferrets were challenged with $1 \times 10^6$ PFU of the highly pathogenic clade 2.2 H5N1 virus A/Whooper Swan/Mongolia/244/2005. Animals were monitored daily for weight loss (A), survival (B), temperature (C) and clinical symptoms (D). Relative sickness scores were determined by measuring lethargy (0-3), runny nose (0-1), sneezing (0-1), loss of appetite (0-1) and diarrhea (0-1). Animals reaching experimental endpoint were euthanized according to institutional guidelines. Nasal washes were collected serially post infection and virus titers determined via plaque assay (E). Statistical significance was determined using a two-way ANOVA with Bonferroni's post test. A p value of less than 0.05 was considered significant.

FIG. 9: Phylogenetic diversity of H5N1 influenza. The unrooted phylogenetic tree was inferred from HA amino acid sequences derived from 8 to 10 representative isolates in all clades and sub-clades and the COBRA HA using the maximum likelihood method. Clade/sub-clade clusters were identified and are indicated in the shaded ovals. The star identifies where the COBRA antigen is located relative to the various representative isolates. Sequences were aligned with MUSCLE 3.7 software and the alignment was refined by Gblocks 0.91b software. Phylogeny was determined using the maximum likelihood method with PhyML software. Trees were rendered using TreeDyn 198.3 software (Dereeper et al., *Nucleic Acids Res* 36:W465-W469, 2008). The NCBI accession numbers for the HA sequences used in phylogeny inference were obtained through the Influenza Virus Resource (Bao et al., *J. Virol* 82:596-601, 2008).

FIGS. 10A-10F: Serology. Total IgG at week 3 (A) and week 6 (B) was determined via ELISA for each vaccine group. Each collected antiserum was assayed for antibody binding to representative HA molecules from clade 2.1 (A/Indonesia/5/2005), clade 2.2 (A/Whooper Swan/Mongolia/244/2005), and clade 2.3 (A/Anhui/1/2005). Values represent the geometric mean titer (±95% confidence interval) of $\log_{in}$ transformed endpoint titers. Statistical significance of the antibody titer data was determined using a two-way analysis of variance (ANOVA) followed by Bonferroni's post-test to analyze differences between each vaccine group for each of the different antigens that were tested (multiparametric). Significance was defined as p<0.05. Statistical analyses were performed with GraphPad Prism software. HAI titer for each vaccine group was determined at week 3 (C) and week 6 (D) using representative H5N1 influenza viruses: clade 2.1 (A/Indonesia/5/2005), clade 2.2 (A/Whooper swan/Mongolia/244/2005), and clade 2.3 (A/Anhui/1/2005). Values represent the geometric mean titer (±95% confidence interval) of $\log_2$ transformed titers. The dotted line represents the 1:40 titer. Significant differences were determined by two-way ANOVA with Bonferroni's post-test to evaluate differences between the vaccine formulations for each test antigen. A p value of less than 0.05 was considered significant. The number of monkeys that responded with a titer greater than 1:40 is listed above each bar. Neutralizing antibody at week 3 (E) and week 6 (F) was determined via microneutralization assay for each vaccine group. Values represent the geometric mean titer (±95% confidence interval).

FIG. 11: HAI serum antibody titers from vaccinated monkeys against a panel of clade 0, 1, 2, 4, and 7 isolates. HAI titer for each vaccine group was determined at week 9 using H5N1 influenza viruses. Values represent the geometric mean titer (±95% confidence interval) of $\log_2$ transformed titers. Significant differences were determined by two-way ANOVA with Bonferroni's post-test to evaluate differences between the vaccine formulations for each test antigen. A p value of less than 0.05 was considered significant as described in FIG. 10.

FIGS. 12A-12D: Vaccine induced serum antibody responses. BALB/c mice (n=30/group) or Fitch ferrets (n=6/group) were vaccinated at 0 and 3 weeks with blood collected 14 to 21 days after each vaccination. Total IgG after the second vaccination was determined via ELISA for each vaccine group (A and C). Receptor blocking antibody titers after the second vaccination were determined via hemagglutination inhibition (HAI) for each vaccine group (B and D). Values represent the geometric mean of the reciprocal dilution (+/−95% confidence interval) of the last positive well. Significant differences between COBRA and polyvalent vaccines were determined by a two-tailed Student's T test and a p value of less than 0.05 was considered significant (*).

FIGS. 13A-13D: Highly pathogenic Clade 2.2 challenge. Vaccinated BALB/c mice (n=5/group) were infected with $5\times10^3$ PFU of the highly pathogenic clade 2.2 H5N1 virus A/Whooper Swan/Mongolia/244/2005 (WS/05). Mice were monitored daily for weight loss (A) and sickness (B). Vaccinated Fitch ferrets (n=6/group) were infected with $1\times10^6$ PFU of the highly pathogenic clade WS/05 virus. Ferrets were monitored daily for weight loss (C) and sickness (D). Values represent mean (+/−SEM) for each group.

FIGS. 14A-14B: Clade 2.2 viral loads. Vaccinated BALB/c mice (n=15/group) were infected with $5\times10^3$ PFU of the highly pathogenic clade 2.2 H5N1 virus A/Whooper Swan/Mongolia/244/2005 (WS/05). Cohorts of mice (n=5/group) were sacrificed at 1, 3 and 5 days post infection, lungs harvested, and viral load determined by plaque assay (A). Vaccinated Fitch ferrets (n=6/group) were infected with $1\times10^6$ PFU of the highly pathogenic WS/05 virus. Nasal washes were collected and viral load determined by plaque assay (B). Values represent mean (+/−SEM) viral titer for each group. Significant differences between COBRA and polyvalent vaccines were determined by a two-tailed Student's T test and a p value of less than 0.05 was considered significant (*).

FIGS. 15A-15B: Histopathology of infected lungs. Vaccinated BALB/c mice (n=15/group) were infected with $5\times10^3$ PFU of the highly pathogenic clade 2.2 H5N1 virus A/Whooper Swan/Mongolia/244/2005 (WS/05). Cohorts of mice (n=5/group) were sacrificed at 3 days post infection and in situ hybridization (ISH) for influenza matrix protein (MP) was performed on sections from paraffin embedded lung tissue (A). Severity of influenza ISH foci was accessed in the bronchi (B). Scoring: 0=no definitive signal; 1=occasional focus; 2=focus in most fields; 3=more than one focus per field.

FIGS. 16A-16C: Clade 1 challenge. Vaccinated BALB/c mice (n=4/group) were infected with $5\times10^3$ PFU of reassortant virus containing the HA and NA genes from the clade 1 H5N1 virus A/Vietnam/1203/2004 (VN/04). Mice were monitored daily for weight loss (A) and sickness (B). Values represent mean (+/−SD) for each group. An additional cohort of vaccinated mice (n=3/group) were infected and lungs were harvested 3 days post infection for analysis of viral burden (C). Values represent mean (+/−SEM) viral titer for each group.

FIGS. 17A-17B: Post-challenge cellular immune responses. Vaccinated BALB/c mice (n=3/group) were infected with $5\times10^3$ PFU of reassortant virus containing the HA and NA genes from the clade 1 H5N1 virus A/Vietnam/1203/2004 (VN/04). Mice were sacrificed 6 days post infection, lungs were harvested and the numbers of antibody secreting cells (A) and IFN-γ producing cells (B) were determined by ELISpot assay. Values represent the mean (+/−SEM) spots for each group.

FIGS. 18A-18B: Passive transfer clade 1 challenge. BALB/c mice (n=10/group) were vaccinated at 0 and 3 weeks with blood collected 14 to 21 days after each vaccination. Serum collected after the second vaccination was pooled for each vaccine group and administered to naïve recipient mice (n=5/group). One day after passive transfer, recipient mice were infected with $5\times10^3$ PFU of reassortant virus containing the HA and NA genes from the clade 1 H5N1 virus A/Vietnam/1203/2004 (VN/04). Mice were monitored daily for weight loss (A) and sickness (B). Values represent mean (+/−SD) for each group. Significant differences were determined by two-way ANOVA with Bonferroni's post-test to evaluate differences between vaccines at each day. A p value of less than 0.05 was considered significant (*).

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, crewed on Mar. 8, 2013, 50.9 KB, which is incorporated by reference herein. In the accompanying sequence listing:

SEQ ID NOs: 1 and 2 are the nucleotide and amino acid sequences, respectively, of a codon-optimized influenza HA (designated COBRA).

SEQ ID NOs: 3 and 4 are the nucleotide and amino acid sequences, respectively, of a codon-optimized influenza NA.

SEQ ID NOs: 5 and 6 are the nucleotide and amino acid sequences, respectively, of a codon-optimized influenza M1.

SEQ ID NO: 7 is the nucleotide sequence of a plasmid encoding a codon-optimized influenza HA.

SEQ ID NO: 8 is the nucleotide sequence of a plasmid encoding a codon-optimized influenza NA.

SEQ ID NO: 9 is the nucleotide sequence of a plasmid encoding a codon-optimized influenza M1.

SEQ ID NO: 10 is the amino acid sequence of a T cell epitope in H5 HA ($HA_{533}$).

SEQ ID NO: 11 is the amino acid sequence of an ovalbumin T cell epitope ($OVa_{257}$).

DETAILED DESCRIPTION

I. Abbreviations

ASC: antibody secreting cell
DPI: days post infection
HA: hemagglutinin or hemagglutination assay
HAI: hemagglutination inhibition
hRBC: horse red blood cell
IFU: infectious unit LD$_{50}$: lethal dose 50
M1: matrix protein 1
MN: microneutralization
MOI: multiplicity of infection
NA: neuraminidase
PFU: plaque form unit
RDE: receptor destroying enzyme
TCID: tissue culture infectious dose
tRBC: turkey red blood cell
VLP: virus-like particle

II. Terms and Methods

Figure 1A:
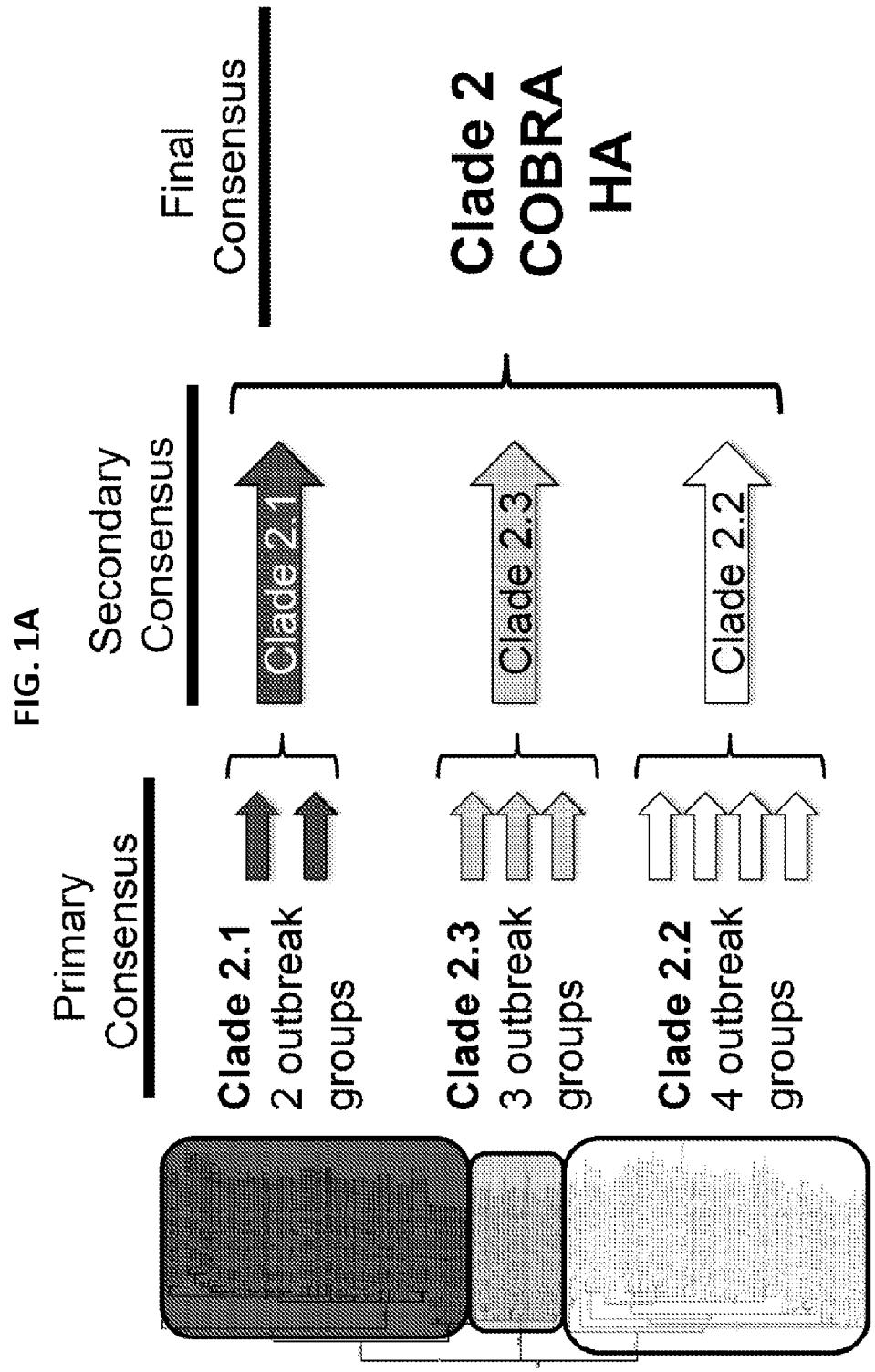
FIGS. 1A-1B: COBRA HA Design. (A) Schematic illustrating the design of the COBRA HA molecule. The phylogenetic tree was inferred from hemagglutinin amino acid sequences using the maximum likelihood method and clade/sub-clade groupings were identified. Primary consensus sequences were generated for each outbreak group. Secondary consensus sequences were then generated for each sub-clade using the primary sequences as input. The secondary consensus sequences were then aligned and the resulting consensus, designated COBRA, was generated. (B) Phylogenetic analysis of the COBRA HA. The unrooted phylogenetic tree was inferred from hemagglutinin amino acid sequences from human H5N1 infections isolated from 2004 to 2009 and the clade/sub-clade groupings are indicated. The star represents the COBRA HA sequence relative to human H5N1 infections.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL.

Administer: As used herein, administering a composition to a subject means to give, apply or bring the composition into contact with the subject. Administration can be accomplished by any of a number of routes, such as, for example, topical, oral, subcutaneous, intramuscular, intraperitoneal, intravenous, intrathecal and intramuscular.

Antibody: An immunoglobulin molecule produced by B lymphoid cells with a specific amino acid sequence. Antibodies are evoked in humans or other animals by a specific antigen (immunogen). Antibodies are characterized by reacting specifically with the antigen in some demonstrable way, antibody and antigen each being defined in terms of the other. "Eliciting an antibody response" refers to the ability of an antigen or other molecule to induce the production of antibodies.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In some embodiments of the disclosed compositions and methods, the antigen is an influenza HA protein.

Attenuated: In the context of a live virus, the virus is attenuated if its ability to infect a cell or subject and/or its ability to produce disease is reduced (for example, eliminated) compared to a wild-type virus. Typically, an attenuated virus retains at least some capacity to elicit an immune response following administration to an immunocompetent subject. In some cases, an attenuated virus is capable of eliciting a protective immune response without causing any signs or symptoms of infection. In some embodiments, the ability of an attenuated virus to cause disease in a subject is reduced at least about 10%, at least about 25%, at least about 50%, at least about 75% or at least about 90% relative to wild-type virus.

Clade: Refers to the different categorizations of the known influenza viruses, such as influenza A H5N1 viruses. Viruses in an H5N1 clade are genetically related, but do not share the exact viral genome. There are at least ten different clades of H5N1 subtypes designated in the art: clade 0 clade 1, clade 2, clade 3, clade 4, clade 5, clade 6, clade 7, clade 8 and clade 9 (Abdel-Ghafar et al., *N Engl J Med* 358:261-273, 2008). Clade 2 is further divided into sub-clades (including clade 2.1, clade 2.2, clade 2.3, clade 2.4 and clade 2.5).

Codon-optimized: A "codon-optimized" nucleic acid refers to a nucleic acid sequence that has been altered such that the codons are optimal for expression in a particular system (such as a particular species of group of species). For example, a nucleic acid sequence can be optimized for expression in mammalian cells. Codon optimization does not alter the amino acid sequence of the encoded protein.

Fusion protein: A protein generated by expression of a nucleic acid sequence engineered from nucleic acid sequences encoding at least a portion of two different (heterologous) proteins. To create a fusion protein, the nucleic acid sequences must be in the same reading frame and contain to internal stop codons. For example, a fusion protein includes an influenza HA fused to a heterologous protein.

Geographical location or geographical region: Refers to preselected divisions of geographical areas of the earth, for example, by continent or other preselected territory or subdivision (e.g., the Middle East, which spans more than one continent). Examples of different geographical regions include countries (e.g., Turkey, Egypt, Iraq, Azerbaijan, China, United States), continents (e.g., Asia, Europe, North America, South America, Oceania, Africa), and recognized geopolitical subdivisions (such as the Middle East).

Hemagglutinin (HA): An influenza virus surface glycoprotein. HA mediates binding of the virus particle to a host cells and subsequent entry of the virus into the host cell. The nucleotide and amino acid sequences of numerous influenza HA proteins are known in the art and are publically available, such as those deposited with GenBank (see Table 1 for a list of GenBank Accession Nos. of H5N1 HA sequences). HA (along with NA) is one of the two major influenza virus antigenic determinants.

Immune response: A response of a cell of the immune system, such as a B-cell, T-cell, macrophage or polymorphonucleocyte, to a stimulus such as an antigen or vaccine. An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection). Methods of measuring immune responses are well known in the art and include, for example, measuring proliferation and/or activity of lymphocytes (such as B or T cells), secretion of cytokines or chemokines, inflammation, antibody production and the like.

Immunogen: A compound, composition, or substance which is capable, under appropriate conditions, of stimulating an immune response, such as the production of antibodies or a T-cell response in an animal, including compositions that are injected or absorbed into an animal. As used herein, as "immunogenic composition" is a composition comprising an immunogen (such as an HA polypeptide).

Immunize: To render a subject protected from an infectious disease, such as by vaccination.

Influenza virus: A segmented negative-strand RNA virus that belongs to the Orthomyxoviridae family. There are three types of Influenza viruses, A, B and C. Influenza A viruses infect a wide variety of birds and mammals, including humans, horses, marine mammals, pigs, ferrets, and chickens. In animals, most influenza A viruses cause mild localized infections of the respiratory and intestinal tract. However, highly pathogenic influenza A strains, such as H5N1, cause systemic infections in poultry in which mortality may reach 100%. H5N1 is also referred to as "avian influenza."

Isolated: An "isolated" biological component (such as a nucleic acid, protein or virus) has been substantially separated or purified away from other biological components (such as cell debris, or other proteins or nucleic acids). Biological components that have been "isolated" include those components purified by standard purification methods. The term also embraces recombinant nucleic acids, proteins or viruses, as well as chemically synthesized nucleic acids or peptides.

Linker: One or more amino acids that serve as a spacer between two polypeptides of a fusion protein.

Matrix (M1) protein: An influenza virus structural protein found within the viral envelope. M1 is thought to function in assembly and budding.

Neuraminidase (NA): An influenza virus membrane glycoprotein. NA is involved in the destruction of the cellular receptor for the viral HA by cleaving terminal sialic acid residues from carbohydrate moieties on the surfaces of infected cells. NA also cleaves sialic acid residues from viral proteins, preventing aggregation of viruses. NA (along with HA) is one of the two major influenza virus antigenic determinants.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Optimized influenza HA protein: As used herein, "optimized influenza HA protein" refers to the HA protein consensus sequence generated by sequence alignments of clade 2 H5N1 influenza viruses (as described in Example 1 below). The nucleotide sequence encoding the optimized HA protein was further optimized for expression in mammalian cells via codon-optimization and RNA optimization (such as to increase RNA stability). The optimized influenza HA protein disclosed herein (and set forth herein as SEQ ID NO: 2) is also referred to as "COBRA."

ORF (open reading frame): A series of nucleotide triplets (codons) coding for amino acids without any termination codons. These sequences are usually translatable into a peptide.

Outbreak: As used herein, an influenza virus "outbreak" refers to a collection of virus isolates from within a single country in a given year.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compositions, such as one or more influenza vaccines, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Plasmid: A circular nucleic acid molecule capable of autonomous replication in a host cell.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: An array of nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor). In some embodiments herein, the promoter is a CMV promoter.

Purified: The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Recombinant: A recombinant nucleic acid, protein or virus is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a given gene or protein will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237-244, 1988; Higgins and Sharp, CABIOS 5:151-153, 1989; Corpet et al., *Nucleic Acids Research* 16:10881-10890, 1988; and Pearson and Lipman, *Proc. Natl. Acad. Sci. U.S.A.* 85:2444, 1988. Altschul et al., *Nature Genet.* 6:119-129, 1994.

The NCBI Basic Local Alignment Search Tool (BLAST™) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

Subject: Living multi-cellular vertebrate organisms, a category that includes both human and non-human mammals, such as non-human primates. In one example, a subject is one who is infected with H5N1 or is susceptible to such infection.

Therapeutically effective amount: A quantity of a specified agent sufficient to achieve a desired effect in a subject being treated with that agent. For example, this may be the amount of an influenza virus vaccine useful for eliciting an immune response in a subject and/or for preventing infection by influenza virus. Ideally, in the context of the present disclosure, a therapeutically effective amount of an influenza vaccine is an amount sufficient to increase resistance to, prevent, ameliorate, and/or treat infection caused by influenza virus in a subject without causing a substantial cytotoxic effect in the subject. The effective amount of an influenza vaccine useful for increasing resistance to, preventing, ameliorating, and/or treating infection in a subject will be dependent on, for example, the subject being treated, the manner of administration of the therapeutic composition and other factors.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vaccine: A preparation of immunogenic material capable of stimulating an immune response, administered for the prevention, amelioration, or treatment of disease, such as an infectious disease. The immunogenic material may include, for example, attenuated or killed microorganisms (such as attenuated viruses), or antigenic proteins, peptides or DNA derived from them. Vaccines may elicit both prophylactic (preventative) and therapeutic responses. Methods of administration vary according to the vaccine, but may include inoculation, ingestion, inhalation or other forms of administration. Inoculations can be delivered by any of a number of routes, including parenteral, such as intravenous, subcutaneous or intramuscular. Vaccines may be administered with an adjuvant to boost the immune response.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. An insertional vector is capable of inserting itself into a host nucleic acid. A vector can also include one or more selectable marker genes and other genetic elements. An expression vector is a vector that contains the necessary regulatory sequences to allow transcription and translation of inserted gene or genes. In some embodiments of the present disclosure, the vector encodes an influenza HA, NA or M1 protein. In some embodiments, the vector is the pTR600 expression vector (U.S. Patent Application Publication No. 2002/0106798; Ross et al., *Nat. Immunol.* 1(2):102-103, 2000; Green et al., *Vaccine* 20:242-248, 2001).

Virus-like particle (VLP): Virus particles made up of one or more viral structural proteins, but lacking the viral genome. Because VLPs lack a viral genome, they are non-infectious. In addition, VLPs can often be produced by heterologous expression and can be easily purified. Most VLPs comprise at least a viral core protein that drives budding and release of particles from a host cell. One example of such a core protein is influenza M1. In some embodiments herein, an influenza VLP comprises the HA, NA and M1 proteins. As described herein, influenza VLPs can be produced by transfection of host cells with plasmids encoding the HA, NA and M1 proteins. After incubation of the transfected cells for an appropriate time to allow for protein expression (such as for approximately 72 hours), VLPs can be isolated from cell culture supernatants. Example 1 provides an exemplary protocol for purifying influenza VLPs from cell supernatants. In this example, VLPs are isolated by low speed centrifugation (to remove cell debris), vacuum filtration and ultracentrifugation through 20% glycerol.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. All GenBank Accession numbers are incorporated by reference herein as they appeared in the database on Sep. 9, 2010. In case of conflict, the present specification, including explanations of terms, will control. In addition, the materials, methods, and examples are illustrative only and not intended to be limiting.

III. Overview of Several Embodiments

Disclosed herein is the development of a computationally optimized influenza HA protein that elicits broadly reactive immune responses to H5N1 influenza virus isolates, such as the isolates listed in Table 1. The optimized HA protein was developed through a series of HA protein alignments, and subsequent generation of consensus sequences, for clade 2 H5N1 influenza virus isolates (described in detail in Example 1 below; see also FIG. 1). The final consensus HA amino acid sequence was reverse translated and optimized for expression in mammalian cells. Optimization of the nucleic acid sequence included optimization of the codons for expression in mammalian cells and RNA optimization (such as RNA stability). The optimized HA coding sequence is set forth herein as SEQ ID NO: 1, and the optimized HA protein sequence is set forth herein as SEQ ID NO: 2.

Thus, provided herein is an isolated nucleic acid molecule comprising a nucleotide sequence encoding an influenza HA polypeptide. In some embodiments, the nucleotide sequence encoding the HA polypeptide is at least 94%, at least 95%, at least 96%, at least 97%, at least 98% or at least 99% identical to SEQ ID NO: 1.

In some examples, the nucleotide sequence encoding the influenza HA polypeptide that is at least 94%, at least 95%, at least 96%, at least 97%, at least 98%, or at least 99% identical to SEQ ID NO: 1 lacks the start codon (nucleotides 1-3 of SEQ ID NO: 1), encoding a N-terminal methionine. In particular examples, the nucleotide sequence encoding the influenza HA polypeptide is at least 94% identical to nucleotides 4-1707 of SEQ ID NO: 1. In other examples, the nucleotide sequence encoding the HA polypeptide comprises or consists of nucleotides 4-1707 of SEQ ID NO: 1.

In some examples, the nucleotide sequence encoding the HA polypeptide comprises SEQ ID NO: 1. In particular examples, the nucleotide sequence encoding the HA polypeptide consists of SEQ ID NO: 1. Also provided herein are influenza HA polypeptides encoded by the disclosed nucleic acid molecules.

Further provided are vectors containing a nucleotide sequence encoding an optimized HA polypeptide. In some embodiments of the vectors provided herein, the nucleotide sequence encoding the HA polypeptide is at least 94%, at least 95%, at least 96%, at least 97%, at least 98% or at least 99% identical to SEQ ID NO: 1. In some examples, the vector further includes a promoter operably linked to the nucleotide sequence encoding the HA polypeptide. In particular examples, the promoter is a cytomegalovirus (CMV) promoter. In some embodiments, the nucleotide sequence of the vector is at least 85%, at least 90%, at least 95%, at least 98% or at least 99% identical to the nucleotide sequence of SEQ ID NO: 7. In some examples, the nucleotide sequence of the vector comprises the nucleotide sequence of SEQ ID NO: 7. In particular examples, the nucleotide sequence of the vector consists of the nucleotide sequence of SEQ ID NO: 7.

Also provided herein are influenza HA polypeptides produced by transfecting a host cell with a vector provided herein under conditions sufficient to allow for expression of the HA polypeptide. Isolated cells containing the disclosed vectors are also provided.

Also provided herein are optimized influenza HA polypeptides. In some embodiments, the amino acid sequence of the polypeptide is at least 99% identical to SEQ ID NO: 2. In some examples, the amino acid sequence of the influenza HA polypeptide that is at least 99% identical to SEQ ID NO: 2 lacks the N-terminal methionine residue. In particular examples, the amino acid sequence of the influenza HA polypeptide is at least 99% identical to amino acids 2-568 of SEQ ID NO: 2. In other examples, the amino acid sequence of the HA polypeptides comprises or consists of amino acids 2-568 of SEQ ID NO: 2.

In some examples, the amino acid sequence of the polypeptide comprises the amino acid sequence of SEQ ID NO: 2. In particular examples, the amino acid sequence of the polypeptide consists of the amino acid sequence of SEQ ID NO: 2. Fusion proteins comprising the influenza HA polypeptides disclosed herein are also provided. The influenza HA polypeptide can be fused to any heterologous amino acid sequence to form the fusion protein.

Further provided herein are influenza virus-like particles (VLPs) containing an optimized influenza HA protein disclosed herein. In some embodiments, the HA protein of the VLP is at least 94%, at least 95%, at least 96%, at least 97%, at least 98%, at least 99% or 100% identical to SEQ ID NO: 2. The influenza VLPs can further include any additional influenza proteins necessary to form the virus particle. In some embodiments, the influenza VLPs further include influenza neuraminidase (NA) protein, influenza matrix (M1) protein, or both.

In some embodiments of the influenza VLPs, the amino acid sequence of the influenza NA protein is at least 85%, at least 90%, at least 95%, at least 98% or at least 99% identical to SEQ ID NO: 4. In some examples, the amino acid sequence of the influenza NA protein comprises SEQ ID NO: 4. In particular examples, the amino acid sequence of the influenza NA protein consists of SEQ ID NO: 4. In some embodiments, the amino acid sequence of the influenza M1 protein is at least 85%, at least 90%, at least 95%, at least 98% or at least 99% identical to SEQ ID NO: 6. In some examples, the amino acid sequence of the influenza M1 protein comprises SEQ ID NO: 6. In particular examples, the amino acid sequence of the influenza M1 protein consists of SEQ ID NO: 6.

Also provided is an influenza VLP containing an influenza HA polypeptide as described herein, produced by transfecting a host cell with a vector encoding the HA polypeptide, a vector encoding an influenza NA protein and a vector encoding an influenza M1 protein, under conditions sufficient to allow for expression of the HA, M1 and NA proteins.

The vectors used to express the HA, NA and M1 proteins can be any suitable expression vectors known in the art. The vectors can be, for example, mammalian expression vectors, or viral vectors. In some embodiments, the vector is the pTR600 expression vector (U.S. Patent Application Publication No. 2002/0106798, herein incorporated by reference; Ross et al., *Nat. Immunol.* 1(2):102-103, 2000; Green et al., *Vaccine* 20:242-248, 2001).

In some embodiments, the nucleotide sequence of the vector encoding the HA polypeptide is at least 85%, at least 90%, at least 95%, at least 96%, at least 97%, at least 98% or at least 99% identical to SEQ ID NO: 7. In some examples, the nucleotide sequence of the vector encoding the HA polypeptide comprises SEQ ID NO: 7. In particular examples, the nucleotide sequence of the vector encoding the HA polypeptide consists of SEQ ID NO: 7.

In some embodiments, the nucleotide sequence of the vector encoding the NA protein is at least 85%, at least 90%, at least 95%, at least 96%, at least 97%, at least 98% or at least 99% identical to SEQ ID NO: 8. In some examples, the nucleotide sequence of the vector encoding the NA protein comprises SEQ ID NO: 8. In particular examples, the nucleotide sequence of the vector encoding the NA protein consists of SEQ ID NO: 8.

In some embodiments, the nucleotide sequence of the vector encoding the M1 protein is at least 85%, at least 90%, at least 95%, at least 96%, at least 97%, at least 98% or at least 99% identical to SEQ ID NO: 9. In some examples, the nucleotide sequence of the vector encoding the M1 protein comprises SEQ ID NO: 9. In particular examples, the nucleotide sequence of the vector encoding the M1 protein consists of SEQ ID NO: 9.

Collections of plasmids are also provided herein. In some embodiments, the collection of plasmids includes a plasmid encoding an influenza NA, a plasmid encoding an influenza MA, and a plasmid encoding the optimized HA protein disclosed herein. In some embodiments, the nucleotide sequence encoding the codon-optimized influenza HA of the HA-encoding plasmid is at least 94%, at least 95%, at least 96%, at least 97%, at least 98% or at least 99% identical to SEQ ID NO: 1. Also provided are kits comprising the collection of plasmids.

In some embodiments of the collections of plasmids, the influenza NA is codon-optimized and/or the influenza M1 is codon-optimized. In some examples, the nucleotide sequence encoding the codon-optimized influenza NA is at least 85%, at least 90%, at least 95%, at least 96%, at least 97%, at least 98% or at least 99% identical to SEQ ID NO: 3. In particular examples, the nucleotide sequence encoding the codon-optimized influenza NA comprises, or consists of, SEQ ID NO: 3. In some examples, the nucleotide sequence encoding the codon-optimized influenza M1 is at least 85%, at least 90%, at least 95%, at least 96%, at least 97%, at least 98% or at least 99% identical to SEQ ID NO: 5. In particular examples, the nucleotide sequence encoding the codon-optimized influenza M1 comprises, or consists of, SEQ ID NO: 5.

In one non-limiting example, the plasmid encoding influenza NA comprises SEQ ID NO: 8; the plasmid encoding influenza M1 comprises SEQ ID NO: 9; and the plasmid encoding influenza HA comprises SEQ ID NO: 10.

In some embodiments, transfection of the collection of plasmids into host cells under conditions sufficient to allow for expression of the HA, NA and M1 proteins produces influenza VLPs comprising the HA, NA and M1 proteins.

Also provided herein are compositions comprising an optimized influenza HA protein as disclosed herein, or a fusion protein or VLP comprising the optimized influenza HA protein. In some embodiments, the compositions further comprise a pharmaceutically acceptable carrier and/or an adjuvant. For example, the adjuvant can be alum, Freund's complete adjuvant, a biological adjuvant or immunostimulatory oligonucleotides (such as CpG oligonucleotides).

Further provided is a method of eliciting an immune response to influenza virus in a subject by administering an influenza HA protein disclosed herein, fusion proteins containing the influenza HA, or VLPs containing the influenza HA, as disclosed herein. In some embodiments, the influenza virus is an H5N1 influenza virus. In some embodiments, the HA protein, HA fusion protein or VLP can be administered using any suitable route of administration, such as, for example, intramuscular. In some embodiments, the HA protein, fusion protein or VLP is administered as a composition further comprising a pharmaceutically acceptable carrier and/or an adjuvant. For example, the adjuvant can be alum, Freund's complete adjuvant, a biological adjuvant or immunostimulatory oligonucleotides (such as CpG oligonucleotides).

Also provided is a method of immunizing a subject against influenza virus by administering to the subject VLPs containing the optimized influenza HA protein disclosed herein, or administering a composition thereof. In some embodiments of the method, the composition further comprises a pharmaceutically acceptable carrier and/or an adjuvant. For example, the adjuvant can be alum, Freund's complete adjuvant, a biological adjuvant or immunostimulatory oligonucleotides (such as CpG oligonucleotides). In some embodiments, the VLPs (or compositions thereof) are administered intramuscularly.

In some embodiments of the methods of eliciting an immune response or immunizing a subject, the subject is administered at least 1 μg of the VLPs containing the optimized HA protein, such as at least 5 μg, at least 10 μg, at least 15 μg, at least 20 μg, at least 25 μg, at least 30 μg, at least 40 μg or at least 50 μg of the VLPs containing the optimized HA protein, for example about 1 to about 50 μg or about 1 to about 25 μg of the VLPs containing the optimized HA protein. In particular examples, the subject is administered about 5 to about 20 μg of the VLPs, or about 10 to about 15 μg of the VLPs. In one specific non-limiting example, the subject is administered about 15 μg of the VLPs. However, one of skill in the art is capable of determining a therapeutically effective amount (for example an amount that provides protection against H5N1 influenza virus infection) of VLPs to administer to a subject.

It is disclosed herein that administration of VLPs comprising the COBRA HA disclosed herein (SEQ ID NO: 2) elicits protective levels of HAI antibodies to a number of representative clade 2 isolates and provides complete protection against lethal challenge with a clade 2.2 H5N1 virus. In some embodiments, administration of VLPs containing an optimized influenza HA results in production of high HAI titers (≥1:40) to H5N1 clade 1, clade 2.1, clade 2.2 and clade 2.3 isolates. In some examples, the VLPs containing an optimized influenza HA elicit high HAI titers against clade 1 and/or clade 7 viruses. The VLPs containing an optimized influenza HA disclosed herein elicit a broader immune response (e.g., elicit neutralizing antibodies to a broader range is H5N1 virus isolates, such as those from clade 1, sub-clades of clade 2, and clade 7) than a polyvalent influenza virus vaccine.

Also provided herein is a method of optimizing an influenza protein sequence to elicit broadly reactive immune responses in a subject. In the context of the present disclosure, "broadly reactive" means the protein sequence elicits an immune response in a subject that is sufficient to inhibit, neutralize or prevent infection of a broad range of influenza viruses (such as most or all influenza viruses within a specific subtype). In some embodiments, the influenza protein is influenza HA or influenza NA. In one example, the optimized influenza protein is capable of eliciting a protective immune response against most or all known H5N1 influenza virus isolates (such as those listed in Table 1), such as about 80%, about 85%, about 90% or about 95% of known H5N1 influenza virus isolates.

In some embodiments, the method of optimizing an influenza protein sequence includes obtaining the amino acid sequences of a group of influenza virus isolates. For example, the group can consist of influenza virus isolates from a specific subtype (such as, for example, H5N1 or H1N1), and/or from one or more clades/sub-clades of a specific influenza subtype (for example, one or more of clades/sub-clades 0, 1, 2.1, 2.2, 2.3, 2.4, 3, 4, 5, 6, 7, 8 and 9 of H5N1). Amino acid sequences of the group of influenza viruses are first organized by clade or sub-clade and then by geographic location within each clade or sub-clade. The amino acid sequences for each geographic location are aligned to generate a primary consensus sequence for each geographical region. Grouping virus isolates by geographical region controls for single outbreak dominance and incomplete reporting and sequencing. The primary consensus sequence can be generated, for example, by multiple alignment analysis using AlignX (Vector NTI), or by any other method known in the art. The primary geographically-based consensus sequences for each clade or sub-clade are then aligned, and a secondary consensus sequence is generated for each clade or sub-clade. The secondary consensus sequences for each clade or sub-clade are then aligned to generate the optimized, broadly reactive, consensus sequence (see FIG. 1). In some embodiments, the optimized influenza virus polypeptide sequence is further optimized for expression in mammalian cells. In some examples, optimization includes reverse translation of the optimized influenza virus polypeptide sequence to generate a coding sequence, followed by codon-optimization and/or optimization of the RNA (such as for stability).

In one non-limiting example, the method of optimization includes: (i) obtaining the amino acid sequences of the polypeptide from a group of influenza virus isolates, wherein the influenza virus isolates are from the same subtype; (ii) organizing the amino acid sequences of the polypeptide from the group of influenza virus isolates by clade or sub-clade and then by geographical region within each clade or sub-clade; (iii) aligning the amino acid sequences within each geographical region to generate primary consensus sequences, wherein each geographic region is represented by a primary consensus sequence; (iv) aligning the primary consensus sequences to generate secondary consensus sequences, wherein each clade or sub-clade is represented by a secondary consensus sequence; and (v) aligning the secondary consensus sequences to generate the optimized influenza virus polypeptide sequence. In some cases, the method further includes (i) reverse translating the optimized influenza virus polypeptide sequence to generate a coding sequence; and (ii) optimizing the coding sequence for expression in mammalian cells.

In an alternative embodiment, the primary consensus sequence is obtained by aligning influenza protein sequences (such as HA or NA sequences) from viral isolates from a single outbreak (a collection of influenza virus isolates within a single country within a given year). Thus, in one non-limiting example, the method of optimization includes: (i) obtaining the amino acid sequences of the polypeptide from a group of influenza virus isolates, wherein the influenza virus isolates are from the same subtype; (ii) organizing the amino acid sequences of the polypeptide from the group of influenza virus isolates by clade or sub-clade and then by outbreak; (iii) aligning the amino acid sequences within each outbreak to generate primary consensus sequences, wherein each outbreak is represented by a primary consensus sequence; (iv) aligning the primary consensus sequences to generate secondary consensus sequences, wherein each clade or sub-clade is represented by a secondary consensus sequence; and (v) aligning the secondary consensus sequences to generate the optimized influenza virus polypeptide sequence. In some cases, the method further includes (i) reverse translating the optimized influenza virus polypeptide sequence to generate a coding sequence; and (ii) optimizing the coding sequence for expression in mammalian cells.

VI. Influenza

Influenza viruses are segmented negative-strand RNA viruses that belong to the Orthomyxoviridae family. There are three types of Influenza viruses, A, B and C. Influenza A viruses infect a wide variety of birds and mammals, including humans, horses, marine mammals, pigs, ferrets, and chickens. In animals, most influenza A viruses cause mild localized infections of the respiratory and intestinal tract. However, highly pathogenic influenza A strains, such as H5N1, cause systemic infections in poultry in which mortality may reach 100%. Animals infected with influenza A often act as a reservoir for the influenza viruses and certain subtypes have been shown to cross the species barrier to humans.

Influenza A viruses can be classified into subtypes based on allelic variations in antigenic regions of two genes that encode surface glycoproteins, namely, hemagglutinin (HA) and neuraminidase (NA) which are required for viral attachment and cellular release. Currently, sixteen subtypes of HA (H1-H16) and nine NA (N-1-N9) antigenic variants are known for influenza A virus. Previously, only three subtypes were known to circulate in humans (H1N1, H1N2, and H3N2). However, in recent years, the pathogenic H5N1 subtype of avian influenza A has been reported to cross the species barrier and infect humans as documented in Hong Kong in 1997 and 2003, leading to the death of several patients.

In humans, the avian influenza virus infects cells of the respiratory tract as well as the intestinal tract, liver, spleen, kidneys and other organs. Symptoms of avian influenza infection include fever, respiratory difficulties including shortness of breath and cough, lymphopenia, diarrhea and difficulties regulating blood sugar levels. In contrast to seasonal influenza, the group most at risk is healthy adults which make up the bulk of the population. Due to the high pathogenicity of certain avian influenza A subtypes, particularly H5N1, and their demonstrated ability to cross over to infect humans, there is a significant economic and public health risk associated with these viral strains, including a real epidemic and pandemic threat. Currently, no effective vaccines for H5N1 infection are available.

The influenza A virus genome encodes nine structural proteins and one nonstructural (NS1) protein with regulatory functions. The influenza virus segmented genome contains eight negative-sense RNA (nsRNA) gene segments (PB2, PB1, PA, NP, M, NS, HA and NA) that encode at least ten polypeptides, including RNA-directed RNA polymerase proteins (PB2, PB 1 and PA), nucleoprotein (NP), neuraminidase (NA), hemagglutinin (subunits HA1 and HA2), the matrix proteins (M1 and M2) and the non-structural proteins (NS1 and NS2) (Krug et al., In "The Influenza Viruses," R. M. Krug, ed., Plenum Press, N.Y., 1989, pp. 89 152).

Influenza virus' ability to cause widespread disease is due to its ability to evade the immune system by undergoing antigenic change, which is believed to occur when a host is infected simultaneously with both an animal influenza virus and a human influenza virus. During mutation and reassortment in the host, the virus may incorporate an HA and/or NA surface protein gene from another virus into its genome, thereby producing a new influenza subtype and evading the immune system.

HA is a viral surface glycoprotein generally comprising approximately 560 amino acids and representing 25% of the total virus protein. It is responsible for adhesion of the viral particle to, and its penetration into, a host cell in the early stages of infection. Cleavage of the virus HA0 precursor into the HA1 and HA2 sub-fragments is a necessary step in order for the virus to infect a cell. Thus, cleavage is required in order to convert new virus particles in a host cell into virions capable of infecting new cells. Cleavage is known to occur during transport of the integral HA0 membrane protein from the endoplasmic reticulum of the infected cell to the plasma membrane. In the course of transport, hemagglutinin undergoes a series of co- and post-translational modifications including proteolytic cleavage of the precursor HA into the amino-terminal fragment HAI and the carboxy terminal HA2. One of the primary difficulties in growing influenza strains in primary tissue culture or established cell lines arises from the requirement for proteolytic cleavage activation of the influenza hemagglutinin in the host cell.

Although it is known that an uncleaved HA can mediate attachment of the virus to its neuraminic acid-containing receptors on a cell surface, it is not capable of the next step in the infectious cycle, which is fusion. It has been reported that exposure of the hydrophobic amino terminus of HA2 by cleavage is required so that it can be inserted into the target cell, thereby forming a bridge between virus and target cell membrane. This process is followed by fusion of the two membranes and entry of the virus into the target cell.

Proteolytic activation of HA involves cleavage at an arginine residue by a trypsin-like endoprotease, which is often an intracellular enzyme that is calcium dependent and has a neutral pH optimum. Since the activating proteases are cellular enzymes, the infected cell type determines whether the HA is cleaved. The HA of the mammalian influenza viruses and the nonpathogenic avian influenza viruses are susceptible to proteolytic cleavage only in a restricted number of cell types. On the other hand, HA of pathogenic avian viruses among the H5 and H7 subtypes are cleaved by proteases present in a broad range of different host cells. Thus, there are differences in host range resulting from differences in hemagglutinin cleavability which are correlated with the pathogenic properties of the virus.

Neuraminidase (NA) is a second membrane glycoprotein of the influenza viruses. The presence of viral NA has been shown to be important for generating a multi-faceted protective immune response against an infecting virus. For most influenza A viruses, NA is 413 amino acid in length, and is encoded by a gene of 1413 nucleotides. Nine different NA subtypes have been identified in influenza viruses (N1, N2, N3, N4, N5, N6, N7, N8 and N9), all of which have been found among wild birds. NA is involved in the destruction of the cellular receptor for the viral HA by cleaving terminal neuraminic acid (also called sialic acid) residues from carbohydrate moieties on the surfaces of infected cells. NA also cleaves sialic acid residues from viral proteins, preventing aggregation of viruses. Using this mechanism, it is hypothesized that NA facilitates release of viral progeny by preventing newly formed viral particles from accumulating along the cell membrane, as well as by promoting transportation of the virus through the mucus present on the mucosal surface. NA is an important antigenic determinant that is subject to antigenic variation.

In addition to the surface proteins HA and NA, influenza virus comprises six additional internal genes, which give rise to eight different proteins, including polymerase genes PB1, PB2 and PA, matrix proteins M1 and M2, nucleoprotein (NP), and non-structural proteins NS1 and NS2 (Horimoto et al., *Clin Microbiol Rev.* 14(1):129-149, 2001).

In order to be packaged into progeny virions, viral RNA is transported from the nucleus as a ribonucleoprotein (RNP) complex composed of the three influenza virus polymerase proteins, the nucleoprotein (NP), and the viral RNA, in association with the influenza virus matrix 1 (M1) protein and nuclear export protein (Marsh et al., *J. Virol,* 82:2295-2304, 2008). The M1 protein that lies within the envelope is thought to function in assembly and budding. A limited number of M2 proteins are integrated into the virions (Zebedee, *J. Virol.* 62:2762-2772, 1988). They form tetramers having H+ ion channel activity, and when activated by the low pH in endosomes, acidify the inside of the virion, facilitating its uncoating (Pinto et al., *Cell* 69:517-528, 1992). Amantadine is an anti-influenza drug that prevents viral infection by interfering with M2 ion channel activity, thus inhibiting virus uncoating.

NS1, a nonstructural protein, has multiple functions, including regulation of splicing and nuclear export of cellular mRNAs as well as stimulation of translation. The major function of NS1 seems to be to counteract the interferon activity of the host, since an NS1 knockout virus was viable although it grew less efficiently than the parent virus in interferon-nondefective cells (Garcia-Sastre, *Virology* 252:324-330, 1998).

NS2 has been detected in virus particles (Richardson et al., *Arch. Virol.* 116:69-80, 1991; Yasuda et al., *Virology* 196:249-255, 1993). The average number of NS2 proteins in a virus particle was estimated to be 130-200 molecules. An in vitro binding assay shows direct protein-protein contact between M1 and NS2. NS2-M1 complexes have also been detected by immunoprecipitation in virus-infected cell lysates. The NS2 protein is thought to play a role in the export of RNP from the nucleus through interaction with M1 protein (Ward et al., *Arch. Virol.* 140:2067-2073, 1995).

V. Influenza Proteins, VLPs and Administration Thereof

Optimized influenza HA polypeptides and influenza VLPs comprising an optimized HA (such as the HA having the sequence set forth as SEQ ID NO: 2) are provided herein. The optimized HA polypeptides can be administered to elicit an immune response against influenza. In particular examples, the optimized HA polypeptides are administered as part of a VLP.

The influenza VLPs are made up of the HA, NA and M1 proteins. The production of influenza VLPs has been described in the art and is within the abilities of one of ordinary skill in the art. As described herein, influenza VLPs can be produced by transfection of host cells with plasmids encoding the HA, NA and M1 proteins. After incubation of the transfected cells for an appropriate time to allow for protein expression (such as for approximately 72 hours), VLPs can be isolated from cell culture supernatants. Example 1 below provides an exemplary protocol for purifying influenza VLPs from cell supernatants. In this example, VLPs are isolated by low speed centrifugation (to remove cell debris), vacuum filtration and ultracentrifugation through 20% glycerol.

The influenza VLPs disclosed herein can be used as influenza vaccines to elicit a protective immune response against H5N1 influenza viruses.

Influenza HA polypeptides and VLPs comprising HA polypeptides, or compositions thereof, can be administered to a subject by any of the routes normally used for introducing recombinant virus into a subject. Methods of administration include, but are not limited to, intradermal, intramuscular, intraperitoneal, parenteral, intravenous, subcutaneous, vaginal, rectal, intranasal, inhalation or oral. Parenteral administration, such as subcutaneous, intravenous or intramuscular administration, is generally achieved by injection. Injectables can be prepared in conventional forms, either as liquid solutions or suspensions, solid forms suitable for solution or suspension in liquid prior to injection, or as emulsions. Injection solutions and suspensions can be prepared from sterile powders, granules, and tablets of the kind previously described. Administration can be systemic or local.

Influenza VLPs, or compositions thereof, are administered in any suitable manner, such as with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Administration can be accomplished by single or multiple doses. The dose administered to a subject in the context of the present disclosure should be sufficient to induce a beneficial therapeutic response in a subject over time, or to inhibit or prevent H5N1 influenza virus infection. The dose required will vary from subject to subject depending on the species, age, weight and general condition of the subject, the severity of the infection being treated, the particular composition being used and its mode of administration. An appropriate dose can be determined by one of ordinary skill in the art using only routine experimentation.

Provided herein are pharmaceutical compositions which include a therapeutically effective amount of the influenza VLPs alone or in combination with a pharmaceutically acceptable carrier. Pharmaceutically acceptable carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate. Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used with the compositions and methods provided herein are normal saline and sesame oil.

The influenza VLPs described herein can be administered alone or in combination with other therapeutic agents to enhance antigenicity. For example, the influenza VLPs can be administered with an adjuvant, such as Freund incomplete adjuvant or Freund's complete adjuvant.

Optionally, one or more cytokines, such as IL-2, IL-6, IL-12, RANTES, GM-CSF, TNF-α, or IFN-γ, one or more growth factors, such as GM-CSF or G-CSF; one or more molecules such as OX-40L or 41 BBL, or combinations of these molecules, can be used as biological adjuvants (see, for example, Salgaller et al., 1998, *J. Surg. Oncol.* 68(2):122-38; Lotze et al., 2000, *Cancer J. Sci. Am.* 6(Suppl 1):S61-6; Cao et al., 1998, *Stem Cells* 16(Suppl 1):251-60; Kuiper et al., 2000, *Adv. Exp. Med. Biol.* 465:381-90). These molecules can be administered systemically (or locally) to the host.

A number of means for inducing cellular responses, both in vitro and in vivo, are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (for example, via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcysteinly-seryl-serine can be used to prime tumor specific CTL when covalently attached to an appropriate peptide (see, Deres et al., *Nature* 342:561, 1989). Further, as the induction of neutralizing antibodies can also be primed with the same molecule conjugated to a peptide which displays an appropriate epitope, two compositions can be combined to elicit both humoral and cell-mediated responses where that is deemed desirable.

Although administration of VLPs containing the optimized HA protein, one of skill in the art would understand that it is also possible to administer the optimized influenza HA protein itself (in the absence of a viral particle) or as a fusion protein to elicit an immune response in a subject.

The following examples are provided to illustrate certain particular features and/or embodiments. These examples should not be construed to limit the disclosure to the particular features or embodiments described.

EXAMPLES

Example 1

A Computationally Optimized Broadly Reactive Antigen (COBRA) Based H5N1 VLP Vaccine Elicits Broadly Reactive Antibodies in Mice and Ferrets This example describes the finding that mice and ferrets vaccinated with COBRA hemagglutinin (HA) H5N1 VLPs exhibited protective levels of HAI antibodies to representative isolates from each sub-clade of clade 2 and were completely protected from lethal challenge with a clade 2.2 H5N1 virus.

Materials and Methods

COBRA Hemagglutinin (HA) Construction and Synthesis

Influenza A HA amino acid sequences isolated from human H5N1 infections were downloaded from the NCBI Influenza Virus Resource database (Bao et al., *J Virol* 82:596-601, 2008; see Table 1 for a complete list of accession numbers and isolate descriptions). Nucleotide sequences were translated into protein sequences using the standard genetic code. All available full length sequences from H5N1 clade 2 human infections from 2004 to 2006 were acquired and used for subsequent consensus generations. For each round of consensus generation, multiple alignment analysis was applied and the consensus sequence was generated using AlignX (Vector NTI). The final amino acid sequence, termed computationally optimized broadly reactive antigen (COBRA), was reverse translated and optimized for expression in mammalian cells, including codon usage and RNA optimization (GeneArt; Regensburg, Germany). This construct was then synthesized and inserted into the pTR600 expression vector (U.S. Patent Application Publication No. 2002/0106798; Ross et al., *Nat. Immunol.* 1(2):102-103, 2000; Green et al., *Vaccine* 20:242-248, 2001).

TABLE 1

| COBRA input sequences | | | | | |
|---|---|---|---|---|---|
| Strain | Clade | Accession | Host | Country | Year |
| A/Indonesia/534H/2006 | 2.1.2 | EU146737 | Human | Indonesia | 2006 |
| A/Indonesia/535H/2006 | 2.1.2 | EU146753 | Human | Indonesia | 2006 |
| A/Indonesia/536H/2006 | 2.1.2 | EU146754 | Human | Indonesia | 2006 |
| A/Indonesia/538H/2006 | 2.1.2 | EU146745 | Human | Indonesia | 2006 |
| A/Indonesia/546bH/2006 | 2.1.2 | EU146793 | Human | Indonesia | 2006 |
| A/Indonesia/546H/2006 | 2.1.2 | EU146755 | Human | Indonesia | 2006 |
| A/Indonesia/560H/2006 | 2.1.2 | EU146785 | Human | Indonesia | 2006 |
| A/Indonesia/CDC594/2006 | 2.1.2 | CY014272 | Human | Indonesia | 2006 |
| A/Indonesia/CDC595/2006 | 2.1.2 | CY014280 | Human | Indonesia | 2006 |
| A/Indonesia/CDC596/2006 | 2.1.2 | CY014288 | Human | Indonesia | 2006 |
| A/Indonesia/CDC597/2006 | 2.1.2 | CY014296 | Human | Indonesia | 2006 |
| A/Indonesia/CDC599/2006 | 2.1.2 | CY014303 | Human | Indonesia | 2006 |
| A/Indonesia/CDC599N/2006 | 2.1.2 | CY014477 | Human | Indonesia | 2006 |
| A/Indonesia/CDC625/2006 | 2.1.2 | CY014433 | Human | Indonesia | 2006 |
| A/Indonesia/CDC625L/2006 | 2.1.2 | CY014465 | Human | Indonesia | 2006 |
| A/Indonesia/160H/2005 | 2.1.3 | EU146648 | Human | Indonesia | 2005 |
| A/Indonesia/175H/2005 | 2.1.3 | EU146640 | Human | Indonesia | 2005 |
| A/Indonesia/177H/2005 | 2.1.3 | EU146680 | Human | Indonesia | 2005 |
| A/Indonesia/195H/2005 | 2.1.3 | EU146656 | Human | Indonesia | 2005 |
| A/Indonesia/239H/2005 | 2.1.3 | EU146664 | Human | Indonesia | 2005 |
| A/Indonesia/245H/2005 | 2.1.3 | EU146672 | Human | Indonesia | 2005 |
| A/Indonesia/283H/2006 | 2.1.3 | EU146681 | Human | Indonesia | 2006 |
| A/Indonesia/286H/2006 | 2.1.3 | EU146688 | Human | Indonesia | 2006 |
| A/Indonesia/292H/2006 | 2.1.3 | EU146713 | Human | Indonesia | 2006 |
| A/Indonesia/298H/2006 | 2.1.3 | EU146697 | Human | Indonesia | 2006 |
| A/Indonesia/304H/2006 | 2.1.3 | EU146705 | Human | Indonesia | 2006 |
| A/Indonesia/321H/2006 | 2.1.3 | EU146721 | Human | Indonesia | 2006 |
| A/Indonesia/341H/2006 | 2.1.3 | EU146729 | Human | Indonesia | 2006 |
| A/Indonesia/5/2005 | 2.1.3 | EF541394 | Human | Indonesia | 2005 |
| A/Indonesia/542H/2006 | 2.1.3 | EU146777 | Human | Indonesia | 2006 |
| A/Indonesia/567H/2006 | 2.1.3 | EU146801 | Human | Indonesia | 2006 |
| A/Indonesia/569H/2006 | 2.1.3 | EU146809 | Human | Indonesia | 2006 |
| A/Indonesia/583H/2006 | 2.1.3 | EU146817 | Human | Indonesia | 2006 |
| A/Indonesia/604H/2006 | 2.1.3 | EU146825 | Human | Indonesia | 2006 |
| A/Indonesia/7/2005 | 2.1.3 | EU146632 | Human | Indonesia | 2005 |
| A/Indonesia/CDC184/2005 | 2.1.3 | CY014197 | Human | Indonesia | 2005 |
| A/Indonesia/CDC194P/2005 | 2.1.3 | CY014168 | Human | Indonesia | 2005 |
| A/Indonesia/CDC287E/2005 | 2.1.3 | CY014198 | Human | Indonesia | 2005 |
| A/Indonesia/CDC287T/2005 | 2.1.3 | CY014199 | Human | Indonesia | 2005 |
| A/Indonesia/CDC292N/2005 | 2.1.3 | CY014200 | Human | Indonesia | 2005 |
| A/Indonesia/CDC292T/2005 | 2.1.3 | CY014201 | Human | Indonesia | 2005 |
| A/Indonesia/CDC326/2006 | 2.1.3 | CY014204 | Human | Indonesia | 2006 |

TABLE 1-continued

COBRA input sequences

| Strain | Clade | Accession | Host | Country | Year |
|---|---|---|---|---|---|
| A/Indonesia/CDC326N/2006 | 2.1.3 | CY014202 | Human | Indonesia | 2006 |
| A/Indonesia/CDC326N2/2006 | 2.1.3 | CY014203 | Human | Indonesia | 2006 |
| A/Indonesia/CDC326T/2006 | 2.1.3 | CY014205 | Human | Indonesia | 2006 |
| A/Indonesia/CDC329/2006 | 2.1.3 | CY014206 | Human | Indonesia | 2006 |
| A/Indonesia/CDC357/2006 | 2.1.3 | CY014207 | Human | Indonesia | 2006 |
| A/Indonesia/CDC370/2006 | 2.1.3 | CY014209 | Human | Indonesia | 2006 |
| A/Indonesia/CDC370E/2006 | 2.1.3 | CY014210 | Human | Indonesia | 2006 |
| A/Indonesia/CDC370P/2006 | 2.1.3 | CY014211 | Human | Indonesia | 2006 |
| A/Indonesia/CDC370T/2006 | 2.1.3 | CY014212 | Human | Indonesia | 2006 |
| A/Indonesia/CDC390/2006 | 2.1.3 | CY014213 | Human | Indonesia | 2006 |
| A/Indonesia/CDC523/2006 | 2.1.3 | CY014311 | Human | Indonesia | 2006 |
| A/Indonesia/CDC523E/2006 | 2.1.3 | CY014368 | Human | Indonesia | 2006 |
| A/Indonesia/CDC523T/2006 | 2.1.3 | CY014376 | Human | Indonesia | 2006 |
| A/Indonesia/CDC582/2006 | 2.1.3 | CY014384 | Human | Indonesia | 2006 |
| A/Indonesia/CDC610/2006 | 2.1.3 | CY014393 | Human | Indonesia | 2006 |
| A/Indonesia/CDC623/2006 | 2.1.3 | CY014401 | Human | Indonesia | 2006 |
| A/Indonesia/CDC623E/2006 | 2.1.3 | CY014409 | Human | Indonesia | 2006 |
| A/Indonesia/CDC624/2006 | 2.1.3 | CY014417 | Human | Indonesia | 2006 |
| A/Indonesia/CDC624E/2006 | 2.1.3 | CY014425 | Human | Indonesia | 2006 |
| A/Indonesia/CDC634/2006 | 2.1.3 | CY014441 | Human | Indonesia | 2006 |
| A/Indonesia/CDC634P/2006 | 2.1.3 | CY014449 | Human | Indonesia | 2006 |
| A/Indonesia/CDC634T/2006 | 2.1.3 | CY014457 | Human | Indonesia | 2006 |
| A/Indonesia/CDC644/2006 | 2.1.3 | CY014518 | Human | Indonesia | 2006 |
| A/Indonesia/CDC644T/2006 | 2.1.3 | CY014510 | Human | Indonesia | 2006 |
| A/Indonesia/CDC669/2006 | 2.1.3 | CY014481 | Human | Indonesia | 2006 |
| A/Indonesia/CDC669P/2006 | 2.1.3 | CY014489 | Human | Indonesia | 2006 |
| A/Indonesia/CDC699/2006 | 2.1.3 | CY014497 | Human | Indonesia | 2006 |
| A/Indonesia/CDC7/2005 | 2.1.3 | CY014177 | Human | Indonesia | 2005 |
| A/Indonesia/CDC739/2006 | 2.1.3 | CY014529 | Human | Indonesia | 2006 |
| A/Indonesia/CDC759/2006 | 2.1.3 | CY014543 | Human | Indonesia | 2006 |
| A/Indonesia/CDC835/2006 | 2.1.3 | CY017662 | Human | Indonesia | 2006 |
| A/Indonesia/CDC836/2006 | 2.1.3 | CY017670 | Human | Indonesia | 2006 |
| A/Indonesia/CDC836T/2006 | 2.1.3 | CY017678 | Human | Indonesia | 2006 |
| A/Indonesia/CDC887/2006 | 2.1.3 | CY017688 | Human | Indonesia | 2006 |
| A/Indonesia/CDC938/2006 | 2.1.3 | CY017638 | Human | Indonesia | 2006 |
| A/Indonesia/CDC938E/2006 | 2.1.3 | CY017646 | Human | Indonesia | 2006 |
| A/Indonesia/CDC940/2006 | 2.1.3 | CY017654 | Human | Indonesia | 2006 |
| A/Indonesia/TLL001/2006 | 2.1.3 | EU015403 | Human | Indonesia | 2006 |
| A/Indonesia/TLL002/2006 | 2.1.3 | EU015404 | Human | Indonesia | 2006 |
| A/Indonesia/TLL003/2006 | 2.1.3 | EU015405 | Human | Indonesia | 2006 |
| A/Indonesia/TLL004/2006 | 2.1.3 | EU015406 | Human | Indonesia | 2006 |
| A/Indonesia/TLL005/2006 | 2.1.3 | EU015407 | Human | Indonesia | 2006 |
| A/Indonesia/TLL006/2006 | 2.1.3 | EU015408 | Human | Indonesia | 2006 |
| A/Indonesia/TLL007/2006 | 2.1.3 | EU015409 | Human | Indonesia | 2006 |
| A/Indonesia/TLL008/2006 | 2.1.3 | EU015410 | Human | Indonesia | 2006 |
| A/Indonesia/TLL009/2006 | 2.1.3 | EU015411 | Human | Indonesia | 2006 |
| A/Indonesia/TLL010/2006 | 2.1.3 | EU015412 | Human | Indonesia | 2006 |
| A/Indonesia/TLL011/2006 | 2.1.3 | EU015413 | Human | Indonesia | 2006 |
| A/Indonesia/TLL012/2006 | 2.1.3 | EU015414 | Human | Indonesia | 2006 |
| A/Indonesia/TLL013/2006 | 2.1.3 | EU015415 | Human | Indonesia | 2006 |
| A/Indonesia/TLL014/2006 | 2.1.3 | EU015416 | Human | Indonesia | 2006 |
| A/Djibouti/5691NAMRU3/2006 | 2.2 | DQ666146 | Human | Djibouti | 2006 |
| A/Egypt/7021-NAMRU3/2006 | 2.2 | CY062439 | Human | Egypt | 2006 |
| A/human/Iraq/207-NAMRU3/2006 | 2.2 | DQ435202 | Human | Iraq | 2006 |
| A/Iraq/1/2006 | 2.2 | EU146870 | Human | Iraq | 2006 |
| A/Iraq/659/2006 | 2.2 | EU146876 | Human | Iraq | 2006 |
| A/Iraq/754/2006 | 2.2 | EU146877 | Human | Iraq | 2006 |
| A/Iraq/755/2006 | 2.2 | EU146869 | Human | Iraq | 2006 |
| A/Iraq/756/2006 | 2.2 | EU146878 | Human | Iraq | 2006 |
| A/Turkey/12/2006 | 2.2 | EF619982 | Human | Turkey | 2006 |
| A/Turkey/15/2006 | 2.2 | EF619989 | Human | Turkey | 2006 |
| A/Turkey/651242/2006 | 2.2 | EF619990 | Human | Turkey | 2006 |
| A/Turkey/65596/2006 | 2.2 | EF619998 | Human | Turkey | 2006 |
| A/Xinjiang/1/2006 | 2.2 | FJ492886 | Human | China | 2006 |
| A/Egypt/14724-NAMRU3/2006 | 2.2.1 | EF200512 | Human | Egypt | 2006 |
| A/Egypt/14725-NAMRU3/2006 | 2.2.1 | EF200513 | Human | Egypt | 2006 |
| A/Egypt/2782-NAMRU3/2006 | 2.2.1 | DQ464377 | Human | Egypt | 2006 |
| A/Egypt/2991-NAMRU3/2006 | 2.2.1 | EU095023 | Human | Egypt | 2006 |
| A/Egypt/2992-NAMRU3/2006 | 2.2.1 | EU095024 | Human | Egypt | 2006 |
| A/Egypt/902782/2006 | 2.2.1 | EU146867 | Human | Egypt | 2006 |
| A/Egypt/902786/2006 | 2.2.1 | EU146868 | Human | Egypt | 2006 |
| A/Anhui/1/2005 | 2.3.4 | DQ371928 | Human | China | 2005 |
| A/Anhui/2/2005 | 2.3.4 | DQ371929 | Human | China | 2005 |
| A/China/2006 | 2.3.4 | EF624256 | Human | China | 2006 |
| A/China/GD01/2006 | 2.3.4 | DQ835313 | Human | China | 2006 |
| A/Fujian/1/2005 | 2.3.4 | FJ492882 | Human | China | 2005 |

TABLE 1-continued

COBRA input sequences

| Strain | Clade | Accession | Host | Country | Year |
|---|---|---|---|---|---|
| A/Guangdong/1/2006 | 2.3.4 | FJ492884 | Human | China | 2006 |
| A/Guangxi/1/2005 | 2.3.4 | DQ371930 | Human | China | 2005 |
| A/human/China/GD02/2006 | 2.3.4 | EU263981 | Human | China | 2006 |
| A/Hunan/1/2006 | 2.3.4 | FJ492879 | Human | China | 2006 |
| A/Jiangxi/1/2005 | 2.3.4 | FJ492885 | Human | China | 2005 |
| A/Shanghai/1/2006 | 2.3.4 | AB462295 | Human | China | 2006 |
| A/Shenzhen/406H/2006 | 2.3.4 | EF137706 | Human | China | 2006 |
| A/Sichuan/1/2006 | 2.3.4 | FJ492881 | Human | China | 2006 |
| A/Vietnam/UT30850/2005 | 2.3.4 | HM114537 | Human | Viet Nam | 2005 |
| A/Zhejiang/1/2006 | 2.3.4 | FJ492880 | Human | China | 2006 |
| A/Zhejiang/16/2006 | 2.3.4 | DQ643809 | Human | China | 2006 |

COBRA HA Antigenic Modeling

Influenza hemagglutinin (HA) protein sequences representing COBRA, A/Indonesia/5/2005 (Clade 2.1), A/Whooper Swan/Mongolia/244/2005 (Clade 2.2) and A/Anhui/1/2005 (Clade 2.3) were submitted to the 3D-JIG-SAW Protein Comparative Modeling website for rendering (Bates et al., *Proteins* 45(S5):39-46, 2001; Bates and Sternberg, *Proteins* 37(53):47-54, 1999; Contreras-Moreira and Bates, *Bioinformatics* 18(8):1141-1142, 2002). Structures were overlaid and analyzed using Swiss-Pdb viewer software (Guex and Peitsch, *Electrophoresis* 18(15):2714-23, 1998). Antigenic regions and designations are based on the original description of the antigenic structure of the H3N2 virus A/Hong Kong/1/1968 (Wiley et al., *Nature* 289(5796):373-378, 1981). No significant alterations were observed in region B of the COBRA HA relative to the primary influenza isolates; however, some divergent structures in HA regions A and C were identified in primary isolates.

In Vitro Expression

COBRA HA protein expression was confirmed by transfecting mammalian cells. Human embryonic kidney (HEK) 293T cells ($1 \times 10^6$) were transiently transfected with 3 µg of DNA expressing COBRA. Cells were incubated for 72 hours at 37° C., supernatants were removed, the cells were lysed with 1% Triton-X 100 and cell lysates were collected. Cell lysates were electrophoresed on a 10% SDS-PAGE gel and transferred to a PVDF membrane. The blot was probed with mouse polyclonal antisera pooled from mice infected with 6:2 reassortant H5N1 viruses with the surface glycoproteins derived from either A/Vietnam/1203/2004 or A/Whooper Swan/244/2005, and the HA-antibody complexes were detected using a goat anti-mouse IgG conjugated to horse radish peroxidase (HRP) (Southern Biotech; Birmingham, Ala., USA). HRP was detected by chemiluminescent substrate (Pierce Biotechnology; Rockford Ill., USA) and exposed to X-ray film (ThermoFisher; Pittsburgh, Pa., USA).

COBRA HA Functional Characterization

To determine receptor binding characteristics, virus-like particles (VLPs) containing COBRA HA proteins were purified from the supernatants of mammalian cell lines. HEK 293T cells were transiently transfected with plasmids expressing HIV Gag, COBRA HA and neuraminidase (NA, A/Thailand/1(KAN-1)/2004) and incubated for 72 hours at 37° C. Supernatants were collected and VLPs were purified via ultracentrifugation (100,000×g through 20% glycerol, weight per volume) for 4 hours at 4° C. The pellets were subsequently resuspended in phosphate buffered saline PBS, pH 7.2 and stored at –80° C. until use. Protein concentration was determined by Micro BCA™ Protein Assay Reagent Kit (Pierce Biotechnology, Rockford, Ill., USA). COBRA HA VLPs were prepared in various amounts as measured by total protein and each individual preparation was two-fold serially diluted in v-bottom microtiter plates. An equal volume of either 1% turkey or 1% horse erythrocytes (RBC) (Lampire; Pipersville, Pa., USA) in PBS was added to the diluted VLPs and incubated for 30-60 minutes at room temperature. The HA titer was determined by the reciprocal dilution of the last well which contained agglutinated RBC.

To determine endosomal fusion characteristics. COBRA-pseudotyped lentiviral vectors expressing a luciferase reporter gene were produced as described (Yang et al., *J Virol* 78(8):4029-4036). Briefly, 293T cells were co-transfected by using the following plasmids: 7 µg of pCMVdeltaR8.2, 7 µg of pHRCMV-Luc, 3 µg pCMV/R N1(Kan-1) and 3 µg pTR600 COBRA. Cells were transiently transfected and incubated for 72 hours at 37° C. Supernatants were harvested, centrifuged to clear cell debris, filtered through a 0.22 µm syringe filter, aliquotted, and used immediately or frozen at –80° C. For fusion assays, 100 µl of pseudoviruses were added to confluent MDCK cells in 48-well plates (~30,000 cells per well). Plates were incubated at room temperature for 30 minutes, washed, and fresh medium added. Forty-eight hours after infection, cells were lysed in mammalian cell lysis buffer (Promega; Madison, Wis., USA). A standard quantity of cell lysate was used in a luciferase assay with luciferase assay reagent (Promega; Madison, Wis., USA) according to the manufacturer's protocol.

Vaccine Preparation and Dose Determination

HEK 293T cells were transiently transfected with plasmids expressing M1 (A/Puerto Rico/8/1934, optimized for expression in mammalian cells; SEQ ID NO: 9), NA (A/Thailand/1(KAN-1)/2004, optimized for expression in mammalian cells; SEQ ID NO: 8) and COBRA HA (SEQ ID NO: 7) and incubated for 72 hours at 37° C. Supernatants were collected and cell debris removed by low speed centrifugation followed by vacuum filtration through a 0.22 µm sterile filter. VLPs were purified via ultracentrifugation (100,000×g through 20% glycerol, weight per volume) for 4 hours at 4° C. The pellets were subsequently resuspended in PBS pH 7.2 and stored in single use aliquots at –80° C. until use. Total protein concentration was determined by Micro BCA™ Protein Assay Reagent Kit (Pierce Biotechnology, Rockford, Ill., USA).

HA specific content was determined by western blot and densitometry. Purified recombinant COBRA HA and purified VLPs were prepared in standard total protein amounts and were electrophoresed on a 10% SDS-PAGE gel and transferred to a PVDF membrane. The blot was probed with mouse polyclonal antisera pooled from mice infected with 6:2 reassortant H5N1 viruses with the surface glycoproteins derived from either A/Vietnam/1203/2004 or A/Whooper Swan/244/2005 and the HA-antibody complexes were detected using a goat anti-mouse IgG conjugated to horse radish peroxidase (HRP) (Southern Biotech; Birmingham, Ala., USA). HRP was detected by chemiluminescent substrate (Pierce Biotechnology; Rockford Ill., USA) and exposed to X-ray film (ThermoFisher; Pittsburgh, Pa., USA). Density of bands was determined using ImageJ software (NIH) (Abramoff et al., *Biophotonics International* 11(7):36-42, 2004). Density of recombinant HA bands were used to calculate a standard curve and the density of the purified VLPs was interpolated using the results from the recombinant HA. Experiments were performed in triplicate and multiple exposure times were analyzed for all iterations.

Codon-Optimized Influenza HA, NA and M1 Genes

The nucleotide sequences of the codon-optimized HA (SEQ ID NO: 1), codon-optimized NA (SEQ ID NO: 3) and codon-optimized M1 (SEQ ID NO: 5) genes are set forth in the Sequence Listing. The corresponding amino acid sequences of the encoded HA, NA and M1 proteins are set forth in the Sequence Listing as SEQ ID NO: 2, SEQ ID NO: 4 and SEQ ID NO: 6, respectively.

Mouse Studies

BALB/c mice (*Mus musculis*, females, 6-8 weeks old) were purchased from Harlan Sprague Dawley (Indianapolis, Ind., USA) and housed in microisolator units and allowed free access to food and water and were cared for under USDA guidelines for laboratory animals. Mice (5 mice per group) were vaccinated with one of three doses of purified COBRA HA VLPs (1.5 µg, 0.3 µg or 0.06 µg), based upon HA content from a densitometry assay, via intramuscular injection at week 0 and then boosted with the same dose at week 3. For comparison studies, mice (20 mice per group) were vaccinated with purified VLPs (3 µg) via intramuscular injection at week 0 and then boosted with the same dose at week 3. Vaccines at each dose were formulated with Imject® alum adjuvant (Imject® Alum, Pierce Biotechnology; Rockford, Ill., USA) according to the manufacturer's protocol or vehicle alone. Fourteen to twenty-one days after each vaccination, blood was collected from anesthetized mice via the retro-orbital plexus and transferred to a microfuge tube. Tubes were centrifuged and sera was removed and frozen at −20±5° C.

Three weeks after final vaccination, mice were challenged intranasally with $5 \times 10^3$ plaque forming units (PFU) of the highly pathogenic H5N1 virus A/Whooper Swan/Mongolia/244/2005 (clade 2.2) in a volume of 50 µl. The challenge dose represents approximately 50 $LD_{50}$ in mice. After infection, mice were monitored daily for weight loss, disease signs and death for 14 days after infection. Individual body weights, sickness scores and death were recorded for each group on each day after inoculation. Sickness score was determined by evaluating activity (0=normal, 1=reduced, 2=severely reduced), hunched back (0=absent, 1=present) and ruffled fur (0=absent, 1=present) (Toapanta and Ross, Respiratory Res 10(1):112, 2009). Experimental endpoint was defined as >20% weight loss or display of neurological disease such as hind limb paralysis. All H5N1 influenza virus studies were performed under high-containment biosafety level 3 enhanced conditions (BSL3+).

Ferret Studies

Fitch ferrets (*Mustela putorius faro*, female, 6-12-months of age), influenza naïve and de-scented, were purchased from Marshall Farms (Sayre, Pa., USA). Ferrets were pair housed in stainless steel cages (Shor-line, Kansas City, Kans., USA) containing Sani-chips Laboratory Animal Bedding (P.J. Murphy Forest Products, Montville, N.J., USA). Ferrets were provided with Teklad Global Ferret Diet (Harlan Teklad, Madison, Wis., USA) and fresh water ad libitum. The COBRA HA VLPs were diluted in PBS, pH 7.2 to achieve final concentration. Ferrets (n=3) were vaccinated with 15 kg of purified COBRA VLPs, based upon HA content as determined by densitometry assay, via intramuscular injection in the quadriceps muscle in a volume of 0.25 ml at week 0 and then boosted with the same dose at week 3. Vaccines were stored at −80° C. prior to use and formulated with Imject® alum adjuvant (Imject® Alum; Pierce Biotechnology, Rockford, Ill., USA) immediately prior to use. Animals were monitored for adverse events including weight loss, temperature, loss of activity, nasal discharge, sneezing and diarrhea weekly during the vaccination regimen. Prior to vaccination, animals were confirmed by HAI assay to be seronegative for circulating influenza A (H1N1 and H3N2) and influenza B viruses. Fourteen to twenty-one days after each vaccination, blood was collected from anesthetized ferrets via the anterior vena cava and transferred to a microfuge tube. Tubes were centrifuged and sera was removed and frozen at −20±5° C.

Three weeks after final vaccination, ferrets were challenged intranasally with $1 \times 10^6$ plaque forming units (PFU) of the highly pathogenic H5N1 virus A/Whooper Swan/Mongolia/244/2005 (clade 2.2) in a volume of 0.5 ml in each nostril for a total infection volume of 1 ml. After infection, ferrets were monitored daily for weight loss, disease signs and death for 14 days after infection. Individual body weights, sickness scores, and death were recorded for each group on each day after inoculation. Sickness score was determined by evaluating activity (0=normal, 1=alert and active with stimulation, 2=alert but not active after stimulation, 3=not alert or active after stimulation), nasal discharge (0=absent, 1=present), sneezing (0=absent, 1=present), decreased food intake (0=absent, 1=present), diarrhea (0=absent, 1=present), dyspnea (0=absent, 1=present) and neurological symptoms (0=absent, 1=present). Nasal washes were performed by instilling 3 ml of PBS into the nares of anesthetized ferrets each day for 14 days after inoculation. Washes were collected and stored at −80° C. until use. Experimental endpoint was defined as >20% weight loss, development of neurological symptoms, or an activity score of 3 (not active or alert after stimulation). All H5N1 influenza virus studies were performed under high-containment biosafety level 3 enhanced conditions (BSL3+).

ELISA

The ELISA assay was used to assess total antibody titer and IgG isotype titer to the HA. High binding, 96-well polystyrene plates (Costar; Lowell, Mass., USA) were coated overnight with 50 ng/well of recombinant HA. Coating antigens were derived from the following representative viral isolates: A/Vietnam/1203/2004 (clade 1), A/Indonesia/5/2005 (clade 2.1), A/Whooper Swan/244/2005 (clade 2.2) and A/Anhui/1/2005 (clade 2.3). Plates were blocked with 5% milk diluted in PBS with 0.05% Tween 20. Serum samples were diluted in blocking buffer and added to plates. Serum was two-fold serially diluted and allowed to incubate for 1 hour at room temperature. Plates were washed and species specific antibody against IgG, IgG1, IgG2a, IgG2b or IgG3 and linked to horseradish peroxidase (HRP) (Southern Biotech; Birmingham, Ala., USA) were diluted in blocking buffer and added to plates. Plates were incubated for 1 hour at room temperature. Plates were washed and HRP was developed with TMB substrate (Sigma-Aldrich; St. Louis, Mo., USA). Plates were incubated in the dark for 15 minutes and then the reaction was stopped with 2N $H_2SO_4$. Optical densities at a wavelength of 450 nm ($OD_{450}$) were read by a spectrophotometer (BioTek; Winooski, Vt., USA) and end point dilution titers were determined. End point titers were determined as the reciprocal dilution of the last well which had an $OD_{450}$ above the mean $OD_{450}$ plus two standard deviations of naïve animal sera.

Hemagglutination Inhibition (HAI)

The HAI assay was used to assess functional antibodies to HA able to inhibit agglutination of horse erythrocytes. The protocol was adapted from the CDC laboratory-based influenza surveillance manual (Gillim-Ross and Subbarao, *Clin Microbiol Rev* 19(4):614-636, 2006). To inactivate non-specific inhibitors, sera were treated with receptor destroying enzyme (RDE; Denka Seiken, Co., Japan) prior to being tested (Bright et al. *Lancet* 366(9492):1175-1181, 2005; Bright et al., *Virology* 308(2):270-278, 2003; Bright et al., *JAMA* 295(8):891-894, 2006; Mitchell et al., *Vaccine* 21(9-10):902-914, 2004; Ross et al., *Nat Immunol* 1(2):127-131, 2000). Briefly, three parts RDE was added to one part sera and incubated overnight at 37° C. RDE was inactivated by incubation at 56° C. for ~30 minutes. RDE-treated sera was two-fold serially diluted in v-bottom microtiter plates. An equal volume of reassortant virus, adjusted to approximately 8 HAU/50 was added to each well. The reassortant viruses contained the internal genes from the mouse adapted strain A/Puerto Rico/8/1934 and the surface proteins HA and NA from the following representative viral isolates: A/Vietnam/1203/2004 (clade 1), A/Indonesia/5/2005 (clade 2.1), A/Whooper Swan/244/2005 (clade 2.2) and A/Anhui/1/2005 (clade 2.3). The plates were covered and incubated at room temperature for 20 minutes followed by the addition of 1% horse erythrocytes (hRBC) (Lampire Biologicals, Pipersville, Pa., USA) in PBS. Red blood cells were stored at 4° C. and used within 72 hours of preparation. The plates were mixed by agitation, covered, and the RBCs were allowed to settle for 1 hour at room temperature (Askonas B, McMichael A, Webster R. The immune response to influenza viruses and the problem of protection against infection. In: Beare A S, editor. Basic and applied influenza research: CRC Press 1982: 159-188). The HAI titer was determined by the reciprocal dilution of the last row which contained non-agglutinated RBCs. Positive and negative serum controls were included for each plate. All mice were negative (HAI≤1:10) for pre-existing antibodies to currently circulating human influenza viruses prior to vaccination.

Plaque Assay

Madin-Darby Canine Kidney (MDCK) cells were plated ($5 \times 10^5$) in each well of a 6-well plate. Samples were diluted (final dilution factors of $10^0$ to $10^{-6}$) and overlayed onto the cells in 100 µl of DMEM supplemented with penicillin-streptomycin and incubated for 1 hour. Samples were removed, cells were washed twice and media was replaced with 2 ml of L15 medium plus 0.8% agarose (Cambrex; East Rutherford, N.J., USA) and incubated for 72 hours at 37° C. with 5% $CO_2$. Agarose was removed and discarded. Cells were fixed with 10% buffered formalin, and then stained with 1% crystal violet for 15 minutes. Following thorough washing in $dH_2O$ to remove excess crystal violet, plates were allowed to dry, plaques counted, and the plaque forming units (PFU)/ml were calculated.

Statistical Analysis

Statistical significance of the antibody data was determined using a two-way analysis of variance (ANOVA) with Bonferroni's post-test to analyze differences between each vaccine group for the different test antigens (multiparametric). Differences in weight loss, sickness score, and viral titers were analyzed by two-way ANOVA, followed by Bonferroni's post test for each vaccine group at multiple time points. Significance was defined as $p<0.05$. Statistical analyses were done using GraphPad Prism software.

Results

Computationally Optimized Broadly Reactive Antigen Design

Figure 1B:
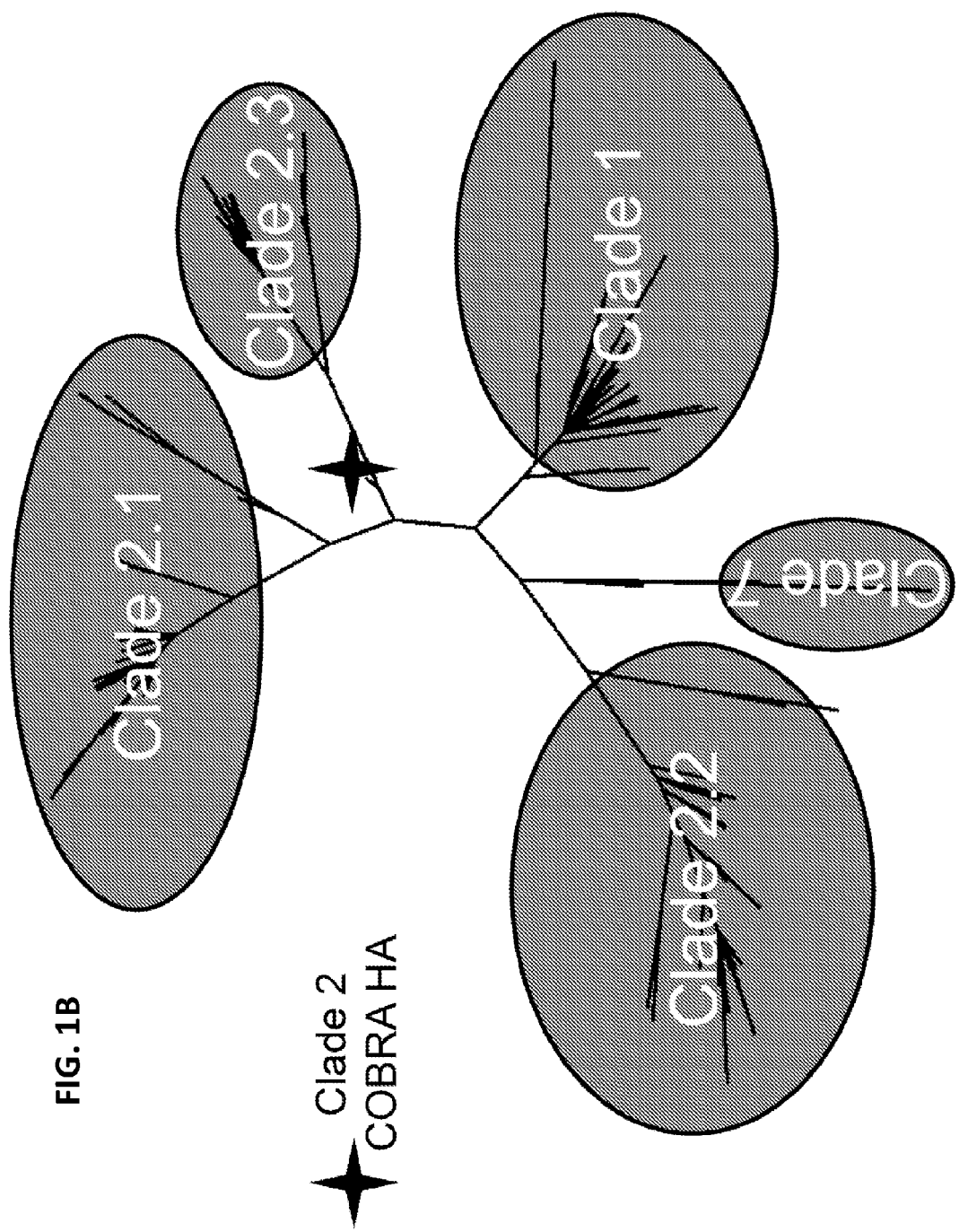

To address the challenge of antigenic diversity present in H5N1 influenza, a computationally optimized broadly reactive antigen (COBRA) was designed. For the first step of antigen generation, 129 unique hemagglutinin (HA) sequences were downloaded from the NCBI Influenza Virus Resource (IVR) sequence database (Bao et al., *J Virol* 82:596-601, 2008) representing clade 2 H5N1 viruses isolated from human infections between 2004 and 2006. The sequences were first grouped into phylogenetic sub-clades and then further divided into individual outbreak groups within each sub-clade based upon geographic location and time of isolation. HA amino acid sequences for each individual outbreak group were aligned and the most common amino acid at each position was determined resulting in primary consensus sequences representing each outbreak group within each sub-clade (FIG. 1A). Primary consensus sequences within each sub-clade were then aligned and the most common amino acid was chosen resulting in secondary consensus sequences representing each sub-clade (FIG. 1A). The secondary consensus sequences were aligned and the most common amino acid at each position was selected resulting in the final consensus sequence referred to as clade 2 COBRA HA (FIG. 1A). Phylogenetic analysis of the COBRA HA with all human isolates of H5N1 HA proteins indicated that COBRA retained a clade 2-like sequence without being grouped specifically within any clade 2 sub-clade cluster (FIG. 1B). Furthermore, a BLAST search using the COBRA HA sequence revealed that it is a unique sequence that has not been isolated from the environment.

Characterization of COBRA

Figure 2A:
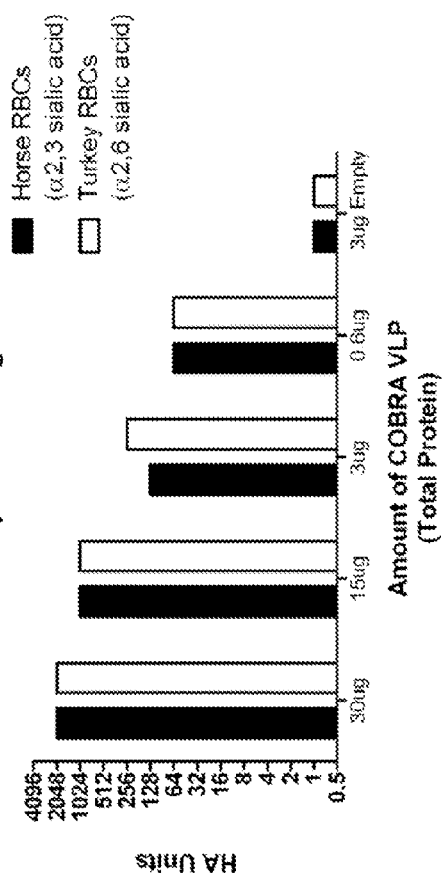
FIGS. 2A-2C: COBRA HA Functional Characterization. COBRA HA was translated in vitro and the cell culture lysates were analyzed by SDS-PAGE (A). Lane designations: 1) H5N1 recombinant HA; 2) COBRA HA; 3) Expression vector; 4) H5N1 reassortant virus. The COBRA HA (lane 2) migrates at its expected molecular weight confirming expression of the synthetic protein. COBRA HA VLPs were prepared in various amounts, serially diluted, and incubated with 1% erythrocytes to evaluate receptor binding (B). HA titer was determined as the last well in which the RBCs remained suspended in a lattice structure. COBRA HA and control lentiviral pseudoparticles packaging a CMV-Luc gene were
Figure 2B:
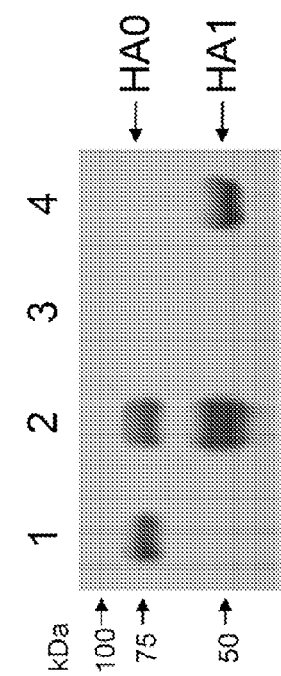

Since COBRA is a fully synthetic protein, the retention of natural hemagglutinin function was confirmed. Initially, COBRA expression was verified by transient transfection of mammalian cells. Analysis of the total cell lysate demonstrated that the COBRA HA migrates at its predicted molecular weight of approximately 73 kDa (FIG. 2A). Because the poly-basic cleavage site was retained in the COBRA HA sequence, both HA0 and the HA1 subunits were detected by immunoblot at similar molecular weights as recombinant HA and the HA on the H5N1 virion (FIG. 2A). Virus-like particles (VLPs) with COBRA HA on the surface bound sialic acid in a dose-dependent manner and this binding was specific to COBRA, since empty lentiviral core alone did not bind to the receptor (FIG. 2B).

Figure 2C:
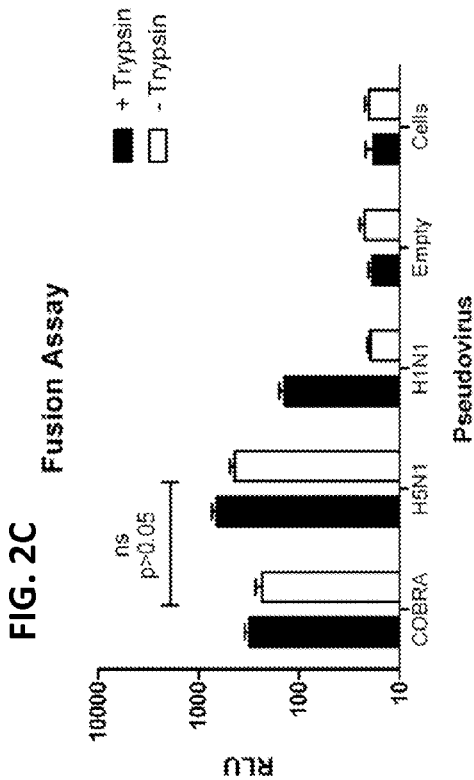

To determine if the COBRA HA was functional, the protein was pseudotyped onto lentiviral $Gag_{p24}$ to generate pseudoparticles (Nefkens et al., *J Clin Virol* 39(1):27-33, 2007; Haynes et al., *Vaccine* 27(4):530-541, 2009). COBRA HA containing pseudoparticles mediated cell fusion as efficiently as H5N1 control pseudoparticles without the requirement for trypsin. In contrast, H1N1 pseudoparticles did require trypsin and pseudoparticles without surface HA produced luciferase at similar levels as the cell only controls (FIG. 2C). Taken together, these results demonstrate that although the COBRA HA is a synthetic protein not found in nature, it retains all of the functions of a natural hemagglutinin protein.

Mouse Dosing Immunizations

Figure 3E:
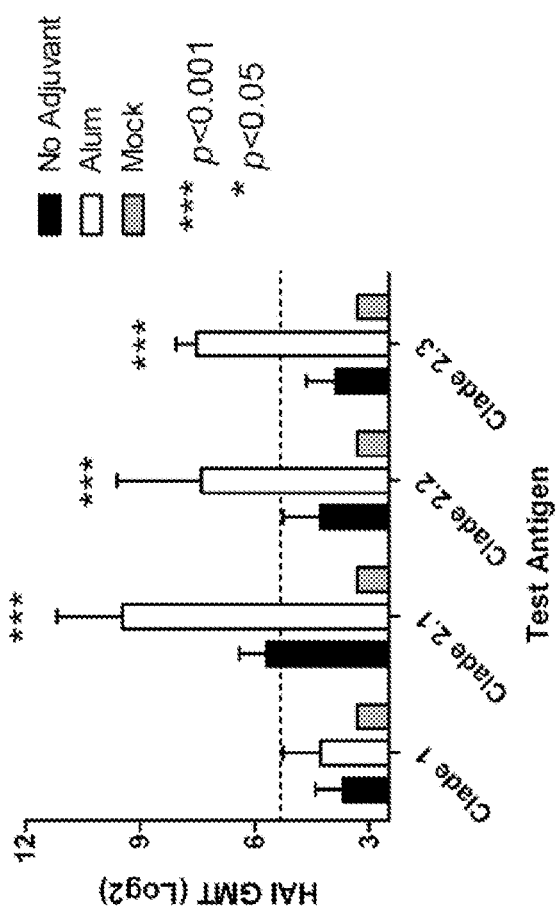
Figure 3F:
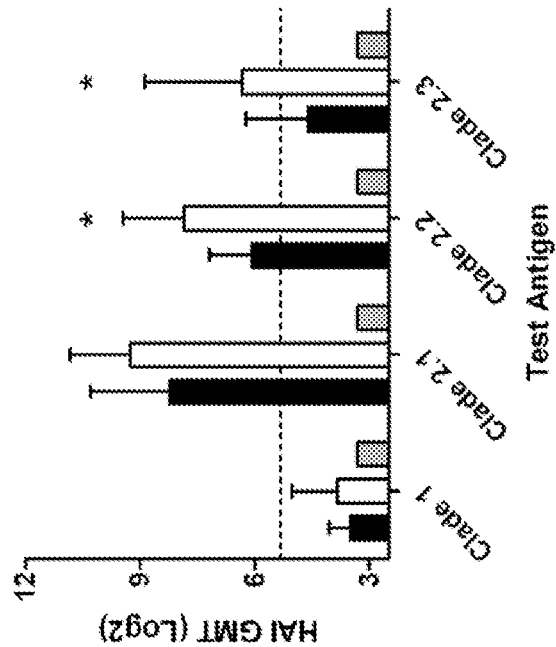

Mice (BALB/c; n=5) were vaccinated (week 0 and 3) via intramuscular injection with purified COBRA VLPs at either a high dose (1.5 µg HA) or low dose (0.3 µg HA) with and without Imject® alum adjuvant. At week 5, all COBRA VLP-vaccinated animals had anti-HA antibodies that recognized heterologous recombinant HA derived from both clade 1 and also sub-clades of clade 2 (FIGS. 3A and 3B). Imject® alum significantly increased anti-HA antibody titers in both low and high dose groups as compared to the non-adjuvanted groups (p<0.01). The IgG isotype subclasses elicited by the VLP vaccines against a clade 2.1 coating antigen consisted mainly of IgG1 and IgG2a, indicating a mixed T helper response (FIGS. 3C and 3D). Similar results were found for additional coating antigens representing clade 1, clade 2.2 and clade 2.3. In addition to recognizing HA, antibodies were also evaluated for the ability to block virus from binding its receptor via inhibition of viral-induced agglutination of horse erythrocytes (HAI). All mice administered Imject® alum adjuvanted vaccines, regardless of dose, had HAI titers ≥1:40 to viruses expressing HA from clades 2.1 and 2.2 and 90% of the mice had titers ≥1:40 to a clade 2.3 representative virus (FIGS. 3E and 3F). Non-adjuvanted vaccines elicited generally lower HAI antibody titers with 100% of high dose animals achieving titers ≥1:40 only against clade 2.1 viruses. Imject® alum adjuvanted vaccines elicited significantly higher HAI antibody titers to clade 2.2 and clade 2.3 viruses regardless of dose as compared to non-adjuvanted vaccines (p<0.05 for high dose and p<0.001 for low dose, respectively). None of the vaccines elicited high HAI titer antibodies to a clade 1 virus.

Mouse Dosing Challenge

Figure 4A:
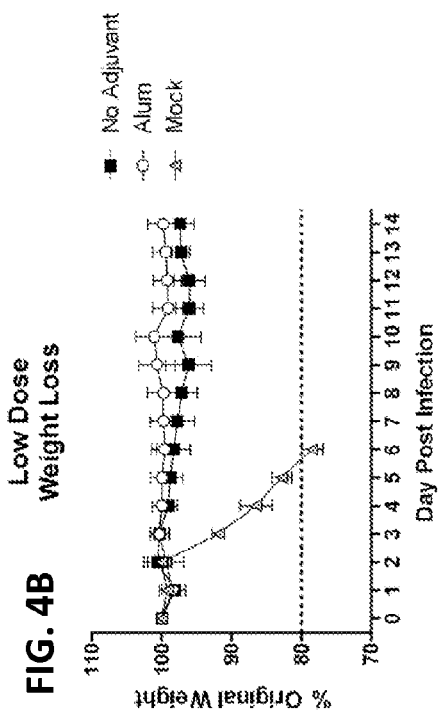
FIGS. 4A-4D: COBRA HA Mouse Dosing Efficacy. BALB/c mice (n=5/group) were vaccinated with COBRA HA VLPs with or without adjuvant. Mice were infected with $5 \times 10^3$ PFU of the highly pathogenic clade 2.2 H5N1 virus A/Whooper Swan/Mongolia/244/2005. Mice were followed to monitor weight loss (A and B) and sickness (C and D). Sickness score was determined by evaluating activity (0=normal, 1=reduced, 2=severely reduced), hunched back (0=absent, 1=present) and ruffled fur (0=absent, 1=present). All mock vaccinated mice reached the experimental endpoint and required euthanasia by 6 days post infection.
Figure 4B:
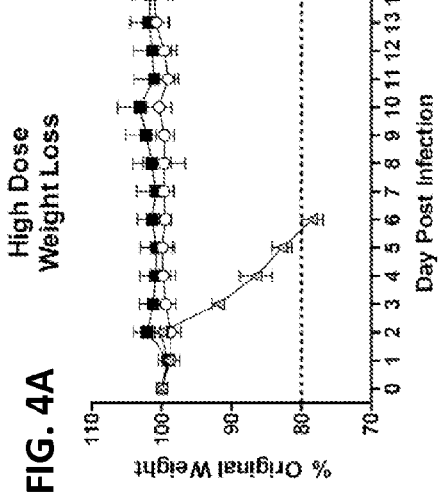
Figure 4C:
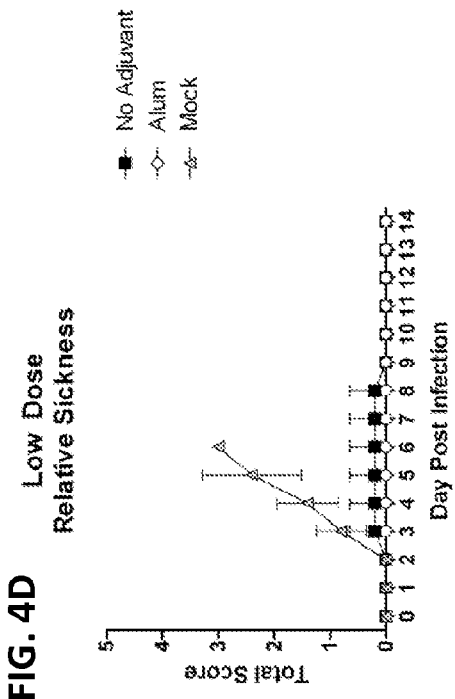
Figure 4D:
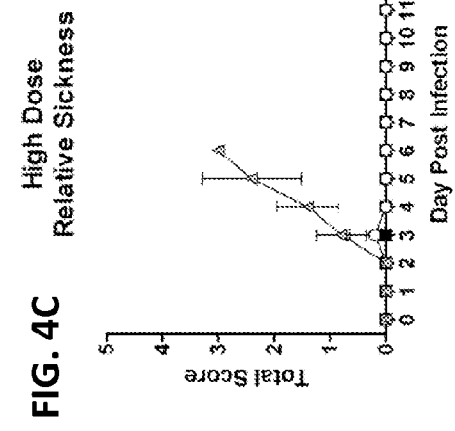

Mice that received the COBRA VLP vaccines or mock vaccinated control mice were challenged intranasally with a lethal dose of clade 2.2 H5N1 highly pathogenic avian influenza (A/Mongolia/whooper swan/244/2005) to evaluate the protective efficacy of the different COBRA vaccine formulations. All COBRA vaccinated mice, regardless of dose or the presence of adjuvant, were protected from weight loss and death following lethal challenge, while all mock vaccinated animals rapidly lost weight and required euthanasia by day 6 post infection (FIGS. 4A and 4B). Additionally, COBRA VLP vaccinated mice had no signs of disease, while mock vaccinated animals developed such symptoms as ruffled fur, hunched back, and lethargy (FIGS. 4C and 4D).

Mouse Comparison Immunizations

Figure 5A:
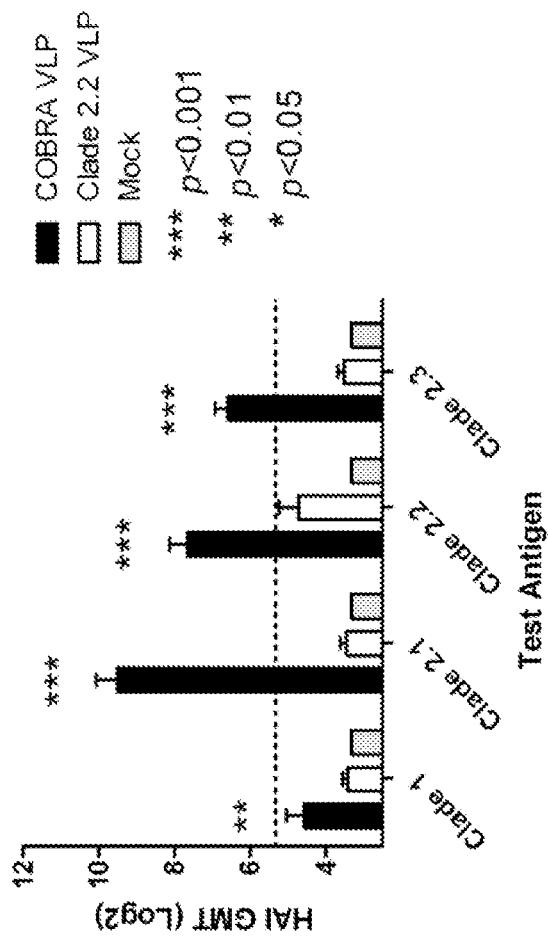
FIGS. 5A-5B: Mouse Comparison Immunogenicity. BALB/c mice (n=20/group) were vaccinated at 0 and 3 weeks with blood collected at 14 to 21 days after each vaccination. Vaccines were formulated at a high dose (3 μg HA) with Imject® alum and delivered intramuscularly. Total IgG at week 5 was determined via ELISA for each vaccine group (A). Values represent the geometric mean titer (±95% confidence interval) of $\log_{10}$ transformed endpoint titers. Hemagglutination inhibition (HAI) serum antibody titer for each vaccine group was determined at week 5 using representative reassortant viruses (B). Values represent the geometric mean titer (±95% confidence interval) of $\log_2$ transformed titers. The dotted line represents the 1:40 titer. Significant differences were determined by two-way ANOVA with Bonferroni's post-test to evaluate differences between the vaccine formulations for each test antigen. A p value of less than 0.05 was considered significant.
Figure 5B:
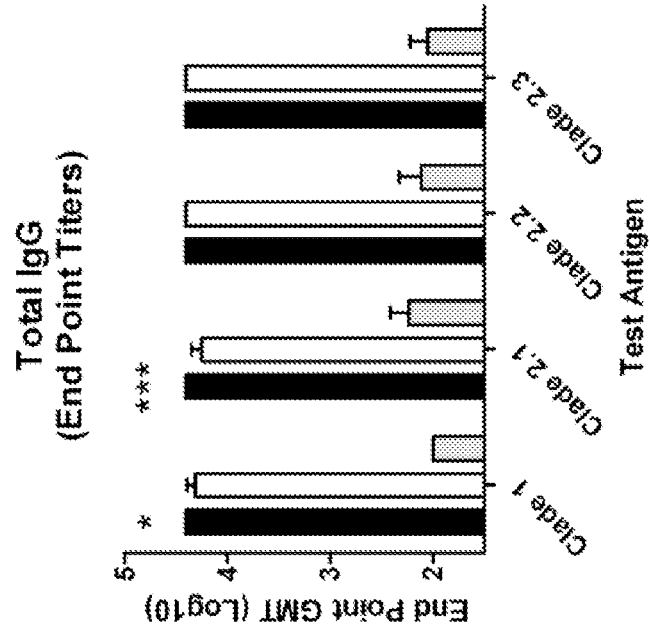

To determine if the COBRA HA vaccine elicits a broader antibody response compared to a vaccine derived from a primary isolate, an additional set of mice were vaccinated with either COBRA VLPs or clade 2.2 (A/Mongolia/whooper swan/244/2005) VLPs. Mice (BALB/c; n=20) were vaccinated (week 0 and 3) via intramuscular injection with either COBRA VLPs or clade 2.2 VLPs at a high dose (3 µg HA) with Imject® alum adjuvant. At week 5, all COBRA VLP-vaccinated mice and all clade 2.2 VLP-vaccinated mice had anti-HA antibodies that recognized heterologous recombinant HA derived from both clade 1 and various sub-clades of clade 2 (FIG. 5A). Although no significant differences were found in total IgG titers between vaccine groups, COBRA VLP-vaccinated animals had higher HAI antibody titers against all viruses tested as compared to clade 2.2 VLP-vaccinated animals (p<0.01; FIG. 5B). Furthermore, COBRA VLP-vaccinated animals had an increased frequency of HAI titers of ≥1:40 compared to clade 2.2 VLP-vaccinated animals (Table 2).

TABLE 2

Mouse seroconversion frequency

| Vaccine Antigen | Clade 1[a] | Clade 2.1[b] | Clade 2.2[c] | Clade 2.3[d] |
|---|---|---|---|---|
| COBRA | 45% (9/20) | 100% (20/20) | 100% (20/20) | 100% (20/20) |
| Clade 2.2[c] | 0% (0/20) | 0% (0/20) | 0% (0/20) | 0% (0/20) |

Percentage of VLP-vaccinated animals achieving an HAI titer of ≥1:40 to each test antigen.
[a]A/Vietnam/1203/2004
[b]A/Indonesia/5/2005
[c]A/Whooper Swan/Mongolia/244/2005
[d]A/Anhui/1/2005

Mouse Comparison Challenge

Figures 6A, 6B:
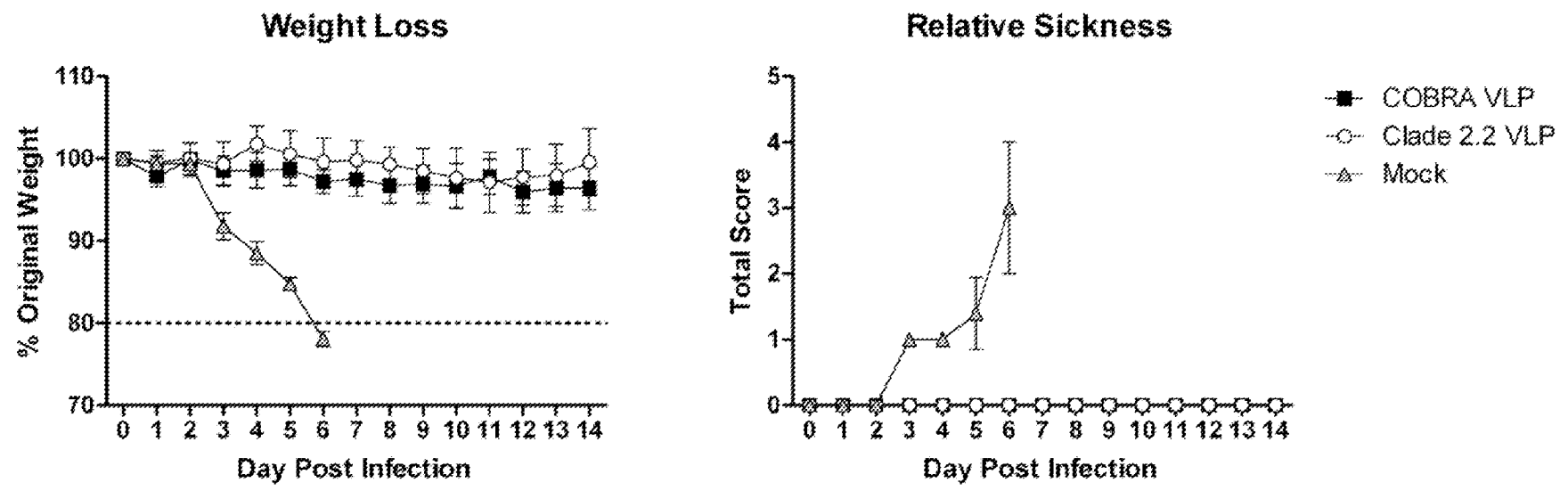

Mice that received the COBRA VLP vaccine, clade 2.2 VLP vaccine or mock vaccinated control mice were challenged intranasally with a lethal dose of clade 2.2 H5N1 highly pathogenic avian influenza (A/Mongolia/whooper swan/244/2005) to evaluate the protective efficacy of the VLP vaccines. All VLP-vaccinated mice were protected from weight loss and death following lethal challenge while all mock vaccinated animals rapidly lost weight and required euthanasia by day 6 post infection (FIG. 6A). Additionally, VLP vaccinated mice did not show signs of disease, while mock vaccinated animals developed ruffled fur, hunched back, and lethargy (FIG. 6B). Even though the clade 2.2 VLP was matched to the challenge virus, no significant differences were found between COBRA VLP and clade 2.2 VLP vaccinated mice in any of the parameters analyzed indicating that the COBRA VLP vaccine protected animals as efficiently as the homologous vaccine.

Ferret Comparison Immunizations

Figure 7A:
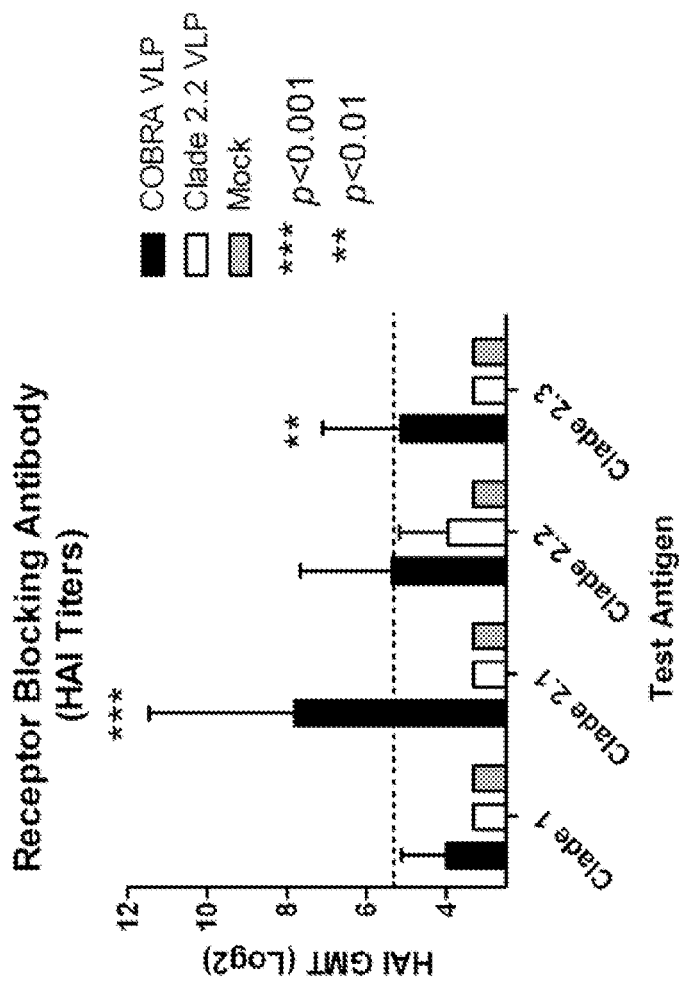
FIGS. 7A-7B: Ferret Immunogenicity. Ferrets (n=9/group) were vaccinated with VLPs (15 mg HA) with Imject® alum at weeks 0 and 3 and serum collected at week 5. Total IgG at week 5 was determined via ELISA for each vaccine group (A). Values represent the geometric mean titer (±95% confidence interval) of $\log_{10}$ transformed endpoint titers. Hemagglutination inhibition (HAI) serum antibody titer for each vaccine group was determined at week 5 using representative reassortant viruses (B). Values represent the geometric mean titer (±95% confidence interval) of $\log_2$ transformed titers. The dotted line represents the 1:40 titer. Significant differences were determined by two-way ANOVA with Bonferroni's post-test to evaluate differences between the vaccine formulations for each test antigen. A p value of less than 0.05 was considered significant.
Figure 7B:
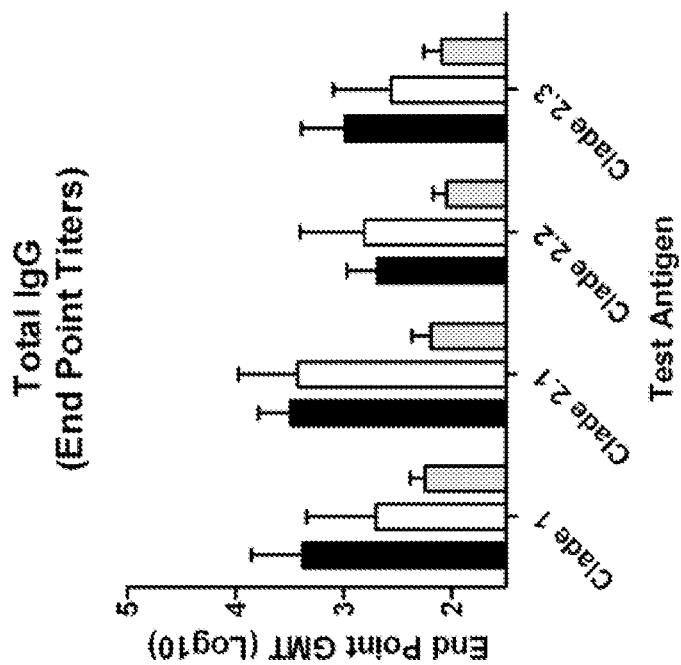

Ferrets are the most relevant model for influenza disease and as such the COBRA vaccine was tested in this more rigorous animal model. Ferrets (Fitch; n=9) were vaccinated (week 0 and 3) via intramuscular injection with COBRA VLPs or clade 2.2 VLPs at a high dose (15 µg HA) with Imject® alum adjuvant. Serum was collected from ferrets at week 5 and antibody responses to the COBRA vaccines were evaluated. All vaccinated ferrets had anti-HA antibodies that recognized heterologous recombinant HA derived from both clade 1 and also sub-clades of clade 2 (FIG. 7A). No significant difference in anti-HA antibody was found between the COBRA VLP vaccine and the clade 2.2 VLP vaccine for any of the antigens tested (p>0.05). In addition to recognizing HA, antibodies were also evaluated for HAI activity. COBRA VLP-vaccinated animals had higher HAI antibody titers against clade 2.1 and clade 2.3 viruses as compared to clade 2.2 VLP-vaccinated animals (p<0.01 FIG. 7B). Similar to the mice, COBRA VLP-vaccinated ferrets displayed an increased rate of achieving HAI titers ≥1:40 when compared to clade 2.2 VLP-vaccinated ferrets (Table 3).

TABLE 3

Ferret seroconversion frequency

| Vaccine Antigen | Clade 1[a] | Clade 2.1[b] | Clade 2.2[c] | Clade 2.3[d] |
|---|---|---|---|---|
| COBRA | 0% (0/9) | 78% (7/9) | 56% (5/9) | 56% (5/9) |
| Clade 2.2[c] | 0% (0/9) | 0% (0/9) | 22% (2/9) | 0% (0/9) |

Percentage of VLP-vaccinated animals achieving an HAI titer of ≥1:40 to each test antigen.
[a]A/Vietnam/1203/2004
[b]A/Indonesia/5/2005
[c]A/Whooper Swan/Mongolia/244/2005
[d]A/Anhui/1/2005

Ferret Comparison Challenge

Ferrets that received the COBRA VLP vaccines, clade 2.2 VLP vaccines or mock vaccinated control animals were challenged intranasally with clade 2.2 H5N1 highly pathogenic avian influenza (A/Mongolia/whooper swan/244/2005) to evaluate the protective efficacy of the COBRA vaccine in the ferret model of influenza infection. All VLP vaccinated ferrets were protected from weight loss and death following viral challenge, while all mock vaccinated animals rapidly lost weight and 78% (7/9) of mock vaccinated animals required euthanasia by day 7 post-infection (FIGS. 8A and 8B). Additionally, both COBRA VLP-vaccinated and clade 2.2-vaccinated ferrets were protected from acute fever and failed to develop significant signs of disease while mock vaccinated animals had an elevated body temperature and developed such symptoms as lethargy, diarrhea and decreased food and water intake (FIGS. 8C and 8D). In addition to monitoring outward signs of disease progression, nasal washes were collected for determination of viral replication in the upper respiratory tract. Ferrets vaccinated with either COBRA VLPs or clade 2.2 VLPs did not have detectable virus at any point after infection, while mock vaccinated animals had high levels of viral replication for the first five days of the infection (FIG. 8E). No significant differences were found between COBRA VLP and clade 2.2 VLP vaccinated ferrets in any of the challenge parameters analyzed confirming the findings in mice that the COBRA VLP vaccine protected animals as efficiently as the homologous vaccine.

The percent identity of COBRA HA and the test antigens used in the mouse and ferret studies described above are shown in Table 4.

TABLE 4

Percent Identity of Test Antigens

| Vaccine Antigen | Clade 1[a] | Clade 2.1[b] | Clade 2.2[c] | Clade 2.3[d] |
|---|---|---|---|---|
| COBRA | 97% | 97% | 95% | 97% |
| Clade 2.2[c] | 94% | 97% | 100% | 94% |

HA amino acid sequences were aligned and percent identity across the entire protein was determined for the vaccine immunogens compared to the representative test antigens.
[a]A/Vietnam/1203/2004
[b]A/Indonesia/5/2005
[c]A/Whooper Swan/Mongolia/244/2005
[d]A/Anhui/1/2005

Example 2

A Computationally-Optimized HA VLP Vaccines Elicits Broadly-Reactive Antibodies that Protect Monkeys from H5N1 Infection This example describes the finding that a COBRA clade 2 HA H5N1 VLP elicits broad humoral immunity against multiple H5N1 isolates from different clades.

Materials and Methods

Expression and Purification of Virus-Like Particles

The COBRA HA sequence is described above in Example 1. 293T cells were transiently transfected with plasmids expressing HA, M1, and NA in low serum media, incubated for 72 h at 37° C., and purified by ultracentrifugation through a 20% glycerol cushion as previously described (Giles and Ross, Vaccine 29:3043-3054, 2011). All VLP vaccines were engineered using the same NA from A/Thailand/1(KAN-1)/2004. HA content was quantified as previously described (Giles and Ross, Vaccine 29:3043-3054, 2011). Two different VLP preparations were purified, each containing one of the HA influenza gene products: WS/05 or the COBRA HA.

Primate Immunizations and H5N1 Challenges

Cynomolgus macaques (Macaca fascicularis, male, 3-5 years old) were vaccinated with 15 µg (based upon HA content) of purified COBRA HA VLPs (n=7) or WS/05 VLPs (n=7), via intramuscular injection at weeks 0, 3 and 6. Vaccines at each dose were formulated with alum adjuvant (Imject® Alum, Pierce Biotechnology; Rockford, Ill., USA) immediately prior to use. Twenty-one days after each vaccination, blood was collected from anesthetized macaques. All procedures were in accordance with the NRC Guide for the Care and Use of Laboratory Animals.

Three weeks after final vaccination, macaques were placed into BSL3+ isolator units (Bioqual, Inc. Rockville, Md.) and then challenged by a multi-route of infection (ocular, nasal, tracheal) as previously described (Kobasa et al., Nature 445: 319-323, 2007; Kuiken et al., Vet Pathol 40:304-310, 2003; Rimmelzwaan et al., Avian Dis 47:931-933, 2003) using $1 \times 10^6$ plaque forming units (PFU) of the highly pathogenic H5N1 virus, A/Whooper Swan/Mongolia/244/2005 (clade 2.2), at each location. Monkeys were monitored daily for weight loss, signs of disease, and mortality until 7 days after infection. Individual body weights, sickness scores (based upon lethargy, temperature change, nasal discharge, lack of appetite, dehydration, lack of responsiveness), and death were recorded for each group.

Nasal and tracheal washes were performed at day 0, 1, 3, 5, and 7 post-infection. In addition, subsets of monkeys were sacrificed following administration of anesthesia and necropsies were performed according to standard procedures for assessment of gross pathologic and histopathologic changes, as well as the extent of virus replication.

Serological Assays

A quantitative ELISA was performed to assess anti-HA specific IgG in immune serum as previously described (Bright et al., PLoS One 3:e1501, 2008; Giles and Ross, Vaccine 29:3043-3054, 2011). The hemagglutination inhibition (HAI) assay was used on sera treated with receptor destroying enzyme (RDE; Denka Seiken, Co., Japan) prior to being tested (Bright et al., Vaccine 25:3871-3878, 2007; Mitchell et al., Vaccine 21:902-914, 2003; Bright et al., PLoS One 3:e1501, 2008) to assess functional antibodies to the HA able to inhibit agglutination of horse red blood (Askonas B, McMichael A, Webster R. The immune response to influenza viruses and the problem of protection against infection. In: Beare A S, editor. Basic and applied influenza research: CRC Press 1982: 159-188). The protocol was adapted from the CDC laboratory-based influenza surveillance manual and performed as previously described (Gillim-Ross and Subbarao, Clin Microbiol Rev 19:614-636, 2006; Bright et al., PLoS One 3:e1501, 2008). The HAI titer was determined by the reciprocal dilution of the last row which contained non-agglutinated RBC. Positive and negative serum controls were included for each plate. All monkeys were negative (HAI≤1:10) for pre-existing antibodies to currently circulating human influenza viruses prior to vaccination. Serum neutralizing antibody titers were determined by microneutralization (MN) assays performed on Madin Darby Canine Kidney (MDCK) cells following the procedure until CPE was observed (Rowe et al., J Clin Microbiol 37:937-943, 1999). Cells were then fixed in 10% formalin and stained with 1% crystal violet to quantify CPE. The neutralizing antibody titers are expressed as the reciprocal of the highest dilution of serum that gave 50% neutralization of 100 $TCID_{50}$ of virus in MDCK cells. Geometric mean neutralizing antibody titers were calculated for each group.

Histopathologic Evaluation and Immunohistochemical Analysis

Formalin-inflated lungs and trachea were fixed in 10% neutral buffered formalin. Cross-sections of upper and lower left and right lung lobes and trachea were made, concentrating on gross-lesions. Tissue was paraffin-embedded and 6-sections were stained with hematoxylin and eosin for histologic evaluation. Sequential sections were processed for immunohistochemistry or in situ hybridization (ISH). Immunohistochemistry was performed as described previously (Bissel et al., *Am J Pathol* 160:927-941, 2002) using an immunoperoxidase method with a polyclonal antibody (Maine Biotechnology Services, Portland, Me.) directed against influenza A virus. A biotinylated donkey anti-goat IgG (Rockland Immunochemicals, Gilbertsville, Pa.) was used as the secondary antibody. ISH was performed as described previously (Fallert et al., *J Virol Methods* 99:23-32, 2002) using a 35S-labeled riboprobe synthesized using templates derived from 760 bp of influenza A/California/04/2009 matrix protein.

Results

Vaccine Induced Antibody Responses

Cynomolgus macaques were vaccinated with COBRA VLPs or WS/05 VLPs formulated with Imject® alum at 0, 3 and 6 weeks. At week 3 post-vaccination, all COBRA VLP-vaccinated animals had anti-HA antibodies that recognized recombinant HA derived from three sub-clades of clade 2, which were boosted at week 6 (FIGS. 10A and 10B). There was no statistical difference (p>0.05) in the anti-HA titers elicited against any of the HA proteins, except monkeys vaccinated with COBRA VLPs had a statistically higher titer against the Indo/05 HA (clade 2.1) compared with monkeys vaccinated with the WS/05 VLP (derived from clade 2.2) on week 6.

Figure 10C:
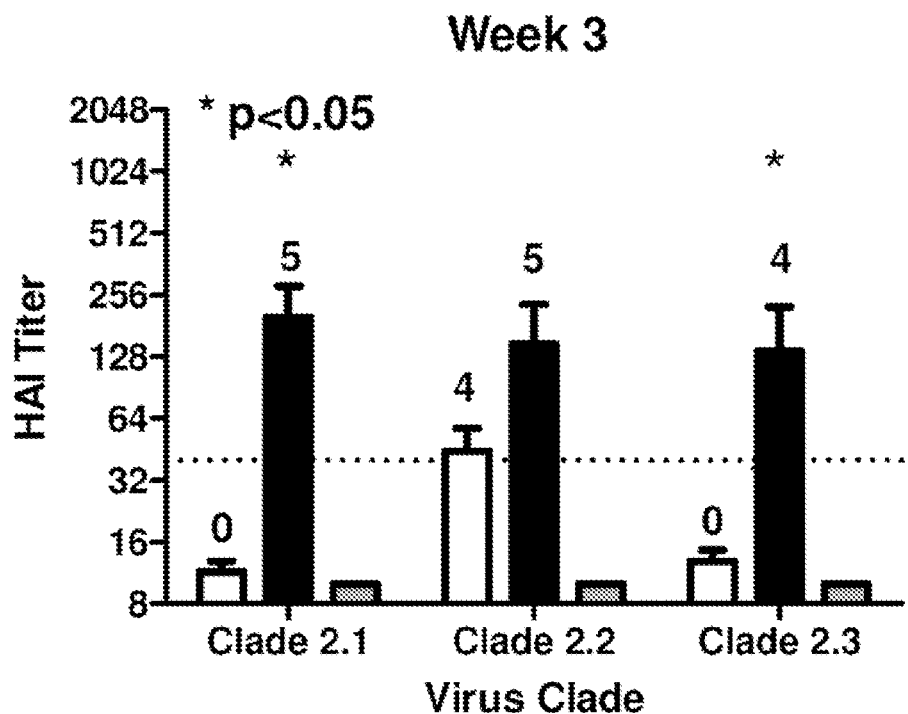
Figure 10D:
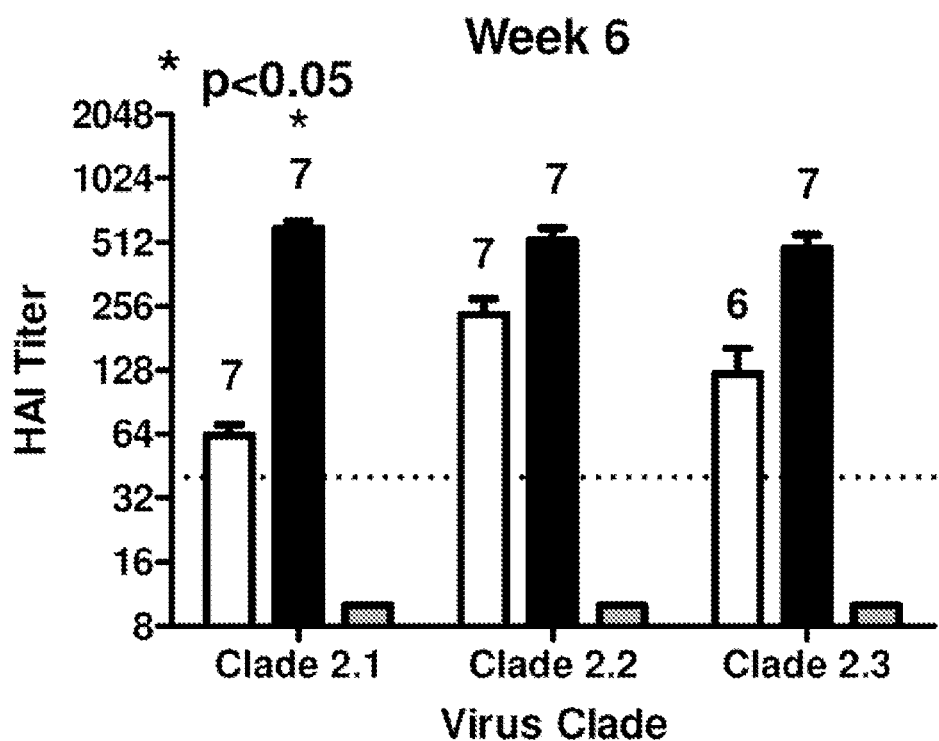
Figure 10E:
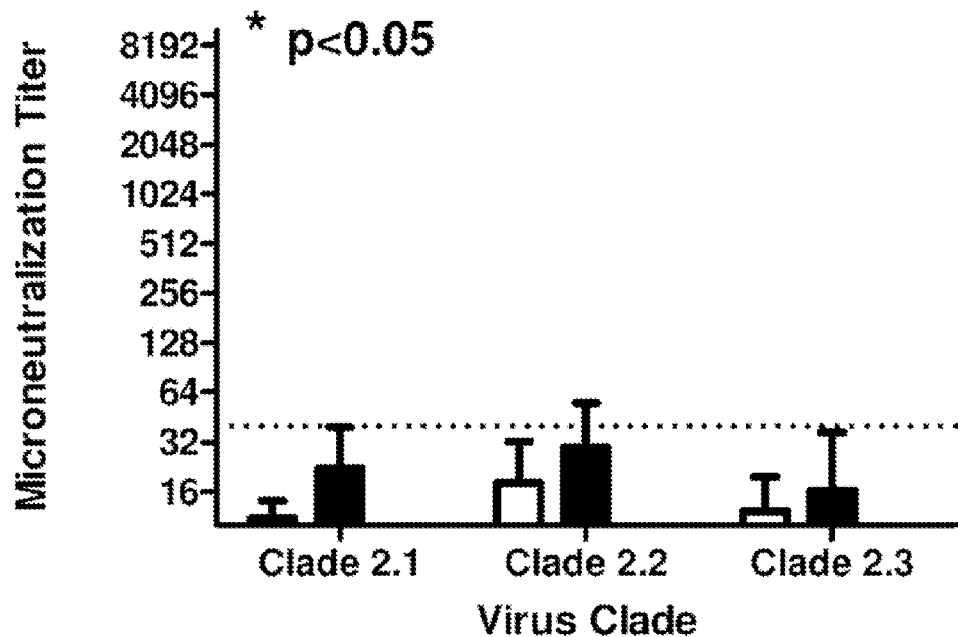
Figure 10F:
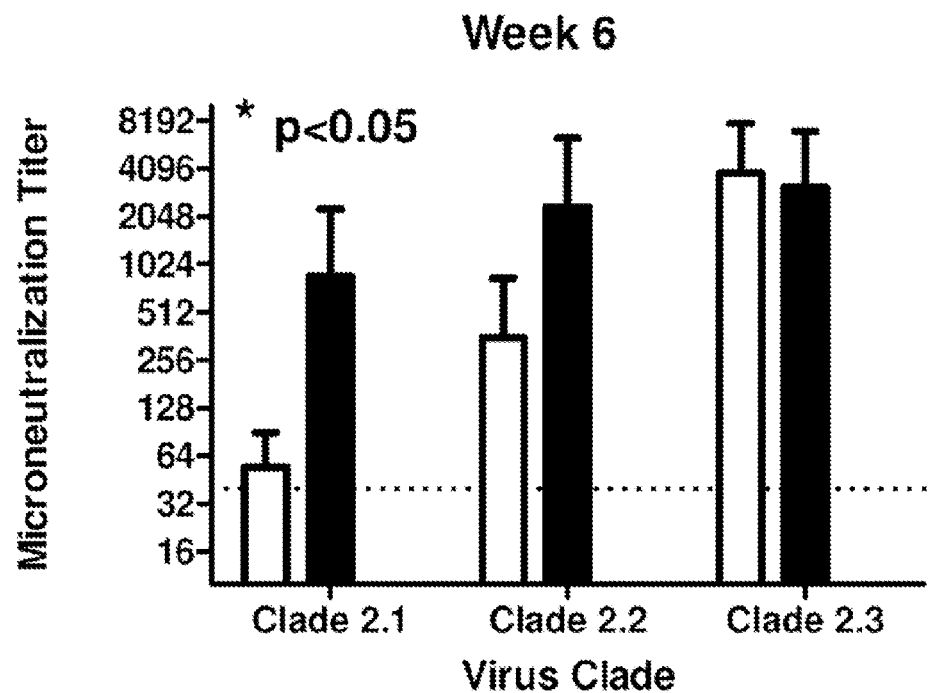
Figure 11:
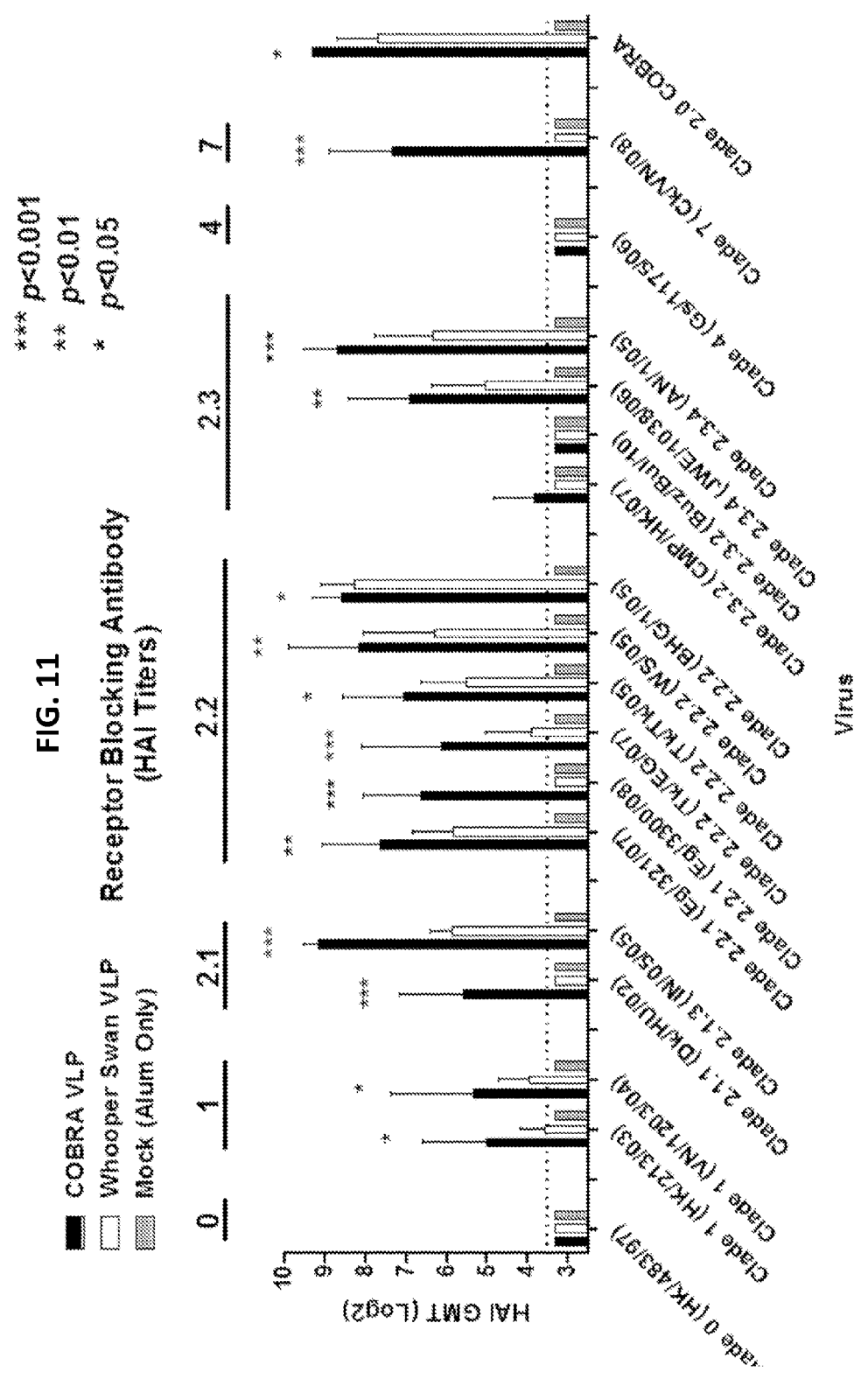

A Single COBRA VLP Vaccination Induced High Titer HAI and MN Antibodies to Clade 2 H5N1 Viruses Monkeys vaccinated with COBRA VLPs (but not with WS/05 VLPs) had HAI activity against viruses representing all three clade 2 sub-clades after a single vaccination (FIG. 10C). Four to six monkeys responded to the COBRA VLP vaccine with an HAI titer ≥1:40 for the all of the various test antigens. In contrast, 4 of 7 monkeys vaccinated with the WS/05 VLP responded to the homologous clade 2.2 virus, but none of these vaccinated monkeys responded to the clade 2.1 or 2.3 virus. Following a second vaccination, almost all the monkeys vaccinated with either vaccine responded to all three viruses (FIG. 11D). These results were confirmed by microneutralization assay (FIGS. 11E and 11F). However, monkeys vaccinated with COBRA VLPs showed boosted HAI titers to all three clade 2 viruses (FIG. 11).

COBRA VLPs Induced HAI Antibodies that Recognize Broader Numbers of H5N1 Viruses In order to determine if the COBRA HA elicited antibodies that recognized a broader number of H5N1 isolates, serum was collected and tested for the ability to inhibit influenza virus induced hemagglutination of red blood cells in vitro. Antisera collected from both vaccinated and unvaccinated monkeys were then tested against a broad panel of H5N1 viruses representing not only sub-clades of clade 2, but also non-clade 2 H5N1 virus strains (0, 1, 4, and 7) by HAI. Monkeys vaccinated with the COBRA VLP had high average HAI titers against all clade 2 isolates, regardless of sub-clade (FIG. 11). In general, all 7 monkeys responded to the COBRA VLP vaccine and seroconverted with an HAI titer ≥1:40 against all the clade 2 viruses. In contrast, monkeys vaccinated with the WS/05 VLP vaccine had lower HAI titers against clade 2 viruses (FIG. 10) and fewer number of monkeys responded to the vaccine. Of the 10 clade 2 viruses tested in the HAI assay, WS/05 VLP vaccinated monkeys responded more poorly (fewer than 4 of 7 monkeys) to 4 of the isolates and none of these monkeys had antibodies that responded to the Dk/HU/02 (clade 2.1.1) or Eg/3300/08 (clade 2.2.1) isolates. The COBRA VLPs elicited significantly higher HAI titers against almost all of the clade 2 viruses than the WS/05 VLPs (FIG. 11).

In addition to clade 2 isolates, a minimum of five COBRA VLP vaccinated monkeys had HAI antibodies against both clade 1 and 7 virus isolates (FIG. 11). In comparison, almost none of the WS/05 VLP vaccinated monkeys had HAI antibodies against clade 1 and clade 7 viruses. None of the monkeys, regardless of the vaccine, had antibodies that responded to the clade 0 or 4 isolates. All mock vaccinated monkeys did not recognize any of the H5N1 isolates.

Challenge of Vaccinated and Unvaccinated Primates with H5N1 Clade 2.2 Virus

Three weeks after final vaccination, both VLP vaccinated and mock-vaccinated monkeys were transferred to ABSL3+ isolator units and then challenged with highly pathogenic H5N1 virus, A/Whooper Swan/Mongolia/244/2005 (clade 2.2) ($1 \times 10^6$ pfu), by a multi-route (ocular, nasal, tracheal, oral) of infection (Kobasa et al., *Nature* 445:319-323, 2007; Kuiken et al., *Vet Pathol* 40:304-310, 2003; Rimmelzwaan et al., *Avian Dis* 47:931-933, 2003). There was no significant weight loss or mortality in any of the monkeys over the 7 day period of observation. Unvaccinated monkeys had an elevated temperature of ~2° C. that was sustained for 5 days post-infection and higher gross pathology scores by day 3 post-infection (Table 5).

TABLE 5

Lung pathology, temperature and viral titer of vaccinated macaques

| Vaccine | Lung Pathology Score (day 3) | Elevated temperature (days) | Peak Viral Titer (pfu/ml) (day) |
|---|---|---|---|
| Mock | 5.3 | 1.9° C. (1-5 DPI) | Nasal wash: 2.2-2.5 (5 DPI) Trachea wash: 2.0-4.4 (3 DPI) |
| WS/05 VLP | 3.3 | 1.1° C.-1.3° C. (1-5 DPI) | Nasal wash: <2 Trachea wash: <2 |
| COBRA VLP | 2.1 | 1.3° C. (2 DPI) | Nasal wash: <2 Trachea wash: <2 |

The lungs of unvaccinated monkeys had mild to moderate acute pneumonia with alveolar pulmonary exudate by day 3 post-infection by H&E staining. ISH showed focal collections of H5N1 infected cells present at day 3 post-infection in alveolar spaces and to a lesser extent in bronchial epithelium. These results were similar to unvaccinated monkeys infected with the clade 1 H5N1 virus, A/Vietnam/1203/2004. In contrast, monkeys vaccinated with either the COBRA VLP or the WS/05 VLP vaccine had a reduced gross pathology scores of 2.1-3.3 at day 3 post-infection with a milder increase in body temperature (1.1-1.3° C.) that spiked between days 2-3 post-infection and then returned to pre-infection temperatures. Vaccinated animals had fewer H5N1 infected cells that were detected primarily on day 1 post-infection (Table 6).

TABLE 6

H5N1 lung infection scores

| Vaccine | | | Alveolar infection score | | | Submucosal infection score | | |
|---|---|---|---|---|---|---|---|---|
| | 1 | 3 | 5 | 1 | 3 | 5 | 1 | 3 | 5 |
| Mock | 1.00 | 0.05 | 0 | 1.10 | 0.48 | 0.25 | 0 | 0 | 0 |
| WS/05 VLP | 0.05 | 0 | 0 | 0.55 | 0.10 | 0 | 0 | 0 | 0 |
| COBRA VLP | 0 | 0 | 0 | 0.60 | 0.03 | 0.05 | 0 | 0 | 0 |

ISH for influenza was performed on tissue sections of from upper and lower left and right lung. A semi-quantitative scoring system was developed to evaluate the presence of influenza infected cells.
Scores were then averaged: 0.2 = rare or occasional cells but <5% of fields; 1 = >½ to ¼ low power fields; 2 = >¼ low power fields; 3 = essentially all low power fields.

However, monkeys vaccinated with the COBRA VLP had little to no signs of lung inflammation by H&E staining, while animals vaccinated with the WS/05 VLP vaccine had similar signs of inflammation as non-vaccinated monkeys (Table 7). In addition, unvaccinated monkeys had high titers of virus in both the nasal and tracheal washes between days 3 and 5 post-infection. In contrast, no virus was detected in either vaccinated groups.

TABLE 7

Lung involvement and inflammation scores

| Vaccine | % lung involvement[a] | | | Bronchial inflammation[b] | | | Alveolar inflammation[b] | | |
|---|---|---|---|---|---|---|---|---|---|
| | 1 | 3 | 5 | 1 | 3 | 5 | 1 | 3 | 5 |
| Mock | 0.38 | 1.13 | 1.25 | 0.63 | 0.75 | 1.25 | 0.63 | 1.00 | 1.25 |
| | (0-1) | (0-2) | (0-2) | (0-1) | (0-2) | (0-2) | (0-1) | (0-2) | (0-2) |
| WS/05 VLP | 0.75 | 1.50 | 0.88 | 1.00 | 1.42 | 0.63 | 1.00 | 1.25 | 1.00 |
| | (0-2) | (0-3) | (0-3) | (1) | (1-2) | (0-2) | (0-2) | (0-2) | (0-2) |
| COBRA VLP | 0.88 | 0.50 | 0.38 | 1.13 | 0.75 | 0.88 | 1.13 | 0.67 | 0.25 |
| | (0-2) | (0-2) | (0-2) | (1-2) | (0-2) | (0-2) | (0-2) | (0-2) | (0-1) |

[a]% Lung involvement. Tissue sections from upper and lower left and right lung were evaluated for percent area demonstrating pneumonia. Scores were then averaged. Range in parentheses. 0 = <10%, 1 = 10-24%, 2 = 25-50%, 3 = >50%.
[b]Bronchial and alveolar inflammation scores. Tissue sections from upper and lower left and right lung were evaluated for presence of bronchial inflammation and denudation and alveolar immune cell infiltration. Scores were then averages: 0 = absent, 1 = present, 2 = abundant.

Example 3

Comparison of Protective Efficacy by Vaccination with Computationally Optimized HA and Polyvalent HA Based H5N1 VLP Vaccines This example describes a comparison of the COBRA HA vaccine to a polyvalent H5N1 vaccine. The results demonstrate that a single COBRA antigen elicits broader antibodies and is more effective than a polyvalent mixture of primary antigens.

Materials and Methods

Vaccine Antigens and Preparation

The design and characterization of the computationally optimized broadly reactive antigen (COBRA) is described in Example 1. Polyvalent vaccine HA antigens were derived via reverse transcription from the following 6:2 reassortant H5N1 viruses: A/Indonesia/5/2005 (clade 2.1; IN/05), A/Whooper Swan/Mongolia/244/2005 (clade 2.2; WS/05) and A/Anhui/1/2005 (clade 2.3; AN/05). All HA antigens were cloned into the pTR600 expression vector.

Virus-like particles (VLPs) were generated by transiently transfecting HEK 293T cells with plasmids expressing M1 (A/Puerto Rico/8/1934), NA (A/Thailand/1(KAN-1)/2004), and a single HA for each preparation. Cells were incubated for 72 h at 37° C. after which supernatants were harvested. Cell debris was cleared by low speed centrifugation followed by vacuum filtration through a 0.22 jam sterile filter. VLPs were purified by ultracentrifugation (100,000×g through 20% glycerol, weight to volume) for 4 hours at 4° C. Pellets were then resuspended in PBS pH 7.2 and stored in single use aliquots at −80° C. until use. Total protein concentration was determined by MicroBCA™ Protein Assay Reagent Kit (Pierce Biotechnology, Rockford, Ill., USA). HA specific content of each VLP was determined by scanning densitometry as described previously (Giles and Ross, *Vaccine* 29:3043-3054, 2011). Briefly, purified HA matched to each VLP was electrophoresed with purified VLPs, transferred to a PVDF membrane and probed by western blot with H5-specific antisera. The relative density of the HA band in the purified protein lanes was used to calculate a standard curve and the density of the HA in the VLP lanes was interpolated. In total, four different VLP preparations were purified and HA content quantified independently, each containing one of the three wild-type influenza gene products (1N/05, WS/05, AN/05) or the COBRA HA.

Mouse Studies

BALB/c mice (*Mus musculis*, females, 6-8 weeks) were purchased from Harlan Sprague Dawley, (Indianapolis, Ind., USA) and housed in microisolator units and allowed free access to food and water and were cared for under USDA guidelines for laboratory animals. Mice were vaccinated with purified COBRA VLPs (3 μg HA) or a polyvalent formulation of VLPs consisting of 1 μg HA each 1N/05, WS/05 and AN/05 (3 μg HA total) via intramuscular injection at week 0 and then boosted at week 3. Vaccines were formulated with Imject® alum adjuvant (Imject® Alum, Pierce Biotechnology; Rockford, Ill., USA) according to the manufacturer's protocol. Fourteen to twenty-one days after each vaccination, blood was collected from anesthetized mice via the retro-orbital plexus and transferred to a microfuge tube. Tubes were centrifuged and sera was removed and frozen at −20±5° C.

Three weeks after final vaccination, mice were challenged intranasally with $5 \times 10^3$ plaque forming units (PFU) of either highly pathogenic wild type H5N1 virus A/Whooper Swan/Mongolia/244/2005 (n=20/group) or 6:2 reassortant virus with internal genes from the mouse adapted virus A/Puerto Rico/8/1934 and the surface proteins HA and NA from A/Vietnam/1203/2004 (n=10/group) in a total volume of Challenge doses for both viruses were established independently and represent approximately 50 $LD_{50}$. After infection, mice were monitored daily for weight loss, disease signs and death for 14 days after infection. Individual body weights, sickness scores and death were recorded for each group on each day after inoculation. Sickness score was determined by evaluating activity (0=normal, 1=reduced, 2=severely reduced), hunched back (0=absent, 1=present) and ruffled fur (0=absent, 1=present) (Toapanta and Ross, *Respiratory Res* 10(1):112, 2009). Experimental endpoint was determined by >20% weight loss or display of neurological disease such as hind limb paralysis. All highly pathogenic wild type H5N1 influenza virus studies were performed under high-containment biosafety level 3 enhanced conditions (BSL3+).

Ferret Studies

Fitch ferrets (*Mustela putorius faro*, female, 6-12-months of age), influenza naïve and descented, were purchased from Marshall Farms (Sayre, Pa., USA). Ferrets were pair housed in stainless steel cages (Shor-line, Kansas City, Kans., USA)

containing Sani-chips Laboratory Animal Bedding (P.J. Murphy Forest Products, Montville, N.J., USA). Ferrets were provided with Teklad Global Ferret Diet (Harlan Teklad, Madison, Wis., USA) and fresh water ad libitum. The VLPs were diluted in PBS, pH 7.2 to achieve final concentration. Ferrets (n=6) were vaccinated with purified COBRA VLPs (15 µg HA) or a polyvalent formulation of VLPs consisting of 5 µg HA each IN/05, WS/05 and AN/05 (15 µg HA total) via intramuscular injection at week 0 and then boosted at week 3. Vaccines were formulated with Imject® alum adjuvant (Imject® Alum, Pierce Biotechnology; Rockford, Ill., USA) immediately prior to use according to the manufacturer's protocol. Animals were monitored for adverse events including weight loss, temperature, loss of activity, nasal discharge, sneezing and diarrhea weekly during the vaccination regimen. Prior to vaccination, animals were confirmed by HAI assay to be seronegative for circulating influenza A (H1N1 and H3N2) and influenza B viruses. Fourteen to twenty-one days after each vaccination, blood was collected from anesthetized ferrets via the anterior vena cava and transferred to a microfuge tube. Tubes were centrifuged and sera was removed and frozen at −20±5° C.

Three weeks after final vaccination, ferrets were challenged intranasally with $1\times10^6$ plaque forming units (PFU) of the highly pathogenic H5N1 virus A/Whooper Swan/Mongolia/244/2005 (clade 2.2) in a volume of 0.5 ml in each nostril for a total infection volume of 1 ml. After infection, ferrets were monitored daily for weight loss, disease signs and death for 14 days after infection. Individual body weights, sickness scores, and death were recorded for each group on each day after inoculation. Sickness score was determined by evaluating activity (0=normal, 1=alert and active after stimulation, 2=alert but not active after stimulation, 3=neither active nor alert after stimulation), nasal discharge (0=absent, 1=present), sneezing (0=absent, 1=present), decreased food intake (0=absent, 1=present), diarrhea (0=absent, 1=present), dyspnea (0=absent, 1=present) and neurological symptoms (0=absent, 1=present) as previously described (Giles and Ross, *Vaccine* 29:3043-3054, 2011). Experimental endpoint was defined as >20% weight loss, development of neurological disease or an activity score of 3 (neither active nor alert after stimulation). Nasal washes were performed by instilling 3 ml of PBS into the nares of anesthetized ferrets each day for 14 days after inoculation. Washes were collected and stored at −80° C. until use. All highly pathogenic wild type H5N1 influenza virus studies were performed under high-containment biosafety level 3 enhanced conditions (BSL3+).

ELISA Assay

The ELISA assay was used to assess total antibody titer to the HA. High binding, 96-well polystyrene plates (Costar; Lowell, Mass., USA) were coated overnight with 50 ng/well of recombinant HA. Coating antigens were derived from the following representative viral isolates: A/Vietnam/1203/2004 (clade 1), A/Indonesia/5/2005 (clade 2.1), A/Whooper Swan/Mongolia/244/2005 (clade 2.2) and A/Anhui/1/2005 (clade 2.3). Plates were blocked with 5% milk diluted in PBS with 0.05% Tween 20. Serum samples were diluted in blocking buffer and added to plates. Serum was two-fold serially diluted and allowed to incubate for 1 hour at room temperature. Plates were washed and species specific antibody against IgG linked to horseradish peroxidase (HRP) was diluted in blocking buffer and added to plates. Plates were incubated for 1 hour at room temperature. Plates were washed and HRP was developed with TMB substrate (Sigma-Aldrich; St. Louis, Mo., USA). Plates were incubated in the dark for 15 minutes and then the reaction was stopped with 2N $H_2SO_4$. Optical densities at a wavelength of 450 nm ($OD_{450}$) were read by a spectrophotometer (BioTek; Winooski, Vt., USA) and end point dilution titers were determined as the reciprocal dilution of the last well which had an $OD_{450}$ above the mean $OD_{450}$ plus two standard deviations of naïve animal sera.

Hemagglutination Inhibition (HAI) Assay

The HAI assay was used to assess functional antibodies to the HA able to inhibit agglutination of horse erythrocytes. The protocol was adapted from the CDC laboratory-based influenza surveillance manual (Gillim-Ross and Subbarao, *Clin Microbiol Rev* 19(4):614-636, 2006). To inactivate non-specific inhibitors, sera were treated with receptor destroying enzyme (RDE; Denka Seiken, Co., Japan) prior to being tested. Briefly, three parts RDE was added to one part sera and incubated overnight at 37° C. RDE was inactivated by incubation at 56° C. for ~30 min. RDE treated sera was two-fold serially diluted in v-bottom microtiter plates. An equal volume of reassortant virus, adjusted to approximately 8 HAU/50 µl, was added to each well. The reassortant viruses contained the internal genes from the mouse adapted strain A/Puerto Rico/8/1934 and the surface proteins HA and NA from the following representative viral isolates: A/Vietnam/1203/2004 (clade 1), A/Indonesia/5/2005 (clade 2.1), A/Whooper Swan/Mongolia/244/2005 (clade 2.2) and A/Anhui/1/2005 (clade 2.3). The plates were covered and incubated at room temperature for 20 minutes followed by the addition of 1% horse erythrocytes (HRBC) (Lampire Biologicals, Pipersville, Pa., USA) in PBS. Red blood cells were stored at 4° C. and used within 72 h of preparation. The plates were mixed by agitation, covered, and the RBCs were allowed to settle for 1 h at room temperature (Askonas B, McMichael A, Webster R. The immune response to influenza viruses and the problem of protection against infection. In: Beare A S, editor. Basic and applied influenza research: CRC Press 1982: 159-188). The HAI titer was determined by the reciprocal dilution of the last well which contained non-agglutinated RBC. Positive and negative serum controls were included for each plate. All mice and ferrets were negative (HAI≤1:10) for pre-existing antibodies to currently circulating human influenza viruses prior to vaccination.

Plaque Assay

For mouse infections, lung virus titers were evaluated. For ferret infections, nasal wash virus titers were used to assess viral burden. Both lungs and nasal wash virus titers were determined using a plaque assay (Tobita et al., *Med Microbiol Immunol* 162:23-27, 1975; Tobita et al., *Med Microbial Immunol* 162:9-14, 1975). Briefly, lungs from mice infected with virus were harvested post infection, snap-frozen and stored at −80° C. until use. Samples were thawed, weighed and single cell suspensions were prepared via passage through a 70 µm mesh (BD Falcon, Bedford, Mass., USA) in an appropriate volume of DMEM supplemented with penicillin-streptomycin (iDEME) as to achieve 100 mg/ml final concentration. Cell suspensions were centrifuged at 2000 rpm for 5 minutes and the supernatants were collected.

Madin-Darby Canine Kidney (MDCK) cells were plated ($5\times10^5$) in each well of a 6 well plate. Samples (lung supernatants for mice and nasal washes for ferrets) were diluted (dilution factors of $1\times10^1$ to $10^6$) and overlayed onto the cells in 100 µl of iDMEM and incubated for 1 hour. Virus-containing medium was removed and replaced with 2 ml of L15 medium plus 0.8% agarose (Cambrex, East Rutherford, N.J., USA) and incubated for 96 hours at 37° C. with 5% $CO_2$. Agarose was removed and discarded. Cells were fixed with 10% buffered formalin, and then stained with 1% crystal violet for 15 minutes. Following thorough washing in $dH_2O$ to remove excess crystal violet, plates were allowed to dry, plaques counted, and the plaque forming units (PFU)/g for or PFU/ml for nasal washes were calculated.

Histopathological Analysis

Left lobes of lungs from infected mice were collected 4 days post-infection and placed into 10% buffered formalin. After fixation, lungs were paraffin embedded and 6 μm sections were prepared for histopathological analysis. For in situ hybridization (ISH), vectors containing 760 bp of Influenza/California/04/2009 matrix protein were linearized to create antisense and sense templates. $^{35}$S-labeled riboprobes were generated using MAXIscript in vitro transcription kit (Ambion, Austin, Tex.). ISH was performed as described before (Bissel et al., *Brain Pathol, Accepted Article doi:* 10.1111/j.1750-3639.2010.00514.x). Control riboprobes did not hybridize to lung tissue at any time point post-infection and non-infected tissue did not show hybridization with viral probes. Hybridized slides were assessed and scored for abundance of foci.

Cellular Assays

The number of anti-influenza specific cells secreting interferon gamma (IFN-γ) was determined by enzyme-linked immunospot (ELISpot) assay (R&D systems, Minneapolis, Minn., USA) following the manufacturer's protocol. Mice were sacrificed at 6 days post infection (DPI) and spleens and lungs were harvested and prepared in single cell suspensions. Briefly, pre-coated anti-IFNγ plates were blocked with RPMI plus 10% FCS and antibiotics (cRPMI) for 30 minutes at room temperature. Media was removed from wells and $10^5$ cells were added to each well. Cells were stimulated with purified recombinant HA from A/Vietnam/1203/2004 (truncated at residue 530; 1 μg/well), inactivated 6:2 reassortant virus A/Vietnam/1203/2004 (1:100 dilution of inactivated stock; 100 μl/well) or the immunodominant H2-K$^d$ CD8+ T cell epitope in H5 HA: HA$_{533}$ (IYSTVASSL; SEQ ID NO: 10; 1 μg/well) (Pepscan Presto, Leystad, Netherlands). Additional wells were stimulated with PMA (50 ng/well) and ionomycin (500 ng/well) as positive controls or Ova$_{257}$ (SIINFEKL; SEQ ID NO: 11; 1 μg/well) (Pepscan Presto, Leystad, Netherlands) as negative controls. Additionally, IL-2 (10 U/ml) was added to each well. Plates were incubated at 37° C. for 48 hours. After incubation, plates were washed four times with R&D wash buffer and were incubated at 4° C. overnight with biotinylated anti-mouse IFNγ. Plates were washed as before and incubated at room temperature for 2 hours with streptavidin conjugated to alkaline phosphatase. Plates were washed as before and spots were developed by incubating at room temperature for 1 hour in the dark with BCIP/NBT chromogen substrate. The plates were washed extensively with DI H$_2$O and allowed to dry overnight prior to spots being counted using an ImmunoSpot ELISpot reader (Cellular Technology Ltd., Cleveland, Ohio, USA).

The number of anti-HA and anti-NA specific antibody secreting cells was determined by B cell ELISpot assay as previously described (Joo et al., *Vaccine* 28:2186-2194, 2009; Sasaki et al., *PLoS ONE* 3:e2975, 2008; Sasaki et al., *J Virol* 81:215-228, 2007). Mice were sacrificed at 6 DPI and spleens and lungs were harvested and prepared in single cell suspensions. Briefly, 0.45 μm PVDF membrane plates (Millipore, Billerica, Mass., USA) were coated with either purified recombinant HA from A/Vietnam/1203/2004 or purified recombinant NA from A/Thailand/1 (KAN-1)/2004 (250 ng/well) and incubated at 4° C. overnight. Plates were washed three times with PBS and blocked with cRPMI for at 37° C. for 3-4 hours. Media was removed from wells and $10^5$ cells were added to each well. Plates were incubated at 37° C. for 48 hours. After incubation, plates were washed as before and incubated at room temperature for 2 hours with horse radish peroxidase conjugated anti-mouse IgG or IgA (Southern Biotech, Birmingham, Ala., USA). Plates were washed as before and spots were developed at room temperature for 1 hour in the dark with detection substrate (NovaRED™; Vector Labs, Burlingame, Calif., USA). The plates were washed extensively with DI H$_2$O and allowed to dry overnight prior to spots being counted using an ImmunoSpot ELISpot reader (Cellular Technology Ltd., Cleveland, Ohio, USA).

Passive Transfer of Sera

Serum from vaccinated mice was pooled and passively transferred into 9 week old recipient BALB/c mice (n=5/group). Equal amounts of serum from each mouse in a particular vaccine group were pooled and heat inactivated for 30 minutes at 56° C. 200 μl of pooled and inactivated serum was transferred to recipient mice via IP injection. 24 hours post transfer, mice were infected with 6:2 reassortant virus with internal genes from the mouse adapted virus A/Puerto Rico/8/1934 and surface antigens from A/Vietnam/1203/2004.

Statistical Analysis

Statistical significance of the antibody and cellular immunology data was determined using a two-tailed Student's T test to analyze differences between COBRA and polyvalent vaccine groups for each of the different test antigens. Differences in weight loss and sickness score were analyzed by two-way ANOVA, followed by Bonferroni's post test for each vaccine group at multiple time points (multiparametric). Statistical significance of viral titer data was evaluated using a two-tailed Student's T test on Log$_{10}$ transformed values. Significance was defined as p<0.05. Statistical analyses were done using GraphPad Prism software.

Results

Immunogenicity in Mice and Ferrets

BALB/c mice were vaccinated twice via intramuscular injection with either purified COBRA or polyvalent VLPs and two weeks after the second vaccination serum was analyzed for antibody responses. All vaccinated mice had high titer anti-HA antibodies that bound to recombinant HA derived from both clade 1 and various sub-clades of clade 2 (FIG. 12A). Although both COBRA and polyvalent vaccines elicited similar total IgG, COBRA vaccinated animals had higher HAI antibody titers for all viruses tested (p<0.001; FIG. 12B). In addition to higher HAI titer, COBRA vaccinated mice had an increased frequency of HAI titers ≥1:40 for all viruses tested, including those which were components of the polyvalent formulation (Table 8).

To confirm the results from mice in a more rigorous animal model, ferrets were vaccinated twice via intramuscular injection with either COBRA or polyvalent vaccines. Serum was collected two weeks after the second vaccination and antibody responses were evaluated. Similar to the mice, all vaccinated ferrets had anti-HA antibodies that bound to diverse recombinant HA and the relative total IgG titers were equivalent for both COBRA and polyvalent vaccines (FIG. 12C). COBRA vaccinated ferrets demonstrated increased HAI antibody titers compared to polyvalent vaccinated animals against all viruses tested, however only the antibodies to the clade 2.1 virus were significantly different (p<0.05; FIG. 12D). Furthermore, COBRA vaccinated animals displayed an increased rate of achieving an HAI titer of ≥1:40 in comparison to the polyvalent vaccinated ferrets for all test antigens (Table 8).

TABLE 8

| | | Seroconversion frequency | | | |
|---|---|---|---|---|---|
| Species | Vaccine antigen | Clade 1 | Clade 2.1 | Clade 2.2 | Clade 2.3 |
| Mouse | COBRA | 60% (18/30) | 100% (30/30) | 100% (30/30) | 100% (30/30) |
| | Polyvalent | 3.3% (1/30) | 70% (21/30) | 50% (15/30) | 53% (16/30) |
| Ferret | COBRA | 33% (2/6) | 67% (4/6) | 50% (3/6) | 50% (3/6) |
| | Polyvalent | 0% (0/6) | 33% (2/6) | 0% (0/6) | 0% (0/6) |

Wild Type Clade 2.2 Challenge

To confirm protective efficacy against highly pathogenic H5N1 infection, vaccinated animals were challenged with a lethal dose of the wild-type clade 2.2 isolate A/Whooper Swan/Mongolia/244/2005. All VLP vaccinated mice were protected from weight loss and death while mock vaccinated animals rapidly lost weight and reached experimental endpoint by 6 days post infection (DPI; FIG. 13A). COBRA and polyvalent vaccinated mice both had a mean maximum weight loss of 4% at 12 and 13 DPI, respectively. Additionally, all VLP vaccinated mice failed to develop any overt signs of disease while mock vaccinated mice developed visible illness (FIG. 13B).

Similar to the mice, all VLP vaccinated ferrets were protected from death following a lethal challenge. Vaccinated ferrets demonstrated mild weight loss in response to the infection with COBRA vaccinated animals having mean maximum weight loss of 5.5% at 2 DPI and polyvalent vaccinated animals losing 6.8% at 3 DPI (FIG. 13C). Both groups rapidly recovered weight and failed to develop any significant signs of disease (FIG. 13D). Furthermore, VLP vaccinated animals did not demonstrate any temperature spikes while mock vaccinated animals had an elevated temperature of ~3° C. for 1-3 DPI.

Figure 14A:
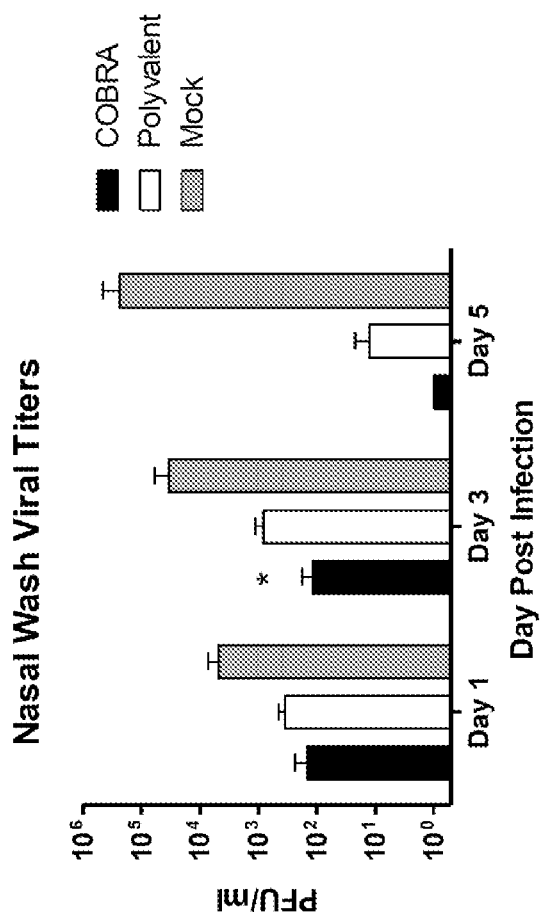
Figure 14B:
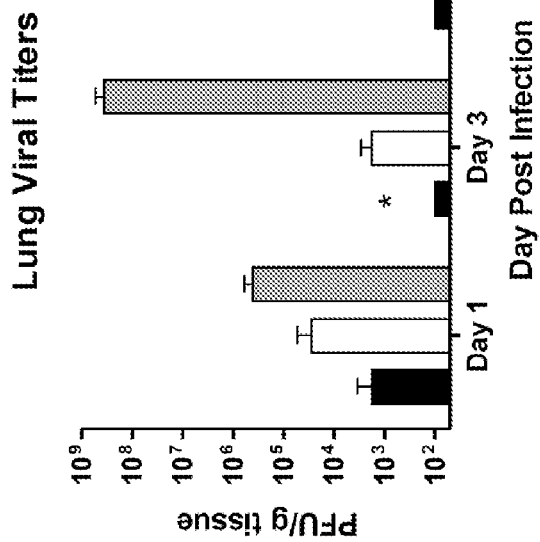

To evaluate vaccine efficacy with a more sensitive output than morbidity and mortality, the viral burden of infected animals was also determined. Both COBRA and polyvalent vaccinated mice had reduced lung viral titers as quickly as 1 DPI when compared to mock vaccinated animals. Furthermore, COBRA vaccinated mice did not have detectable virus by 3 DPI while polyvalent vaccinated mice demonstrated prolonged viral replication with $1.8 \times 10^3$ PFU/g at 3 DPI ($p<0.05$; FIG. 14A). Additionally, both VLP vaccines prevented extra-pulmonary spread of the virus while mock vaccinated animals had detectable virus in both kidney and liver by 3 DPI. Control of virus replication in ferrets was similar to that observed in mice, although complete clearance of the virus was delayed (FIG. 14B). All VLP vaccinated animals had decreased recovery of virus in nasal washes compared to mock vaccinated ferrets at all timepoints tested ($p<0.05$). COBRA vaccinated animals did not have detectable virus by 5 DPI. In contrast, virus replication did not reach undetectable levels until 9 DPI in polyvalent vaccinated ferrets.

Histopathology of Infected Lungs

Figures 15A, 15B:
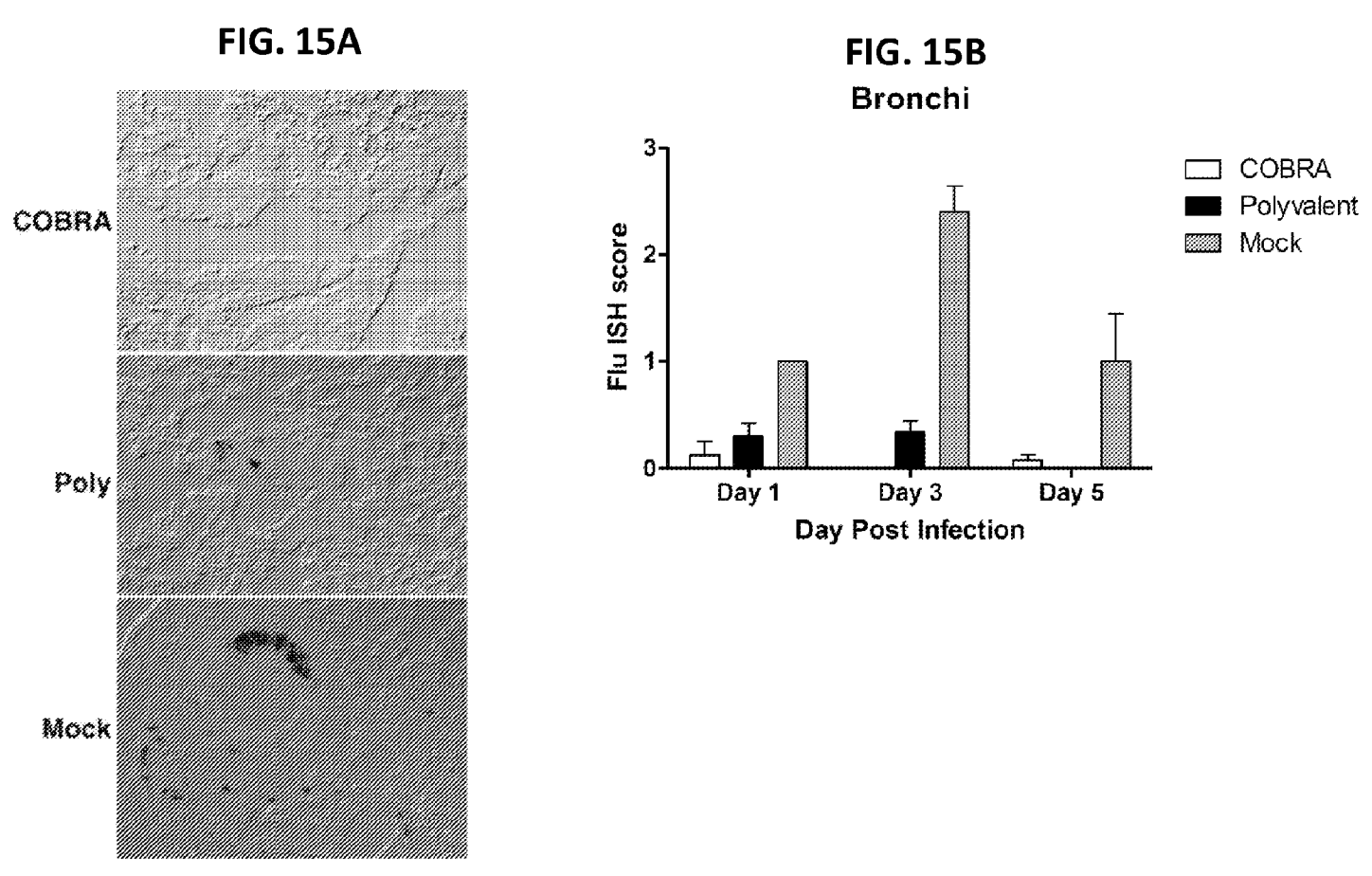

To evaluate the location and severity of influenza viral antigen and viral replication, ISH for influenza A MP was scored on 3 DPI lung sections. COBRA vaccinated animals had rare bronchial epithelium infection (FIGS. 15A and 15B). Animals receiving polyvalent vaccines had occasional bronchial epithelium infection that was comparable to the COBRA vaccinated animals (FIGS. 15A and 15B). This was in contrast to significant bronchial epithelium infection and replication observed in mock animals (FIGS. 15A and 15B).

Reassortant Clade 1 Challenge

Having established the clade 2.2 protective profile of both the COBRA and polyvalent vaccines, the efficacy of these vaccines against a more divergent clade 1 challenge in mice was evaluated. COBRA and polyvalent vaccinated mice were challenged with 6:2 reassortant virus containing the HA and NA proteins from the clade 1 virus A/Vietnam/1203/2004. All VLP vaccinated animals were protected from weight loss and death while mock vaccinated animals rapidly lost weight and reached experimental endpoint by 7 DPI (FIG. 16A). Furthermore, vaccinated mice also did not develop any signs of disease throughout the course of the study (FIG. 16B). Lungs were harvested at 3 DPI for determination of viral burden (FIG. 16C). COBRA vaccinated animals did not have detectable virus while polyvalent animals had $1.1 \times 10^3$ PFU/g virus ($p=0.12$). Importantly, both vaccines had significantly less recoverable virus than mock vaccinated animals at 3 DPI ($p<0.01$).

Post-Challenge Cellular Immune Responses

Figure 17B:
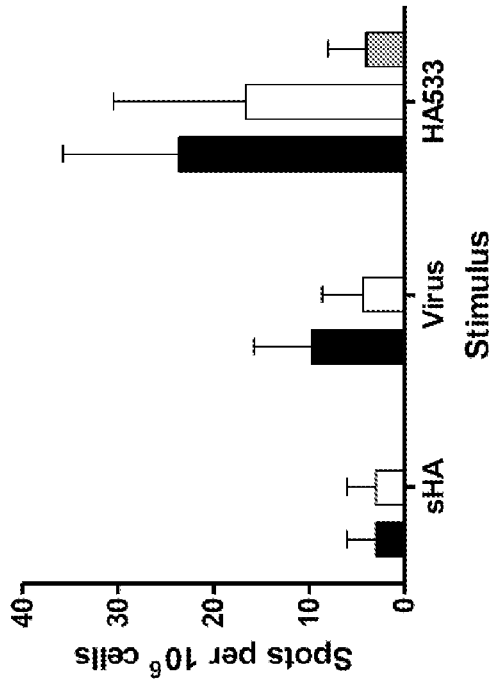
Figure 17A:
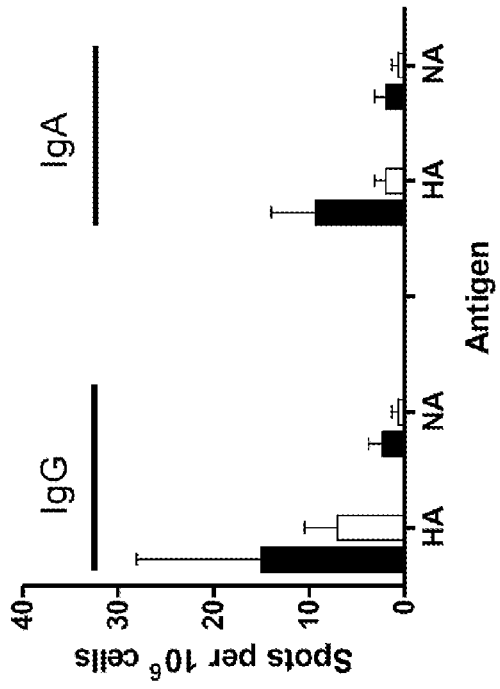

The magnitude of influenza specific cellular immune responses in the lungs post-infection was evaluated via ELISpot assay for both antibody secreting cells (ASC) and IFN-γ producing cells. Vaccinated mice were infected with reassortant A/Vietnam/1203/2994 virus as before and lungs were harvested at 6 DPI. COBRA and polyvalent vaccinated animals had statistically equivalent numbers of both IgG and IgA ASC specific for HA from the challenge virus ($p>0.05$; FIG. 17A). No ASC were detected in mock vaccinated animals indicating that the 6 DPI time point is likely representative of a recall response. Additionally, the majority of the ASC response to infection was specific for HA as lower numbers of cells were detected for the NA component of the vaccines.

VLP vaccine primed IFN-γ secreting cells were also evaluated after infection. IFN-γ responses were equivalent between VLP vaccine groups regardless of stimulating antigen ($p>0.05$; FIG. 17B). Recombinant HA and inactivated virus were inefficient stimulators of IFN-γ production compared to the $HA_{533}$ peptide. $HA_{533}$ is the immunodominant $CD8^+$ T cell epitope in BALB/c mice and is conserved in all HA vaccine antigens used in this study. Overlapping peptide pools spanning the entire HA molecule were also used to stimulate cells and no differences were observed between COBRA and polyvalent vaccines for any of the pools. Similar to the ASC data, no IFN-γ responses were detectable above background in mock vaccinated animals at 6 DPI.

Passive Transfer of Immune Sera

Figure 18A:
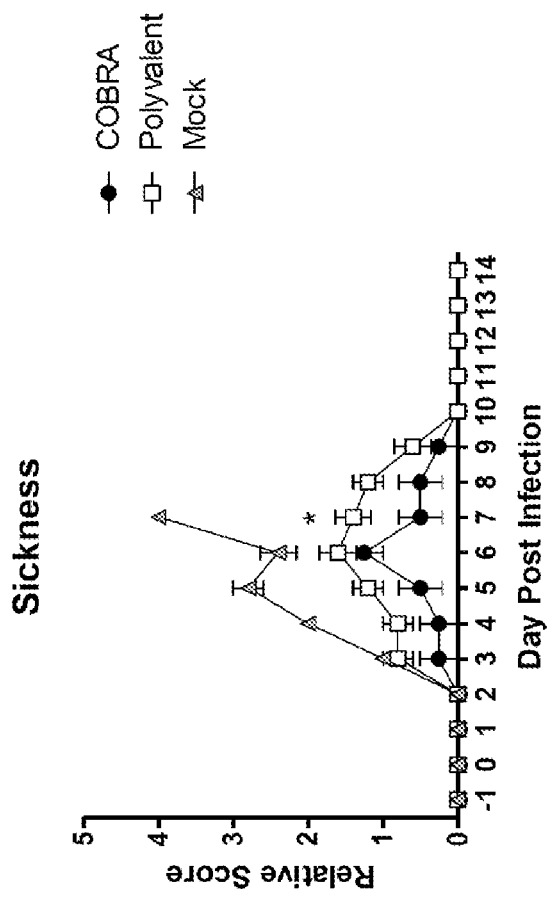
Figure 18B:
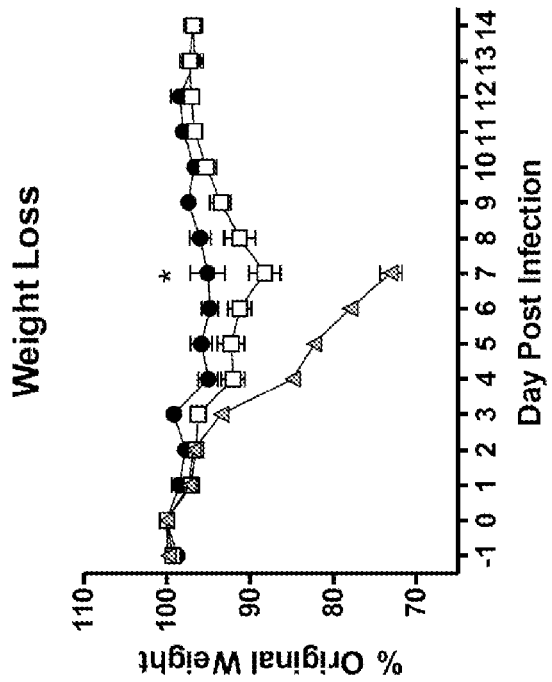

The contribution of serum factors to protection from clade 1 challenge was evaluated using a passive transfer model. Nine-week old recipient mice were administered pooled sera via IP injection from COBRA, polyvalent and mock vaccinated mice. The next day, recipient mice were challenged with the clade 1 reassortant A/Vietnam/1203/2004 virus as before. Regardless of transferred serum, all recipient mice lost weight and became visibly ill (FIGS. 18A and 18B). COBRA serum recipient mice lost less weight than polyvalent recipient mice with maximum losses of 5.2% (6 DPI) and 11.8% (7 DPI), respectively ($p<0.05$ at 7 DPI). COBRA serum recipient mice also began to resolve the clinical symptoms more rapidly than polyvalent recipient mice ($p<0.05$ at 7 DPI). Although COBRA serum prevented recipient mice from developing illness more efficiently than polyvalent serum, both COBRA and polyvalent serum protected all recipient mice from death. Conversely, all mice receiving serum from mock vaccinated mice rapidly lost weight, became visibly ill and reached experimental endpoint by 7 DPI.

In view of the many possible embodiments to which the principles of the disclosed invention may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

The invention claimed is:

1. An isolated nucleic acid molecule comprising a nucleotide sequence encoding an influenza hemagglutinin (HA) polypeptide, wherein the nucleotide sequence encoding the HA polypeptide is at least 96% identical to SEQ ID NO: 1.

2. The isolated nucleic acid molecule of claim 1, wherein the nucleotide sequence encoding the HA polypeptide comprises SEQ ID NO: 1.

3. A vector comprising the isolated nucleic acid molecule of claim 1.

4. The vector of claim 3, wherein the nucleotide sequence of the vector comprises SEQ ID NO: 7.

5. An isolated cell comprising the vector of claim 3.

6. An isolated influenza HA polypeptide, wherein the amino acid sequence of the polypeptide is at least 99% identical to SEQ ID NO: 2.

7. The influenza HA polypeptide of claim 6, wherein the amino acid sequence of the polypeptide comprises SEQ ID NO: 2.

8. A fusion protein comprising the polypeptide of claim 6 and a heterologous protein.

9. A composition comprising the influenza HA protein of claim 6 and a pharmaceutically acceptable carrier.

10. A method of eliciting an immune response to an H5 influenza virus in a subject, comprising administering the composition of claim 9.

11. The method of claim 10, further comprising administering an adjuvant.

12. The vector of claim 3, wherein the vector comprises a promoter operably linked to the nucleic acid sequence that is at least 96% identical to SEQ ID NO: 1.

13. The vector of claim 12, wherein the promoter is a cytomegalovirus (CMV) promoter.

* * * * *